United States Patent
Law et al.

(10) Patent No.: US 12,030,864 B2
(45) Date of Patent: Jul. 9, 2024

(54) SMALL MOLECULE ANTICANCER AGENTS, COMBINATIONS AND USES THEREOF

(71) Applicant: University of Florida Research Foundation, Incorporated, Gainesville, FL (US)

(72) Inventors: Brian Keith Law, Gainesville, FL (US); Ronald K. Castellano, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 697 days.

(21) Appl. No.: 17/251,289

(22) PCT Filed: Jun. 14, 2019

(86) PCT No.: PCT/US2019/037209
§ 371 (c)(1),
(2) Date: Dec. 11, 2020

(87) PCT Pub. No.: WO2019/241644
PCT Pub. Date: Dec. 19, 2019

(65) Prior Publication Data
US 2021/0147379 A1 May 20, 2021

Related U.S. Application Data

(60) Provisional application No. 62/685,856, filed on Jun. 15, 2018.

(51) Int. Cl.
| | |
|---|---|
| *C07D 339/08* | (2006.01) |
| *A61K 31/33* | (2006.01) |
| *A61K 31/385* | (2006.01) |
| *A61K 45/06* | (2006.01) |
| *A61P 35/00* | (2006.01) |
| *C07D 339/00* | (2006.01) |
| *C07D 339/04* | (2006.01) |
| *C07D 345/00* | (2006.01) |

(52) U.S. Cl.
CPC ............ *C07D 339/08* (2013.01); *A61K 31/33* (2013.01); *A61K 31/385* (2013.01); *A61K 45/06* (2013.01); *A61P 35/00* (2018.01); *C07D 339/00* (2013.01); *C07D 339/04* (2013.01); *C07D 345/00* (2013.01)

(58) Field of Classification Search
CPC ........ C07D 339/08; A61P 35/00; A61K 31/33
See application file for complete search history.

(56) References Cited

U.S. PATENT DOCUMENTS

| | | |
|---|---|---|
| 2008/0139622 A1 | 6/2008 | Wang et al. |
| 2011/0104143 A1 | 5/2011 | Buchsbaum et al. |
| 2017/0240570 A1 | 8/2017 | Jahn et al. |

OTHER PUBLICATIONS

Invitation to Pay Additional Fees dated Jul. 31, 2019 in connection with PCT/US19/37209.
International Search Report and Written Opinion dated Oct. 29, 2019 in connection with PCT/US19/37209.
International Preliminary Report on Patentability (Chapter II) dated Jul. 27, 2020 in connection with PCT/US19/37209.
Ferreira et al., Disulfide bond disrupting agents activate the unfolded protein response in EGFR- and HER2-positive breast tumor cells. Oncotarget. Apr. 2017;8(17):28971-89. Epub Mar. 7, 2017.
PCT/US19/37209, dated Jul. 31, 2019, Invitation to Pay Additional Fees.
PCT/US19/37209, dated Oct. 29, 2019, International Search Report and Written Opinion.
PCT/US19/37209, dated Jul. 27, 2020, International Preliminary Report on Patentability (Chapter II).

*Primary Examiner* — Kamal A Saeed
(74) *Attorney, Agent, or Firm* — Wolf, Greenfield & Sacks, P.C.

(57) ABSTRACT

The invention relates to methods of treating cell proliferative disorders. The invention further relates to pharmaceutical compositions for treating cell proliferative disorders, especially cancer.

14 Claims, 15 Drawing Sheets

BGPD = BioGlyPyrDTDO

| TRAIL (ng/ml) | 3.125 | 6.25 | 12.5 | 25 | 50 |
|---|---|---|---|---|---|
| tcyDTDO (µM) | 0.625 | 1.25 | 2.5 | 5 | 10 |
| CI | 3.411 | 0.895 | 0.556 | 0.773 | 0.998 |
| Description | Strong antagonism | Slight synergism | Synergism | Moderate synergism | Nearly additive |
| | ---- | + | +++ | ++ | ± |

SMALL MOLECULE ANTICANCER AGENTS, COMBINATIONS AND USES THEREOF

RELATED APPLICATIONS

This application is a national stage filing under 35 U.S.C. 371 of International Patent Application Ser. No. PCT/US2019/037209, filed Jun. 14, 2019, entitled "NOVEL SMALL MOLECULE ANTICANCER AGENTS, COMBINATIONS AND USES THEREOF", which claims the benefit under 35 U.S.C. § 119(e) of the filing date of U.S. Provisional Application Ser. No. 62/685,856, filed Jun. 15, 2018, entitled "NOVEL SMALL MOLECULE ANTICANCER AGENT", the entire contents of each of which is incorporated by reference herein in their entirety.

STATEMENT OF GOVERNMENT SUPPORT

This invention was made with government support under Grant Nos. W81XWH-15-1-0199 and W81XWH-15-1-0200 by the US Army Medical Research Acquisition (USAMRAA) and Subgrant Nos. BC140133 and BC140133P1 awarded by the Breast Cancer Research Program. The government has certain rights in the invention.

BACKGROUND OF THE INVENTION

The Epidermal Growth Factor Receptor (EGFR) family members EGFR, Human Epidermal growth factor Receptor-2 (HER2), and Human Epidermal growth factor Receptor-3 (HER3) are well established as proto-oncogenes that play key roles in the initiation and progression of human cancers [Arslan, M. A., Kutuk, O., and Basaga, H. (2006) Protein kinases as drug targets in cancer Curr Cancer Drug Targets 6, 623-634; Yan, M., Parker, B. A., Schwab, R., and Kurzrock, R. (2014) HER2 aberrations in cancer: Implications for therapy Cancer Treat Rev 40, 770-780; Foley, J., Nickerson, N. K., Nam, S., Allen, K. T., Gilmore, J. L., Nephew, K. P., and Riese, D. J., 2nd. (2010) EGFR signaling in breast cancer: bad to the bone Semin Cell Dev Biol 21, 951-960]. EGFR is frequently mutationally activated in lung cancer and is the target of the FDA-approved drugs Cetuximab, Panitumumab, and Erlotinib. Although EGFR is rarely mutated in breast cancers, the wild type protein is frequently overexpressed in breast tumors, and EGFR has been suggested to be a therapeutic target in triple-negative (Estrogen Receptor-, Progesterone Receptor-, and HER2-negative) breast cancers [Park, H. S., Jang, M. H., Kim, E. J., Kim, H. J., Lee, H. J., Kim, Y. J., Kim, J. H., Kang, E., Kim, S. W., Kim, I. A., and Park, S. Y. (2014) High EGFR gene copy number predicts poor outcome in triple-negative breast cancer Mod Pathol].

Examination of the extracellular domains of EGFR, HER2, and HER3 [Garrett T P, McKern N M, Lou M, Elleman T C, Adams T E, et al. (2003) The crystal structure of a truncated ErbB2 ectodomain reveals an active conformation, poised to interact with other ErbB receptors. Mol Cell 11: 495-505; Cho H S, Mason K, Ramyar K X, Stanley A M, Gabelli S B, et al. (2003) Structure of the extracellular region of HER2 alone and in complex with the Herceptin Fab. Nature 421: 756-760; Cho H S, Leahy D J (2002) Structure of the extracellular region of HER3 reveals an interdomain tether. Science 297: 1330-1333; Field L, Khim Y H (1972) Organic disulfides and related substances. 33. Sodium 4-(2-acetamidoethyldithio)butanesulfinate and related compounds as antiradiation drugs. J Med Chem 15: 312-315] reveals a complicated pattern of structural repeats that are held in place by disulfide bonds. Agents capable of disrupting disulfide bonds may preferentially destabilize the structures of HER2, EGFR, and HER3 and inhibit their oncogenic functions. Optimal disulfide bond disrupting agents (DDAs) would target extracellular disulfide bonds, be charged at physiological pH to minimize entry into cells in order to reduce off-target effects, and would employ chemistry that does not affect nucleic acids. DDAs meeting these criteria are expected to be toxic to cancer cells that depend on HER2 for proliferation and survival, but to be well tolerated by normal tissues.

TRAIL (tumor necrosis factor (TNF)-related apoptosis-inducing ligand) is a member of the TNF superfamily with the ability to induce apoptosis of tumor cells. TRAIL is known to interact with at least five receptors (e.g., DR4 (TRAIL-R1) and DR5 (TRAIL-R2)). TRAIL and agonistic antibodies that recognize TRAIL receptors preferentially kill tumor cells and induce potent anti-tumor activity in a variety of experimental models (see, Griffith T S, et al., Curr Opin Immunol. 1998; 10:559 563, Ashkenazi A, et al., J. Clin Invest. 1999; 104:155-162, Walczak H. et al, Nat Med. 1999; 5:157-163, Chuntharapai A, et al., J Immunol. 2001; 166: 4891-4898, and Ichikawa K, et al., Nat Med. 2001; 7: 954-960). Administration of TRAIL to mice bearing human tumors actively suppressed tumor progression and improved survival of the animal (Walczak H. et al, Nat Med. 1999; 5:157-163).

Herein we describe the combination of compounds of any formulae herein and DR5 agonists (e.g., TRAIL), and its use in treating various diseases and disorders (e.g., breast cancer).

SUMMARY OF THE INVENTION

In one aspect, the invention provides a compound of Formula I, or salt, solvate, hydrate or prodrug thereof:

Formula I wherein, each X is independently S or Se;

each Y is independently S, $SO_2$, or Se;

each Z is independently S, $SO_2$, or Se;

each $R_1$ is independently selected from H, $NH_2$, $N_3$, OH, oxo, OAc, NH—$R_3$, each $R_2$ is independently selected from H, $NH_2$, $N_3$, OH, oxo, OAc, NH—$R_3$,

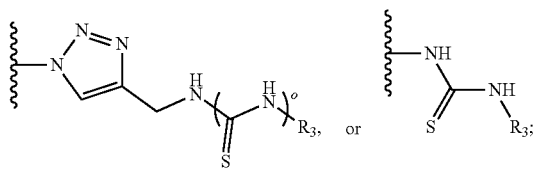

each $R_3$ is independently selected from biotin, fluorescein, AlexaFluor® dyes, BODIPY®, Cascade Blue®, coumarins, Oregon Green®, Pacific Blue®, Pacific Green™, Pacific Orange™, Rhodamine Green™, Rhodamine Red™, or Texas Red®;

or adjacent $R_1$, $R_2$ moieties, and the carbon atoms to which they are attached form an optionally substituted cycloalkyl moiety;

each $R_7$ is independently H, Na, K, optionally substituted alkyl, optionally substituted aryl, or optionally substituted arylalkyl;

each n is independently 0 or 1;

each o is independently 0 or 1; and

--- denotes a carbon-carbon single bond or double bond;

In another aspect, the compound of Formula I is

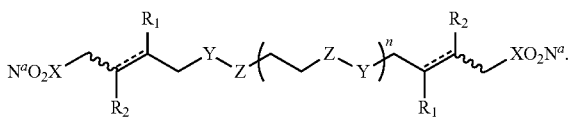

In another aspect, the invention provides a compound of Formula II, or salt, solvate, hydrate or prodrug thereof:

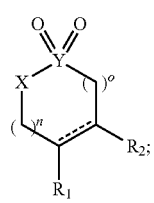

Formula II wherein, X is S or Se;

Y is S or Se;

$R_1$ is selected from H, $NH_2$, $N_3$, OAc, alkyl, or OH;

$R_2$ is selected from H, $NH_2$, $N_3$, OAc, alkyl, or OH;

n is 0, 1, 2, or 3;

is 0, 1, 2, or 3;

or $R_1$, $R_2$, and the carbon atoms to which they are attached form an optionally substituted cycloalkyl moiety or optionally substituted aryl moiety; and --- denotes a carbon-carbon single bond or double bond.

In another aspect, the invention provides a compound of Formula III, or salt, solvate, hydrate or prodrug thereof:

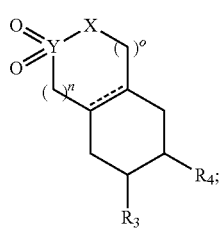

Formula III wherein, X is S or Se;

Y is S or Se;

$R_3$ is selected from H or $C_1$-$C_6$ alkoxy;

$R_4$ is selected from H or $C_1$-$C_6$ alkoxy;

n is 0, 1, 2, or 3;

is 0, 1, 2, or 3; and

--- denotes a carbon-carbon single bond or double bond;

wherein if --- is a single bond, X and Y are both S, and n and o are each 1, then at least one of $R_3$ or $R_4$ is $C_1$-$C_6$ alkoxy.

In another aspect, the compound of Formula (III), or salt, solvate, hydrate or prodrug thereof, is according to Formula (IV):

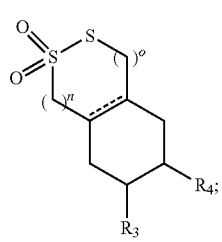

Formula IV or salt, solvate, hydrate or prodrug thereof.

In another aspect, the compound of Formula (III), or salt, solvate, hydrate or prodrug thereof, is according to Formula (V):

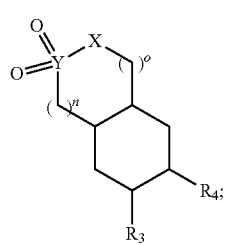

Formula V or salt, solvate, hydrate or prodrug thereof.

In another aspect, the compound of Formula (III), or salt, solvate, hydrate or prodrug thereof, is according to Formula (VI):

Formula VI

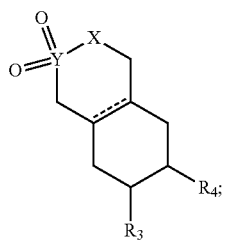

or salt, solvate, hydrate or prodrug thereof.

In another aspect, the compound of Formula (III), or salt, solvate, hydrate or prodrug thereof, is according to Formula (VII):

Formula VII

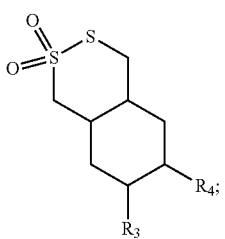

or salt, solvate, hydrate or prodrug thereof.

In another aspect, the compound of Formula (III), or salt, solvate, hydrate or prodrug thereof, is according to Formula (VIII):

Formula VIII

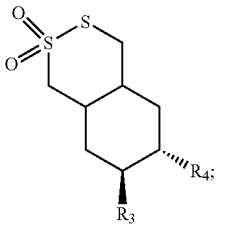

or salt, solvate, hydrate or prodrug thereof.

In another aspect, the compound of Formula (III), or salt, solvate, hydrate or prodrug thereof, is according to Formula (IX):

Formula IX

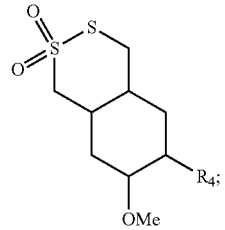

or salt, solvate, hydrate or prodrug thereof.

In another aspect, the compound of Formula (III), or salt, solvate, hydrate or prodrug thereof, is according to Formula (X):

Formula X

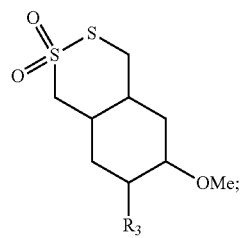

or salt, solvate, hydrate or prodrug thereof.

In another aspect, the compound of Formula (III), or salt, solvate, hydrate or prodrug thereof, is according to Formula (XI):

Formula XI

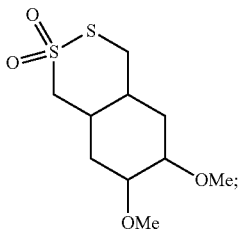

or salt, solvate, hydrate or prodrug thereof.

In another aspect, the compound of Formula (III), or salt, solvate, hydrate or prodrug thereof, is according to Formula (XII):

Formula XII

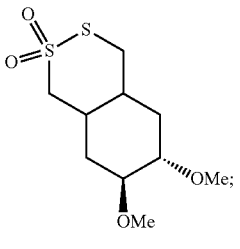

or salt, solvate, hydrate or prodrug thereof.

In another aspect, the compound of Formula (III), or salt, solvate, hydrate or prodrug thereof, is according to Formula (XIII):

Formula XIII

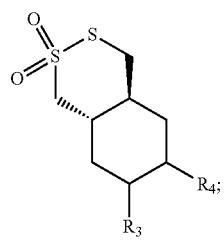

or salt, solvate, hydrate or prodrug thereof.

In another aspect, the compound of Formula (III), or salt, solvate, hydrate or prodrug thereof, is according to Formula (XIV):

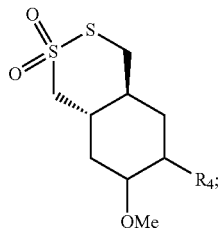

Formula XIV or salt, solvate, hydrate or prodrug thereof.

In another aspect, the compound of Formula (III), or salt, solvate, hydrate or prodrug thereof, is according to Formula (XV):

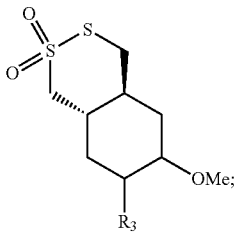

Formula XV or salt, solvate, hydrate or prodrug thereof.

In another aspect, the compound of Formula (III), or salt, solvate, hydrate or prodrug thereof, is according to Formula (XVI):

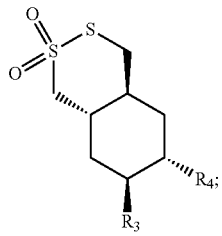

Formula XVI or salt, solvate, hydrate or prodrug thereof.

In another aspect, the compound of Formula (III), or salt, solvate, hydrate or prodrug thereof, is according to Formula (XVII):

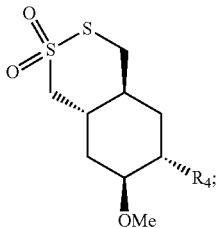

Formula XVII or salt, solvate, hydrate or prodrug thereof.

In another aspect, the compound of Formula (III), or salt, solvate, hydrate or prodrug thereof, is according to Formula (XVIII):

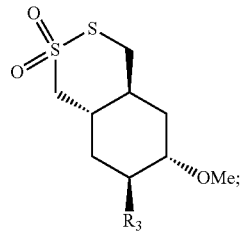

Formula XVIII or salt, solvate, hydrate or prodrug thereof.

In another aspect, the compound of Formula (III), or salt, solvate, hydrate or prodrug thereof, is according to (+/−)-Formula (XIX):

(+/−)-

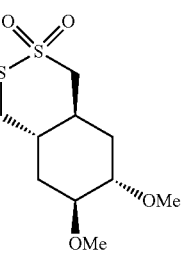

Formula XIX (also referred to herein as DMtcyDTDO);

or salt, solvate, hydrate or prodrug thereof.

In another aspect, the invention provides a pharmaceutical composition comprising a compound of any one of Formulae III-XIX, or salt, solvate, hydrate or prodrug thereof, and a pharmaceutically acceptable carrier. In another aspect, the pharmaceutical composition comprises an additional agent. In another aspect, the additional agent is a DR5 agonist. In another aspect, the compound of Formulae III-XIX, or salt, solvate, hydrate or prodrug thereof, is (+/−)-

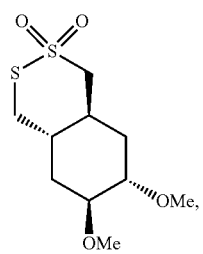 [SMILES: CO[C@H]1C[C@@H]2CS(=O)(=O)SC[C@H]2C[C@@H]1OC]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formulae III-XIX, or salt, solvate, hydrate or prodrug thereof, is (+/−)-

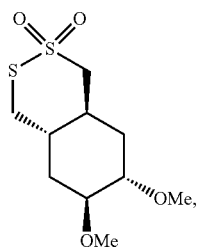

or salt, solvate, hydrate or prodrug thereof, and the DR5 agonist is TRAIL.

In another aspect, the invention provides a pharmaceutical composition comprising: 1) a compound of Formula (I)-(VI), or salt, solvate, hydrate or prodrug thereof; 2) a DR5 agonist; and 3) a pharmaceutically acceptable carrier. In another aspect, the compound of Formula (I)-(VI) is

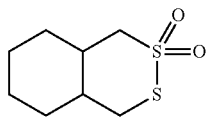 [SMILES: O=S1(=O)CC2CCCCC2CS1]

(also referred to herein as tcyDTDO), or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

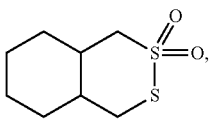 [SMILES: O=S1(=O)CC2CCCCC2CS1]

or salt, solvate, hydrate or prodrug thereof, and the DR5 agonist is TRAIL.

In another aspect, the invention provides a dosing regimen for treating a cell proliferative disorder in a subject, the dosing regimen comprising: 1) a compound of Formula (I)-(VI), or salt, solvate, hydrate or prodrug thereof; and 2) a DR5 agonist. In another aspect, the dosing regimen further comprises a pharmaceutically acceptable carrier. In another aspect, the compound of Formula (I)-(VI) is

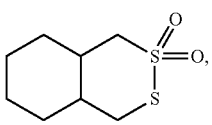 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

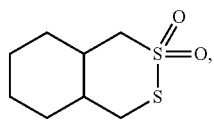 [SMILES: O=S1(=O)CC2CCCCC2CS1]

or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a dosing regimen for treating a cell proliferative disorder in a subject, the dosing regimen comprising: 1) a compound of Formulae III-XIX, or salt, solvate, hydrate or prodrug thereof; and 2) a DR5 agonist. In another aspect, the dosing regimen further comprises a pharmaceutically acceptable carrier. In another aspect, the compound of Formulae III-XIX, or salt, solvate, hydrate or prodrug thereof, is (+/−)-

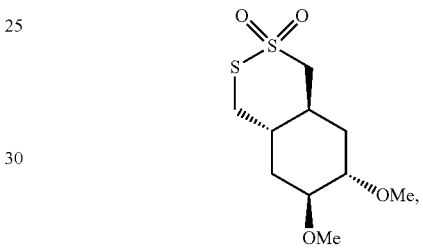

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formulae III-XIV, or salt, solvate, hydrate or prodrug thereof, is (+/−)-

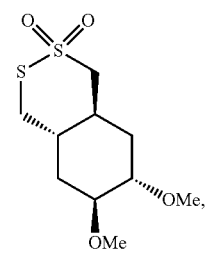 [SMILES: CO[C@H]1C[C@@H]2CS(=O)(=O)SC[C@H]2C[C@@H]1OC]

or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In one aspect, the invention provides a method of treating a subject suffering from or susceptible to a cell proliferative disorder. The method includes administering to a subject in need thereof a therapeutically effective amount of a compound of Formula I, or salt, solvate, hydrate or prodrug thereof:

Formula I

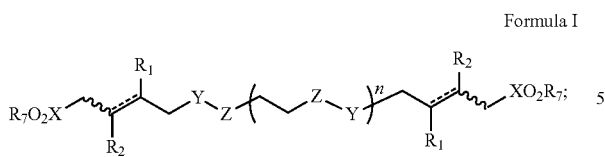

wherein, each X is independently S or Se;
each Y is independently S, SO$_2$, or Se;
each Z is independently S, SO$_2$, or Se;
each R$_1$ is independently selected from H, NH$_2$, N$_3$, OH, oxo, OAc, NH—R$_3$,

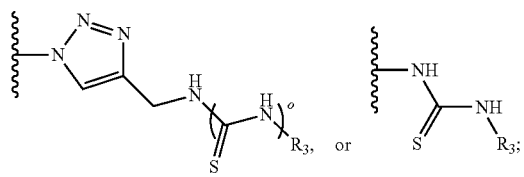

each R$_2$ is independently selected from H, NH$_2$, N$_3$, OH, oxo, OAc, NH—R$_3$,

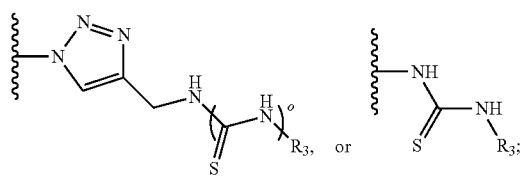

each R$_3$ is independently selected from biotin, fluorescein, AlexaFluor® dyes, BODIPY®, Cascade Blue®, coumarins, Oregon Green®, Pacific Blue™, Pacific Green™, Pacific Orange™, Rhodamine Green™, Rhodamine Red™, or Texas Red®;
or adjacent R$_1$, R$_2$ moieties, and the carbon atoms to which they are attached form an optionally substituted cycloalkyl moiety;
each R$_7$ is independently H, Na, K, optionally substituted alkyl, optionally substituted aryl, or optionally substituted arylalkyl;
each n is independently 0 or 1;
each o is independently 0 or 1; and
---- denotes a carbon-carbon single bond or double bond. In another aspect, the compound of Formula I is

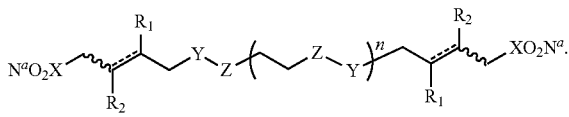

In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of treating a subject suffering from or susceptible to a cell proliferative disorder. The method includes administering to a subject in need thereof a therapeutically effective amount of a compound of Formula II, or salt, solvate, hydrate or prodrug thereof:

Formula II

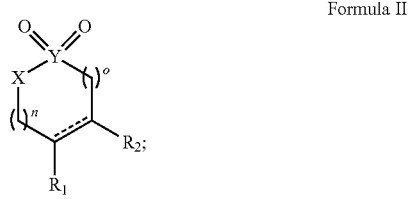

wherein, X is S or Se;
Y is S or Se;
R$_1$ is selected from H, NH$_2$, N$_3$, OAc, alkyl, or OH;
R$_2$ is selected from H, NH$_2$, N$_3$, OAc, alkyl, or OH;
n is 0, 1, 2, or 3;
is 0, 1, 2, or 3;
or R$_1$, R$_2$, and the carbon atoms to which they are attached form an optionally substituted cycloalkyl moiety or optionally substituted aryl moiety; and
denotes a carbon-carbon single bond or double bond. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of treating a subject suffering from or susceptible to a cell proliferative disorder. The method includes administering to a subject in need thereof a therapeutically effective amount of a compound of Formula (I)-(VI), or salt, solvate, hydrate or prodrug thereof; and a therapeutically effective amount of DR5 agonist. In another aspect, the compound of Formula (I)-(VI), or salt, solvate, hydrate or prodrug thereof, and the DR5 agonist are administered sequentially. In another aspect, the compound of Formula (I)-(VI), or salt, solvate, hydrate or prodrug thereof, and the DR5 agonist are administered simultaneously. In another aspect, the compound of Formula (I)-(VI) is

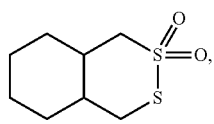 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

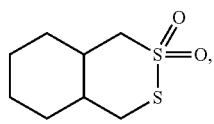 [SMILES: O=S1(=O)CC2CCCCC2CS1]

or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of treating a subject suffering from or susceptible to a cell proliferative disorder. The method includes administering to a subject in need thereof a pharmaceutical composition comprising: 1) a therapeutically effective amount of a compound of Formula (I)-(VI), or salt, solvate, hydrate or prodrug thereof; 2) a therapeutically effective amount of DR5 agonist; and 3) a pharmaceutically acceptable carrier. In another aspect, the compound of Formula (I)-(VI) is

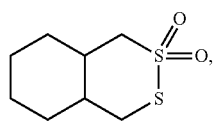 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

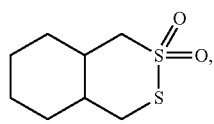 [SMILES: O=S1(=O)CC2CCCCC2CS1]

or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of treating a subject suffering from or susceptible to a cell proliferative disorder. The method includes administering to a subject in need thereof a therapeutically effective amount of a compound of Formula III, or salt, solvate, hydrate or prodrug thereof.

Formula III

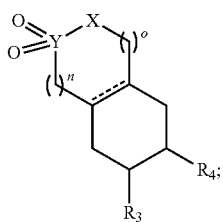

wherein, X is S or Se;
Y is S or Se;
$R_3$ is selected from H or $C_1$-$C_6$ alkoxy;
$R_4$ is selected from H or $C_1$-$C_6$ alkoxy;
n is 0, 1, 2, or 3;
is 0, 1, 2, or 3; and --- denotes a carbon-carbon single bond or double bond;
wherein if --- is a single bond, X and Y are both S, and n and o are each 1, then at least one of $R_3$ or $R_4$ is $C_1$-$C_6$ alkoxy. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of treating a subject suffering from or susceptible to a cell proliferative disorder. The method includes administering to a subject in need thereof a therapeutically effective amount of a compound of any one of Formulae III-XIX, or salt, solvate, hydrate or prodrug thereof; and a therapeutically effective amount of DR5 agonist. In another aspect, the compound of Formulae I-XIX, or salt, solvate, hydrate or prodrug thereof, and the DR5 agonist are administered sequentially. In another aspect, the compound of Formulae I-XIX, or salt, solvate, hydrate or prodrug thereof, and the DR5 agonist are administered simultaneously. In another aspect, the compound of Formulae III-XIX, or salt, solvate, hydrate or prodrug thereof, is (+/−)-

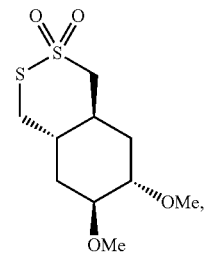 [SMILES: CO[C@H]1C[C@@H]2CS(=O)(=O)SC[C@H]2C[C@@H]1OC]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formulae III-XIV, or salt, solvate, hydrate or prodrug thereof, is (+/−)-

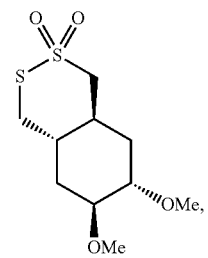 [SMILES: CO[C@H]1C[C@@H]2CS(=O)(=O)SC[C@H]2C[C@@H]1OC]

or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of treating a subject suffering from or susceptible to a cell proliferative disorder. The method includes administering to a subject in need thereof a pharmaceutical composition comprising a compound of any one of Formulae III-XIX, or salt, solvate, hydrate or prodrug thereof, and a pharmaceutically acceptable carrier. In another aspect, the pharmaceutical composition comprises an additional agent. In another aspect, the additional agent is a DR5 agonist. In another aspect, the compound of Formulae III-XIX, or salt, solvate, hydrate or prodrug thereof, is (+/−)-

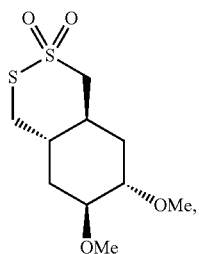 [SMILES: CO[C@H]1C[C@@H]2CS(=O)(=O)SC[C@H]2C[C@@H]1OC]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formulae III-XIX, or salt, solvate, hydrate or prodrug thereof, is (+/−)-

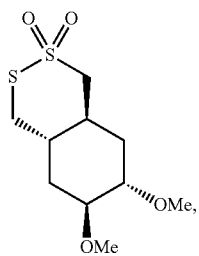 [SMILES: CO[C@H]1C[C@@H]2CS(=O)(=O)SC[C@H]2C[C@@H]1OC]

or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting cell proliferation. The method includes administering to the cell a therapeutically effective amount of a compound of Formula I, or salt, solvate, hydrate or prodrug thereof.

Formula I

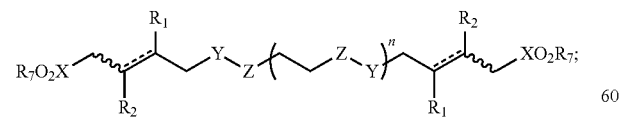

wherein, each X is independently S or Se;
each Y is independently S, SO$_2$, or Se;
each Z is independently S, SO$_2$, or Se;
each R$_1$ is independently selected from H, NH$_2$, N$_3$, OH, oxo, OAc, NH—R$_3$,

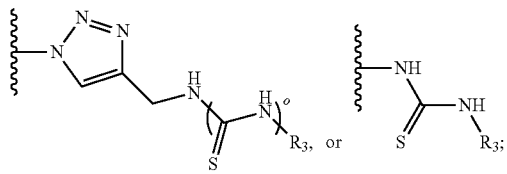

each R$_2$ is independently selected from H, NH$_2$, N$_3$, OH, oxo, OAc, NH—R$_3$,

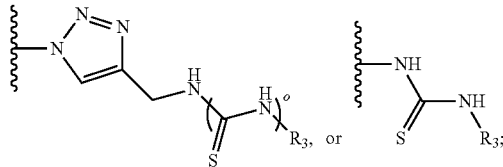

each R$_3$ is independently selected from biotin, fluorescein, AlexaFluor® dyes, BODIPY®, Cascade Blue®, coumarins, Oregon Green®, Pacific Blue™, Pacific Green™, Pacific Orange™, Rhodamine Green™, Rhodamine Red™, or Texas Red®;
or adjacent R$_1$, R$_2$ moieties, and the carbon atoms to which they are attached form an optionally substituted cycloalkyl moiety;
each R$_7$ is independently H, Na, K, optionally substituted alkyl, optionally substituted aryl, or optionally substituted arylalkyl;
each n is independently 0 or 1;
each o is independently 0 or 1; and
═══ denotes a carbon-carbon single bond or double bond.
In another aspect, the compound of Formula I is

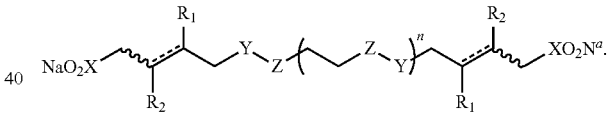

In another aspect, the cell proliferative disorder is cancer. In a further aspect, the cancer cell is HER2 mediated. In a further aspect, the cancer cell is breast cancer. In a further aspect, the breast cancer cell is HER2-positive breast cancer cell. In another aspect, the breast cancer cell is modulated by HER2, HER3, and/or EGFR.

In another aspect, the invention provides a method of inhibiting cell proliferation. The method includes administering to the cell a therapeutically effective amount of a compound of Formula II, or salt, solvate, hydrate or prodrug thereof:

Formula II

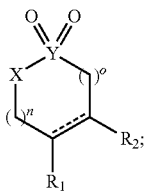

wherein, X is S or Se;
Y is S or Se;
R$_1$ is selected from H, NH$_2$, N$_3$, OAc, alkyl, or OH;

$R_2$ is selected from H, $NH_2$, $N_3$, OAc, alkyl, or OH;

n is 0, 1, 2, or 3;

is 0, 1, 2, or 3;

or $R_1$, $R_2$, and the carbon atoms to which they are attached form an optionally substituted cycloalkyl moiety or an optionally substituted aryl moiety; and =--= denotes a carbon-carbon single bond or double bond. In another aspect, the cell proliferative disorder is cancer. In a further aspect, the cancer cell is HER2 mediated. In a further aspect, the cancer cell is breast cancer. In a further aspect, the breast cancer cell is HER2-positive breast cancer cell. In another aspect, the breast cancer cell is modulated by HER2, HER3, and/or EGFR.

In another aspect, the invention provides a method of inhibiting cell proliferation. The method includes administering to the cell a therapeutically effective amount of a compound of Formula (I)-(VI), or salt, solvate, hydrate or prodrug thereof; and a therapeutically effective amount of DR5 agonist. In another aspect, the compound of Formula (I)-(VI), or salt, solvate, hydrate or prodrug thereof, and the DR5 agonist are administered sequentially. In another aspect, the compound of Formula (I)-(VI), or salt, solvate, hydrate or prodrug thereof, and the DR5 agonist are administered simultaneously. In another aspect, the cell is in vitro. In another aspect, the cell is in a subject. In another aspect, the compound of Formula (I)-(VI) is or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting cell proliferation. The method includes administering to the cell a pharmaceutical composition comprising: 1) a therapeutically effective amount of a compound of Formula (I)-(VI), or salt, solvate, hydrate or prodrug thereof; 2) a therapeutically effective amount of DR5 agonist; and 3) a pharmaceutically acceptable carrier. In another aspect, the cell is in vitro. In another aspect, the cell is in a subject. In another aspect, the compound of Formula (I)-(VI) is or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting cell proliferation. The method includes administering to the cell a therapeutically effective amount of a compound of Formula III, or salt, solvate, hydrate or prodrug thereof:

Formula III wherein, X is S or Se;

Y is S or Se;

$R_3$ is selected from H or $C_1$-$C_6$ alkoxy;

$R_4$ is selected from H or $C_1$-$C_6$ alkoxy;

n is 0, 1, 2, or 3;

is 0, 1, 2, or 3; and

=--= denotes a carbon-carbon single bond or double bond;

wherein if =--= is a single bond, X and Y are both S, and n and o are each 1, then at least one of $R_3$ or $R_4$ is $C_1$-$C_6$ alkoxy. In a further aspect, the cancer cell is HER2 mediated. In a further aspect, the cancer cell is breast cancer. In a further aspect, the breast cancer cell is HER2-positive breast cancer cell. In another aspect, the breast cancer cell is modulated by HER2, HER3, and/or EGFR. In another aspect, the cell is in vitro. In another aspect, the cell is in a subject. In another aspect, the method includes administering to the cell a therapeutically effective amount of a compound of any one of Formulae III-XIX, or salt, solvate, hydrate or prodrug thereof; and a therapeutically effective amount of DR5 agonist. In another aspect, the compound of Formulae III-XIX, or salt, solvate, hydrate or prodrug thereof, and the DR5 agonist are administered sequentially. In another aspect, the compound of Formulae III-XIX, or salt, solvate, hydrate or prodrug thereof, and the DR5 agonist are administered simultaneously.

In another aspect, the invention provides a method of inhibiting cell proliferation. The method includes administering to the cell a pharmaceutical composition comprising a compound of any one of Formulae III-XIX, or salt, solvate, hydrate or prodrug thereof, and a pharmaceutically acceptable carrier. In another aspect, the pharmaceutical composition comprises an additional agent. In another aspect, the additional agent is a DR5 agonist. In another aspect, the cell is in vitro. In another aspect, the cell is in a subject.

In another aspect, the invention provides a method of inhibiting cancer cell metastasis. The method includes administering to a subject in need thereof a therapeutically effective amount of a compound of Formula I, or salt, solvate, hydrate or prodrug thereof.

Formula I

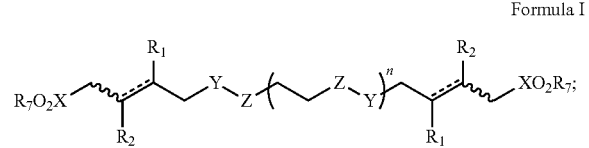

wherein, each X is independently S or Se;
each Y is independently S, $SO_2$, or Se;
each Z is independently S, $SO_2$, or Se;
each $R_1$ is independently selected from H, $NH_2$, $N_3$, OH, oxo, OAc, NH—$R_3$, each $R_2$ is independently selected from H, $NH_2$, $N_3$, OH, oxo, OAc, NH—$R_3$, each $R_3$ is independently selected from biotin, fluorescein, AlexaFluor® dyes, BODIPY®, Cascade Blue®, coumarins, Oregon Green®, Pacific Blue™, Pacific Green™, Pacific Orange™, Rhodamine Green™, Rhodamine Red™, or Texas Red®;
or adjacent $R_1$, $R_2$ moieties, and the carbon atoms to which they are attached form an optionally substituted cycloalkyl moiety;
each $R_7$ is independently H, Na, K, optionally substituted alkyl, optionally substituted aryl, or optionally substituted arylalkyl;
each n is independently 0 or 1;
each o is independently 0 or 1; and
══ denotes a carbon-carbon single bond or double bond.
In another aspect, the compound of Formula I is In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting cancer cell metastasis. The method includes administering to a subject in need thereof a therapeutically effective amount of a compound of Formula II, or salt, solvate, hydrate or prodrug thereof:

Formula II wherein, X is S or Se;
Y is S or Se;
$R_1$ is selected from H, $NH_2$, $N_3$, OAc, alkyl, or OH;
$R_2$ is selected from H, $NH_2$, $N_3$, OAc, alkyl, or OH;
n is 0, 1, 2, or 3;
is 0, 1, 2, or 3;
or $R_1$, $R_2$, and the carbon atoms to which they are attached form an optionally substituted cycloalkyl moiety or an optionally substituted aryl moiety; and
══ denotes a carbon-carbon single bond or double bond. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting cancer cell metastasis. The method includes administering to a subject in need thereof a therapeutically effective amount of a compound of Formula (I)-(VI), or salt, solvate, hydrate or prodrug thereof; and a therapeutically effective amount of DR5 agonist. In another aspect, the compound of Formula (I)-(VI), or salt, solvate, hydrate or prodrug thereof, and the DR5 agonist are administered sequentially. In another aspect, the compound of Formula (I)-(VI), or salt, solvate, hydrate or prodrug thereof, and the DR5 agonist are administered simultaneously. In another aspect, the cell is in vitro. In another aspect, the cell is in a subject. In another aspect, the compound of Formula (I)-(VI) is

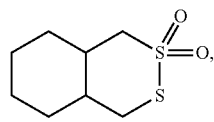

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

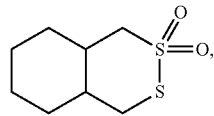 [SMILES: O=S1(=O)CC2CCCCC2CS1]

or salt, solvate, hydrate or prodrug thereof, and the DR5 agonist is TRAIL. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting cancer cell metastasis. The method includes administering to a subject in need thereof a pharmaceutical composition comprising: 1) a therapeutically effective amount of a compound of Formula (I)-(VI), or salt, solvate, hydrate or prodrug thereof; 2) a therapeutically effective amount of DR5 agonist; and 3) a pharmaceutically acceptable carrier. In another aspect, the compound of Formula (I)-(VI) is

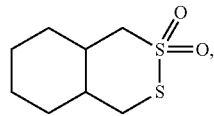 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

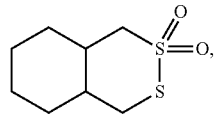 [SMILES: O=S1(=O)CC2CCCCC2CS1]

or salt, solvate, hydrate or prodrug thereof, and the DR5 agonist is TRAIL. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a method of inhibiting cancer cell metastasis. The method includes administering to a subject in need thereof a therapeutically effective amount of a compound of Formula III, or salt, solvate, hydrate or prodrug thereof.

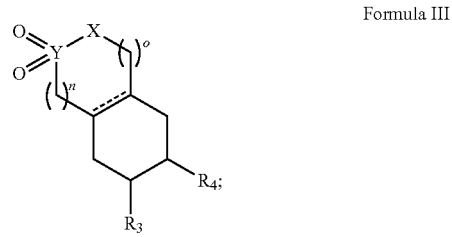

Formula III wherein, X is S or Se;
Y is S or Se;
$R_3$ is selected from H or $C_1$-$C_6$ alkoxy;
$R_4$ is selected from H or $C_1$-$C_6$ alkoxy;
n is 0, 1, 2, or 3;
is 0, 1, 2, or 3; and
═══ denotes a carbon-carbon single bond or double bond;
wherein if ═══ is a single bond, X and Y are both S, and n and o are each 1, then at least one of $R_3$ or $R_4$ is $C_1$-$C_6$ alkoxy. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR. In another aspect, the method includes administering to a subject in need thereof a therapeutically effective amount of a compound of any one of Formulae III-XIX, or salt, solvate, hydrate or prodrug thereof. The method includes administering to a subject in need thereof a therapeutically effective amount of a compound of any one of Formulae III-XIX, or salt, solvate, hydrate or prodrug thereof; and a therapeutically effective amount of DR5 agonist. In another aspect, the compound of Formulae III-XIX, or salt, solvate, hydrate or prodrug thereof, and the DR5 agonist are administered sequentially. In another aspect, the compound of Formulae III-XIX, or salt, solvate, hydrate or prodrug thereof, and the DR5 agonist are administered simultaneously. In another aspect, the cell is in vitro. In another aspect, the cell is in a subject.

In another aspect, the invention provides a method of inhibiting cancer cell metastasis. The method includes administering to a subject in need thereof a pharmaceutical composition comprising a therapeutically effective amount of a compound of any one of Formulae III-XIX, or salt, solvate, hydrate or prodrug thereof; and a pharmaceutically acceptable carrier. The method includes administering to a subject in need thereof a pharmaceutical composition comprising: 1) a therapeutically effective amount of a compound of any one of Formulae III-XIX, or salt, solvate, hydrate or prodrug thereof; 2) a therapeutically effective amount of DR5 agonist; and 3) a pharmaceutically acceptable carrier.

In another aspect, the invention provides a kit for treating a cell proliferative disorder in a subject. The kit includes a compound of Formula I, or salt, solvate, hydrate or prodrug thereof:

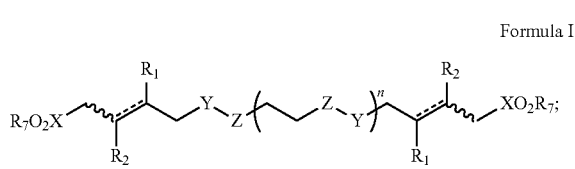

Formula I wherein, each X is independently S or Se;
each Y is independently S, SO$_2$, or Se;
each Z is independently S, SO$_2$, or Se;
each R$_1$ is independently selected from H, NH$_2$, N$_3$, OH, oxo, OAc, NH—R$_3$,

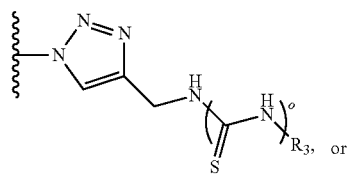

each R$_2$ is independently selected from H, NH$_2$, N$_3$, OH, oxo, OAc, NH—R$_3$,

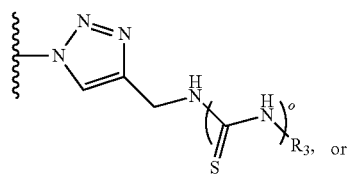

each R$_3$ is independently selected from biotin, fluorescein, AlexaFluor® dyes, BODIPY®, Cascade Blue®, coumarins, Oregon Green®, Pacific Blue™, Pacific Green™, Pacific Orange™, Rhodamine Green™, Rhodamine Red™, or Texas Red®;
or adjacent R$_1$, R$_2$ moieties, and the carbon atoms to which they are attached form an optionally substituted cycloalkyl moiety;
each R$_7$ is independently H, Na, K, optionally substituted alkyl, optionally substituted aryl, or optionally substituted arylalkyl;
each n is independently 0 or 1;
each o is independently 0 or 1; and
‗‗‗ denotes a carbon-carbon single bond or double bond; and instructions for use. In another aspect, the compound of Formula I is

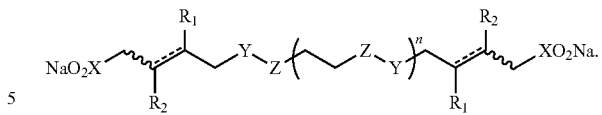

In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a kit for treating a cell proliferative disorder in a subject. The kit includes a compound of Formula II, or salt, solvate, hydrate or prodrug thereof:

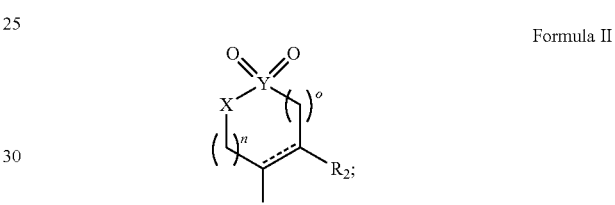

Formula II wherein, X is S or Se;
Y is S or Se;
R$_1$ is selected from H, NH$_2$, N$_3$, OAc, alkyl, or OH;
R$_2$ is selected from H, NH$_2$, N$_3$, OAc, alkyl, or OH;
n is 0, 1, 2, or 3;
is 0, 1, 2, or 3;
or R$_1$, R$_2$, and the carbon atoms to which they are attached form an optionally substituted cycloalkyl moiety or an optionally substituted aryl moiety; and
‗‗‗ denotes a carbon-carbon single bond or double bond; and instructions for use. In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a kit for treating a cell proliferative disorder in a subject. The kit includes: 1) a compound of Formula (I)-(VI), or salt, solvate, hydrate or prodrug thereof; 2) a DR5 agonist; and 3) instructions for use. In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In another aspect, the compound of Formula (I)-(VI) is

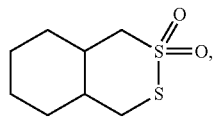 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

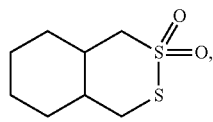 [SMILES: O=S1(=O)CC2CCCCC2CS1]

or salt, solvate, hydrate or prodrug thereof, and the DR5 agonist is TRAIL. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a kit for treating a cell proliferative disorder in a subject. The kit includes: 1) a pharmaceutical composition comprising: a) a compound of Formula (I)-(VI), or salt, solvate, hydrate or prodrug thereof; b) a DR5 agonist; and c) a pharmaceutically acceptable carrier; and 2) instructions for use. In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In another aspect, the compound of Formula (I)-(VI) is

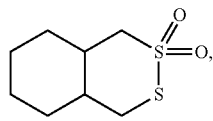 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect the DR5 agonist is TRAIL. In another aspect, the compound of Formula (I)-(VI) is

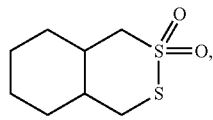 [SMILES: O=S1(=O)CC2CCCCC2CS1]

or salt, solvate, hydrate or prodrug thereof, and the DR5 agonist is TRAIL. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a kit for treating a cell proliferative disorder in a subject. The kit includes a compound of Formula III, or salt, solvate, hydrate or prodrug thereof:

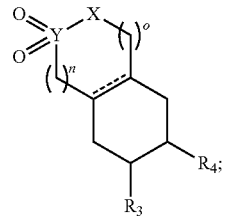

Formula III wherein, X is S or Se;
Y is S or Se;
$R_3$ is selected from H or $C_1$-$C_6$ alkoxy;
$R_4$ is selected from H or $C_1$-$C_6$ alkoxy;
n is 0, 1, 2, or 3;
is 0, 1, 2, or 3; and
--- denotes a carbon-carbon single bond or double bond;
wherein if --- is a singe bond, X and Y are both S, and n and o are each 1, then at least one of $R_3$ or $R_4$ is $C_1$-$C_6$ alkoxy; and instructions for use. In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In a further aspect, the kit includes: 1) a compound of any one of Formulae III-XIX, or salt, solvate, hydrate or prodrug thereof; 2) a DR5 agonist; and 3) instructions for use. In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer.

In another aspect, the invention provides a kit for treating a cell proliferative disorder in a subject. The kit includes a pharmaceutical composition comprising a therapeutically effective amount of a compound of any one of Formulae III-XIX, or salt, solvate, hydrate or prodrug thereof; and a pharmaceutically acceptable carrier; and instructions for use. In another aspect, the kit includes: 1) a pharmaceutical composition comprising: a) a compound of any one of Formulae III-XIX, or salt, solvate, hydrate or prodrug thereof; b) a DR5 agonist; and c) a pharmaceutically acceptable carrier; and 2) instructions for use. In certain embodiments, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer.

In another aspect, the invention provides a method of inhibiting EGFR, HER2, and/or HER3. The method includes administering a therapeutically effective amount of a compound of Formula I, or salt, solvate, hydrate or prodrug thereof:

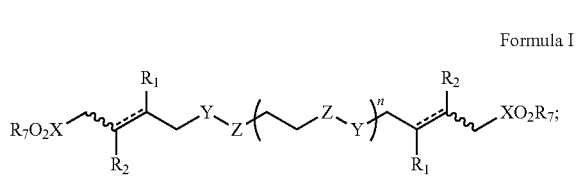

Formula I wherein, each X is independently S or Se;
each Y is independently S, $SO_2$, or Se;
each Z is independently S, $SO_2$, or Se;
each $R_1$ is independently selected from H, $NH_2$, $N_3$, OH, oxo, OAc, NH—$R_3$,

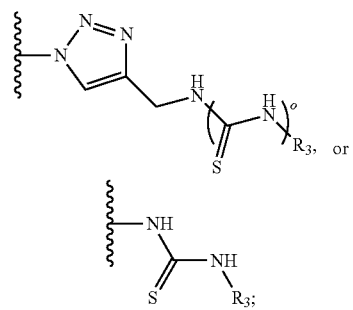

each $R_2$ is independently selected from H, $NH_2$, $N_3$, OH, oxo, OAc, NH—$R_3$,

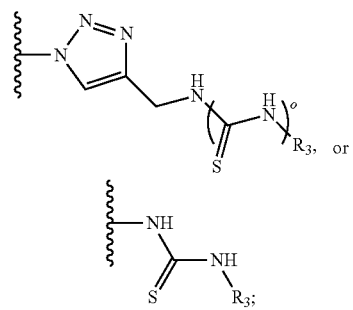

each $R_3$ is independently selected from biotin, fluorescein, AlexaFluor® dyes, BODIPY®, Cascade Blue®, coumarins, Oregon Green®, Pacific Blue™, Pacific Green™, Pacific Orange™, Rhodamine Green™, Rhodamine Red™, or Texas Red®;
or adjacent $R_1$, $R_2$ moieties, and the carbon atoms to which they are attached form an optionally substituted cycloalkyl moiety;
each $R_7$ is independently H, Na, K, optionally substituted alkyl, optionally substituted aryl, or optionally substituted arylalkyl;
each n is independently 0 or 1;
each o is independently 0 or 1; and ═══ denotes a carbon-carbon single bond or double bond. In another aspect, the compound of Formula I is

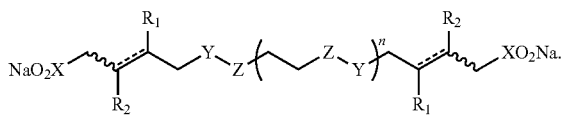

In another aspect, the compound inhibits or is capable of inhibiting at least two of EGFR, HER2, and HER3. In another aspect, the compound inhibits or is capable of inhibiting all three of EGFR, HER2, and HER3.

In another aspect, the invention provides a method of inhibiting EGFR, HER2, and/or HER3. The method includes administering a therapeutically effective amount of a compound of Formula II, or salt, solvate, hydrate or prodrug thereof.

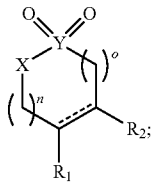

Formula II wherein, X is S or Se;
Y is S or Se;
$R_1$ is selected from H, $NH_2$, $N_3$, OAc, alkyl, or OH;
$R_2$ is selected from H, $NH_2$, $N_3$, OAc, alkyl, or OH;
n is 0, 1, 2, or 3;
is 0, 1, 2, or 3;
or $R_1$, $R_2$, and the carbon atoms to which they are attached form an optionally substituted cycloalkyl moiety or an optionally substituted aryl moiety; and
═══ denotes a carbon-carbon single bond or double bond. In another aspect, the compound inhibits or is capable of inhibiting at least two of EGFR, HER2, and HER3. In another aspect, the compound inhibits or is capable of inhibiting all three of EGFR, HER2, and HER3.

In another aspect, the invention provides a method of inhibiting EGFR, HER2, and/or HER3. The method includes administering a therapeutically effective amount of a compound of Formula (I)-(VI), or salt, solvate, hydrate or prodrug thereof; and a therapeutically effective amount of DR5 agonist. In another aspect, the compound of Formula (I)-(VI), or salt, solvate, hydrate or prodrug thereof, and the DR5 agonist are administered sequentially. In another aspect, the compound of Formula (I)-(VI), or salt, solvate, hydrate or prodrug thereof, and the DR5 agonist are administered simultaneously. In another aspect, the inhibition is in vitro. In another aspect, the inhibition occurs in a subject. In another aspect, the compound of Formula (I)-(VI) is

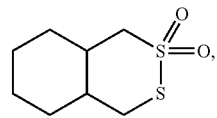 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

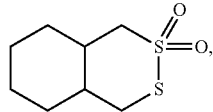 [SMILES: O=S1(=O)CC2CCCCC2CS1]

or salt, solvate, hydrate or prodrug thereof, and the DR5 agonist is TRAIL. In another aspect, the compound inhibits or is capable of inhibiting at least two of EGFR, HER2, and HER3. In another aspect, the compound inhibits or is capable of inhibiting all three of EGFR, HER2, and HER3.

In another aspect, the invention provides a method of inhibiting EGFR, HER2, and/or HER3. The method includes administering to a subject in need thereof a pharmaceutical composition comprising: 1) a therapeutically effective amount of a compound of (I)-(VI), or salt, solvate, hydrate or prodrug thereof, 2) a therapeutically effective amount of DR5 agonist; and 3) a pharmaceutically acceptable carrier. In another aspect, the compound of Formula (I)-(VI) is

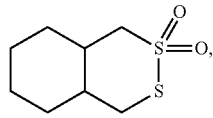 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

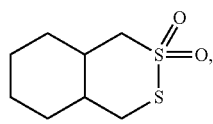 [SMILES: O=S1(=O)CC2CCCCC2CS1]

or salt, solvate, hydrate or prodrug thereof, and the DR5 agonist is TRAIL. In another aspect, the compound inhibits or is capable of inhibiting at least two of EGFR, HER2, and HER3. In another aspect, the compound inhibits or is capable of inhibiting all three of EGFR, HER2, and HER3.

In another aspect, the invention provides a method of inhibiting EGFR, HER2, and/or HER3. The method includes administering a therapeutically effective amount of a compound of Formula III, or salt, solvate, hydrate or prodrug thereof.

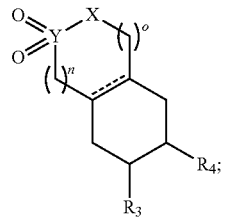

Formula III wherein, X is S or Se;
Y is S or Se;
$R_3$ is selected from H or $C_1$-$C_6$ alkoxy;
$R_4$ is selected from H or $C_1$-$C_6$ alkoxy;
n is 0, 1, 2, or 3;
is 0, 1, 2, or 3; and
--- denotes a carbon-carbon single bond or double bond;
wherein if --- is a single bond, X and Y are both S, and n and o are each 1, then at least one of $R_3$ or $R_4$ is $C_1$-$C_6$ alkoxy. In another aspect, the compound inhibits or is capable of inhibiting at least two of EGFR, HER2, and HER3. In another aspect, the compound inhibits or is capable of inhibiting all three of EGFR, HER2, and HER3. In another aspect, the method includes administering a therapeutically effective amount of a compound of any one of Formulae III-XIX, or salt, solvate, hydrate or prodrug thereof; and a therapeutically effective amount of DR5 agonist. In another aspect, the compound of Formulae III-XIX, or salt, solvate, hydrate or prodrug thereof, and the DR5 agonist are administered sequentially. In another aspect, the compound of Formulae III-XIX, or salt, solvate, hydrate or prodrug thereof, and the DR5 agonist are administered simultaneously.

In another aspect, the invention provides a method of inhibiting EGFR, HER2, and/or HER3. The method includes administering to a subject in need thereof a pharmaceutical composition comprising a compound of any one of Formulae III-XIX, or salt, solvate, hydrate or prodrug thereof; and a pharmaceutically acceptable carrier. In another aspect, the method includes administering to a subject in need thereof a pharmaceutical composition comprising: 1) a therapeutically effective amount of a compound of any one of Formulae III-XIX, or salt, solvate, hydrate or prodrug thereof; 2) a therapeutically effective amount of DR5 agonist; and 3) a pharmaceutically acceptable carrier.

In another aspect, the compound of Formula (I)-(VI) is:
sodium (2R,3R)-2,3-diacetoxy-4-((2-(((2R,3R)-2,3-diacetoxy-4-sulfinatobutyl)disulfanyl)ethyl)disulfanyl)butane-1-sulfinate;
sodium (2S,3S)-2,3-diacetoxy-4-((2-(((2S,3S)-2,3-diacetoxy-4-sulfinatobutyl)disulfanyl)ethyl)disulfanyl)butane-1-sulfinate;
sodium (2S,3R)-2,3-diacetoxy-4-((2-(((2R,3S)-2,3-diacetoxy-4-sulfinatobutyl)disulfanyl)ethyl)disulfanyl)butane-1-sulfinate;
sodium (2R,3S)-2,3-diacetoxy-4-((2-(((2S,3R)-2,3-diacetoxy-4-sulfinatobutyl)disulfanyl)ethyl)disulfanyl)butane-1-sulfinate;
sodium 4-(2-(4-sulfinatobutylsulfonylthio)ethylthiosulfonyl)butane-1-sulfinate;
sodium 4-(2-(4-sulfinatobutylthiosulfonyl)ethylsulfonylthio)butane-1-sulfinate sodium 4-(2-(4-sulfinatobutylsulfonylsulfonyl)ethylsulfonylsulfonyl)butane-1-sulfinate;
sodium 4,4'-diselanediyldibutane-1-seleninate;
sodium 5,10-dithia-6,9-diselenatetradecane-1,14-disulfinate;
sodium 6,9-dithia-5,10-diselenatetradecane-1,14-diseleninate;
sodium 4,4'-(ethane-1,2-diylbis(diselanediyl))dibutane-1-seleninate;
sodium (2Z,2'Z)-4,4'-disulfanediyldibut-2-ene-1-sulfinate;
sodium (2E,2'E)-5,5'-disulfanediyldipent-2-ene-1-sulfinate;
sodium (2R,2'R,3R,3'R)-4,4'-disulfanediylbis(2,3-dihydroxybutane-1-sulfinate);
sodium (2S,2'S,3S,3'S)-4,4'-disulfanediylbis(2,3-dihydroxybutane-1-sulfinate);
sodium (2R,2'R,3R,3'R)-4,4'-disulfanediylbis(2,3-diaminobutane-1-sulfinate);
sodium (2S,2'S,3S,3'S)-4,4'-disulfanediylbis(2,3-diaminobutane-1-sulfinate);
sodium (2R,2'R,3R,3'R)-4,4'-disulfanediylbis(2,3-diazidobutane-1-sulfinate);
sodium (2S,2'S,3S,3'S)-4,4'-disulfanediylbis(2,3-diazidobutane-1-sulfinate); sodium 4,4'-disulfanediylbis(2,3-dioxobutane-1-sulfinate);
sodium (3R,3'R)-4,4'-disulfanediylbis(3-aminobutane-1-sulfinate);
sodium (3S,3'S)-4,4'-disulfanediylbis(3-aminobutane-1-sulfinate);
sodium (3R,3'R)-4,4'-disulfanediylbis(3-azidobutane-1-sulfinate);
sodium (3S,3'S)-4,4'-disulfanediylbis(3-azidobutane-1-sulfinate);
sodium (2R,2'R)-4,4'-disulfanediylbis(2-aminobutane-1-sulfinate);
sodium (2S,2'S)-4,4'-disulfanediylbis(2-aminobutane-1-sulfinate);
sodium (2R,2'R)-4,4'-disulfanediylbis(2-azidobutane-1-sulfinate);
sodium (2S,2'S)-4,4'-disulfanediylbis(2-azidobutane-1-sulfinate);
sodium (1R,1'R,2R,2'R,3R,3'R,4S,4'S)-3,3'-disulfanediylbis(methylene)bis(bicyclo[2.2.1]heptane-3,2-diyl)dimethanesulfinate;
sodium (1R,1'R,2S,2'S,3S,3'S,4S,4'S)-3,3'-disulfanediylbis(methylene)bis(bicyclo[2.2.]heptane-3,2-diyl)dimethanesulfinate;
sodium (2R,2'R,3R,3'R)-4,4'-(ethane-1,2-diylbis(disulfanediyl))bis(2,3-dihydroxybutane-1-sulfinate);
sodium (2S,2'S,3S,3'S)-4,4'-(ethane-1,2-diylbis(disulfanediyl))bis(2,3-dihydroxybutane-1-sulfinate);
sodium (2R,2'R,3R,3'R)-4,4'-(ethane-1,2-diylbis(disulfanediyl))bis(2,3-diaminobutane-1-sulfinate);
(2S,2'S,3S,3'S)-4,4'-(ethane-1,2-diylbis(disulfanediyl))bis(2,3-diaminobutane-1-sulfinate);
(2R,2'R,3R,3'R)-4,4'-(ethane-1,2-diylbis(disulfanediyl))bis(2,3-diazidobutane-1-sulfinate);
sodium (2S,2'S,3S,3'S)-4,4'-(ethane-1,2-diylbis(disulfanediyl))bis(2,3-diazidobutane-1-sulfinate);
sodium 4,4'-(ethane-1,2-diylbis(disulfanediyl))bis(2,3-dioxobutane-1-sulfinate); sodium (3R,3'R)-4,4'-(ethane-1,2-diylbis(disulfanediyl))bis(3-aminobutane-1-sulfinate);
sodium (3S,3'S)-4,4'-(ethane-1,2-diylbis(disulfanediyl))bis(3-aminobutane-1-sulfinate);
sodium (3R,3'R)-4,4'-(ethane-1,2-diylbis(disulfanediyl))bis(3-azidobutane-1-sulfinate);
sodium (3S,3'S)-4,4'-(ethane-1,2-diylbis(disulfanediyl))bis(3-azidobutane-1-sulfinate);
sodium (2R,2'R)-4,4'-(ethane-1,2-diylbis(disulfanediyl))bis(2-aminobutane-1-sulfinate);
sodium (2S,2'S)-4,4'-(ethane-1,2-diylbis(disulfanediyl))bis(2-aminobutane-1-sulfinate);
sodium (2R,2'R)-4,4'-(ethane-1,2-diylbis(disulfanediyl))bis(2-azidobutane-1-sulfinate);
sodium (2S,2'S)-4,4'-(ethane-1,2-diylbis(disulfanediyl))bis(2-azidobutane-1-sulfinate);
sodium (1R,1'R,2R,2'R,3R,3'R,4S,4'S)-3,3'-(ethane-1,2-diylbis(disulfanediyl))bis(methylene)bis(bicyclo[2.2.1]heptane-3,2-diyl)dimethanesulfinate;
sodium (1R,1'R,2S,2'S,3S,3'S,4S,4'S)-3,3'-(ethane-1,2-diylbis(disulfanediyl))bis(methylene)bis(bicyclo[2.2.1]heptane-3,2-diyl)dimethanesulfinate;
1,2-diselenane-1,1-dioxide;
3,6-dihydro-1,2-dithiine-1,1-dioxide;
trans-1,2-dithiane-4,5-diol-1,1-dioxide;
trans-1,2-dithiane-4,5-diamino-1,1-dioxide;
trans-1,2-dithiane-4,5-diazido-1,1-dioxide;
cis-1,2-dithiane-4,5-diol-1,1-dioxide;
cis-1,2-dithiane-4,5-diamino-1,1-dioxide;
cis-1,2-dithiane-4,5-diazido-1,1-dioxide;
1,2-dithiane-4,5-dione-1,1-dioxide;
1,2-dithiane-(4R,5S-diacetoxy)-1,1-dioxide;
1,2-dithiane-(4S,5R-diacetoxy)-1,1-dioxide;
1,2-dithiane-(4R,5R-diacetoxy)-1,1-dioxide;
1,2-dithiane-(4S,5S-diacetoxy)-1,1-dioxide;
1,2-dithiane-(4R,5S-dihydroxy)-1,1-dioxide;
1,2-dithiane-(4S,5R-dihydroxy)-1,1-dioxide;
1,2-dithiane-(4R,5R-dihydroxy)-1,1-dioxide;
1,2-dithiane-(4S,5S-dihydroxy)-1,1-dioxide;
1,2-dithiane-4-amino-1,1-dioxide;
1,2-dithiane-4-azido-1,1-dioxide;
1,2-dithiane-5-amino-1,1-dioxide;
1,2-dithiane-5-azido-1,1-dioxide;

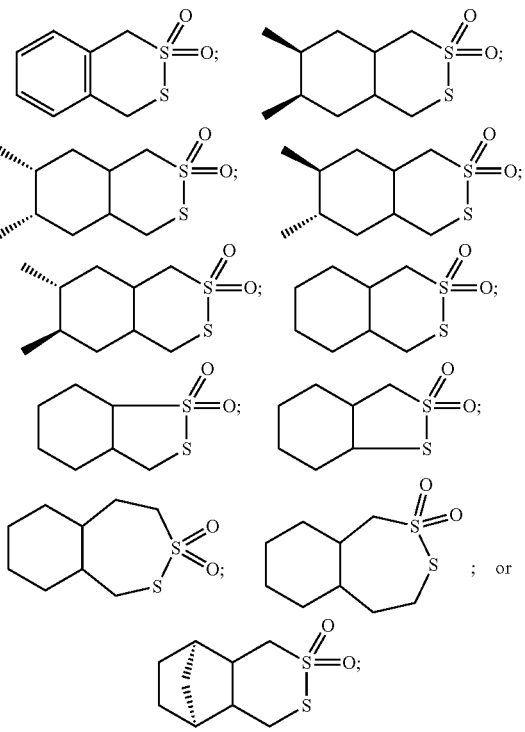

or salt, solvate, hydrate or prodrug thereof.

In another aspect, the invention provides a compound of Formula III, or salt, hydrate, solvate, or prodrug thereof:
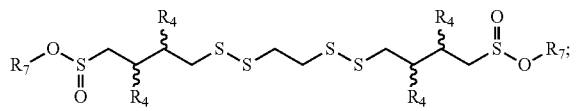
wherein, each R$_4$ is independently selected from
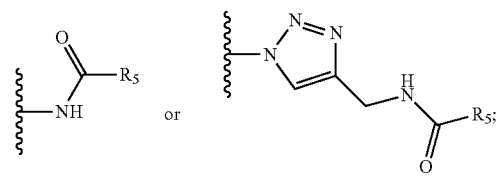
each R$_5$ is independently selected from the group consisting of:
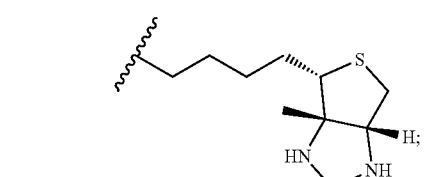
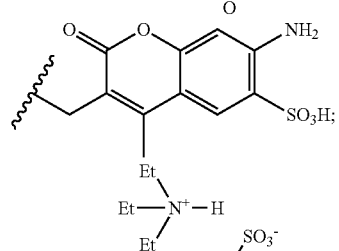
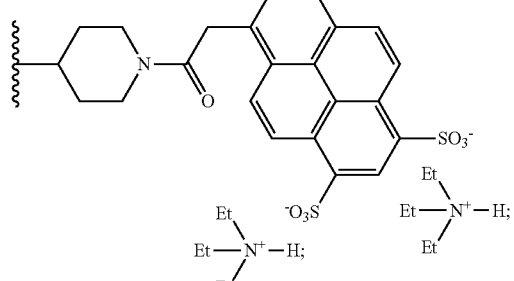
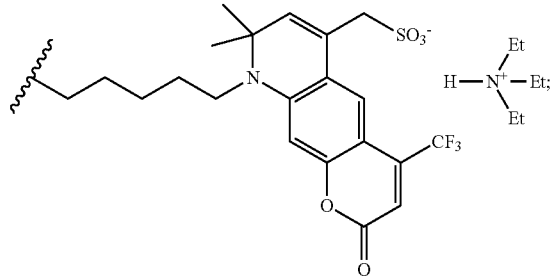
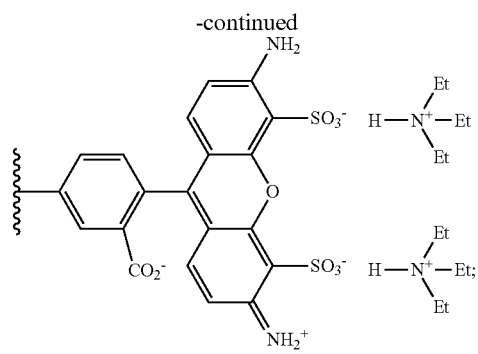
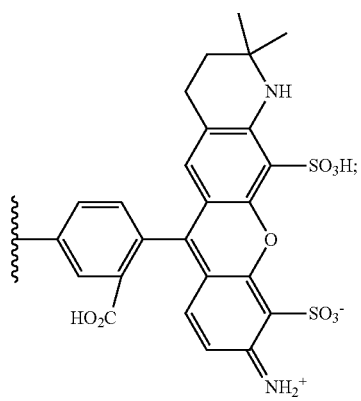
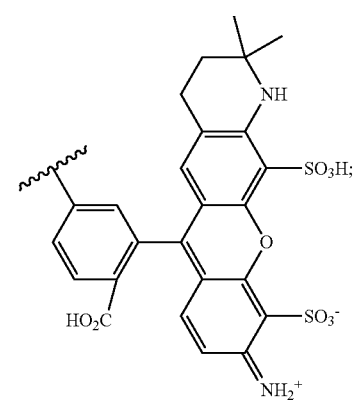
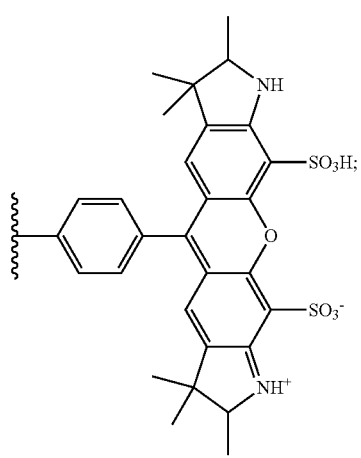

35
-continued
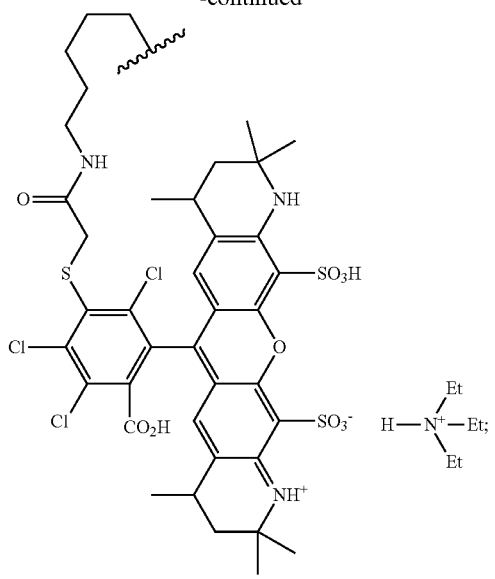
36
-continued
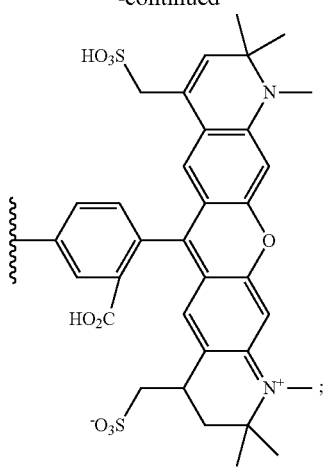
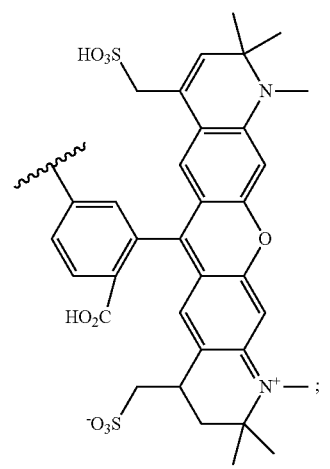
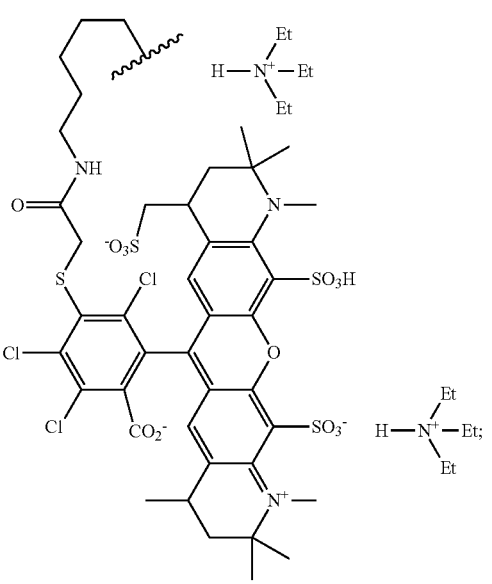

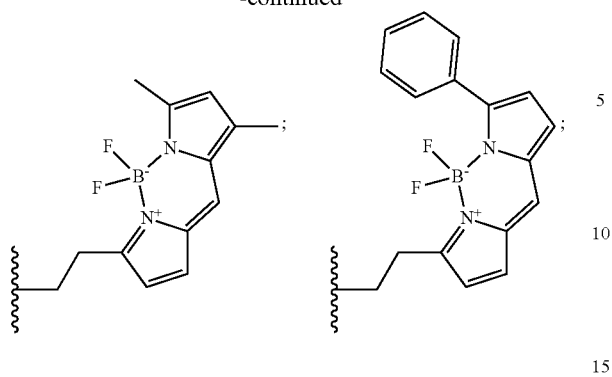
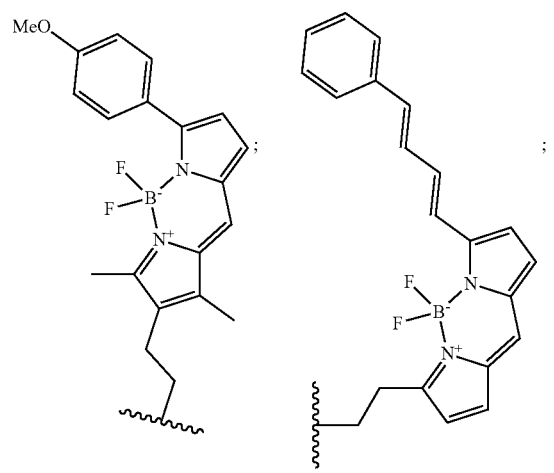
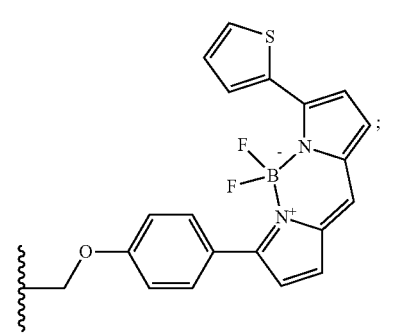
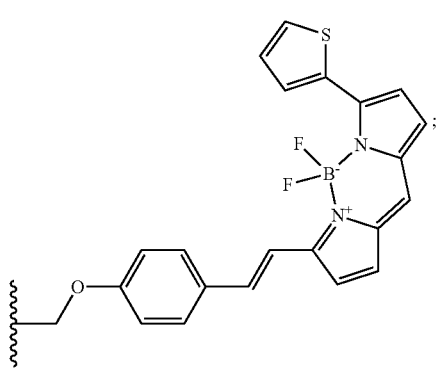
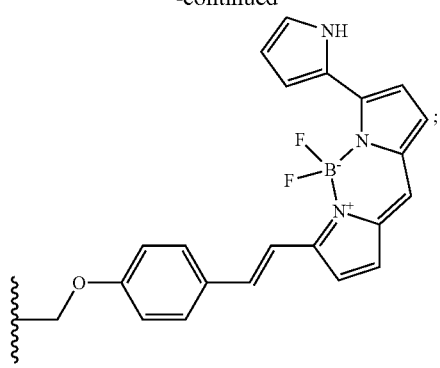
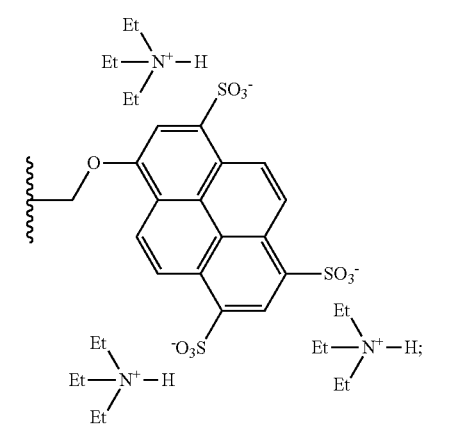
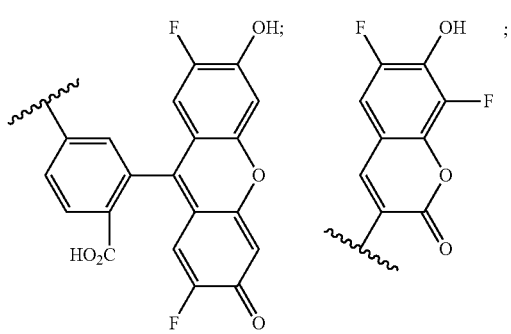
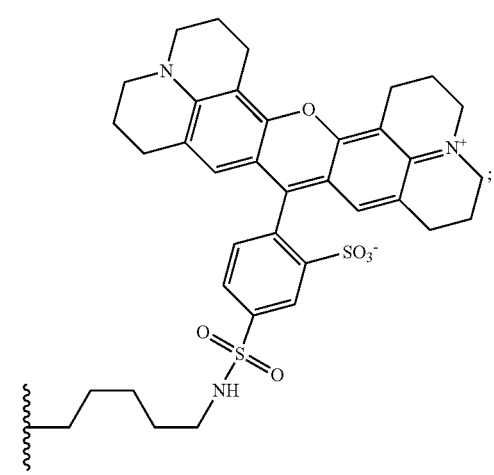

-continued

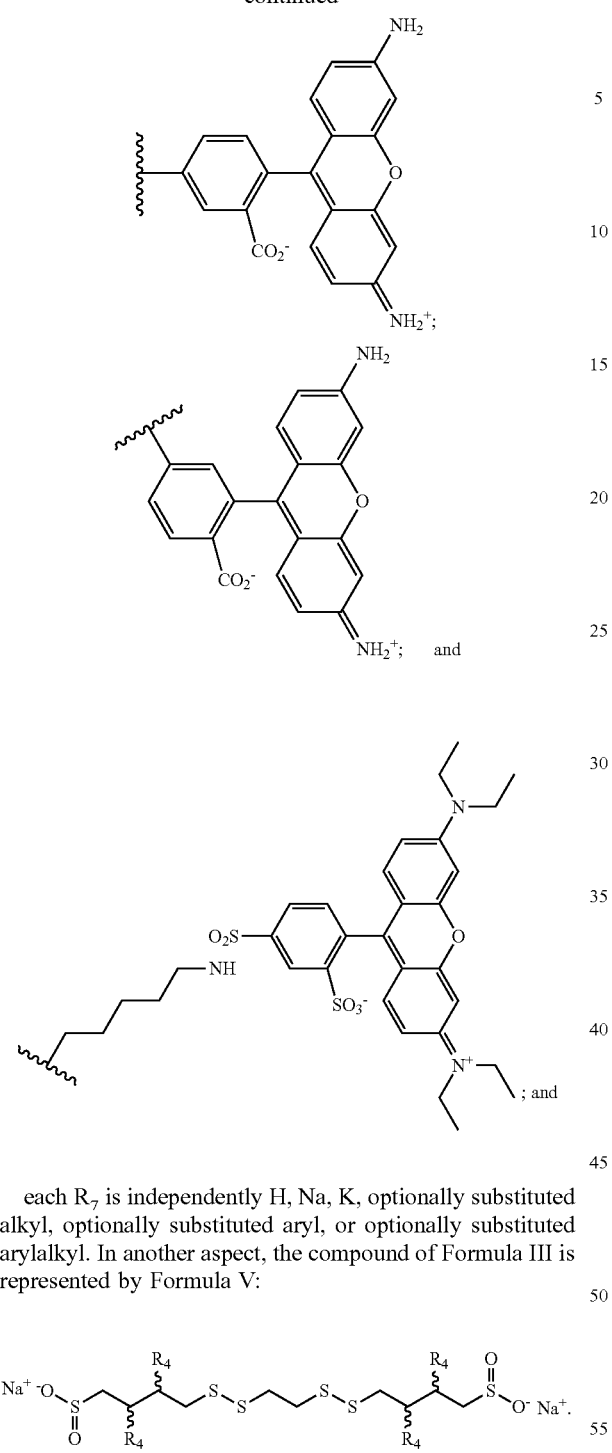

each $R_7$ is independently H, Na, K, optionally substituted alkyl, optionally substituted aryl, or optionally substituted arylalkyl. In another aspect, the compound of Formula III is represented by Formula V:

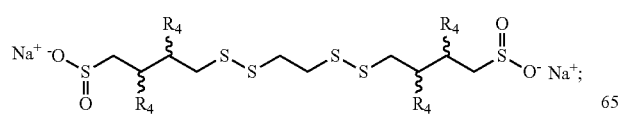

In another aspect, the invention provides a compound of Formula V, or salt, hydrate, solvate, or prodrug thereof:

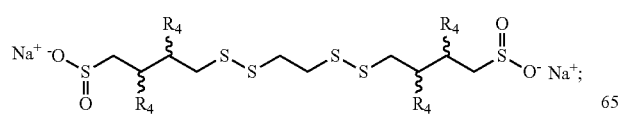

wherein the compound is selected from the group consisting of:

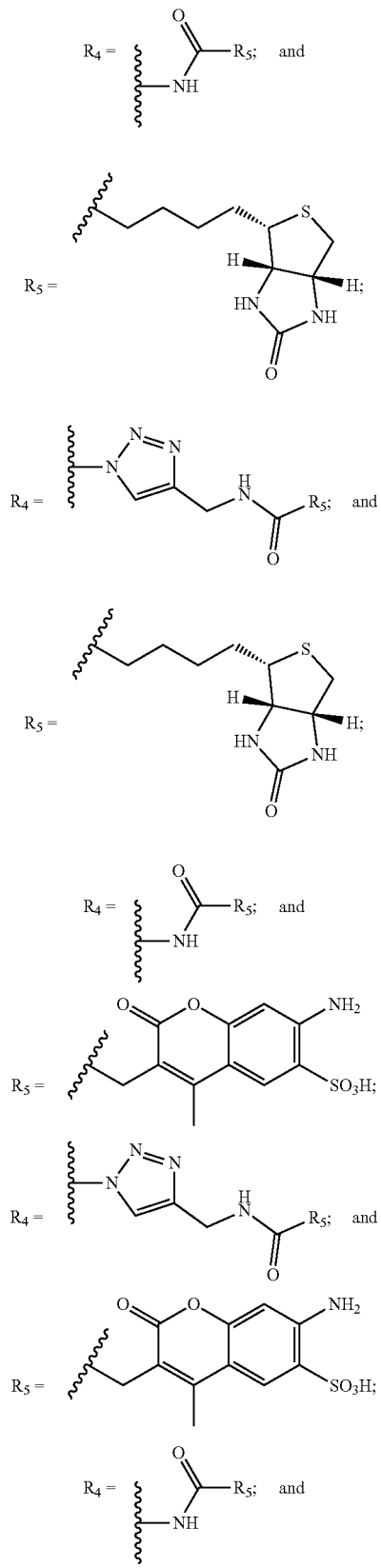

-continued
$R_5 =$ 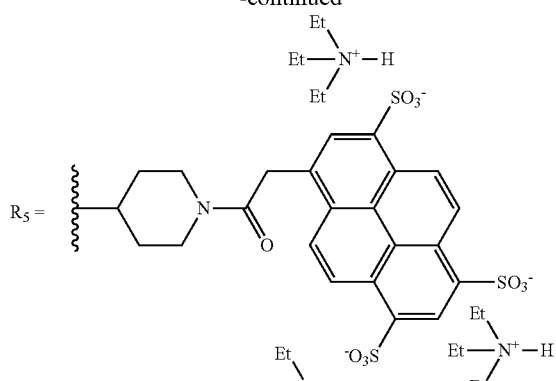
$R_4 =$ 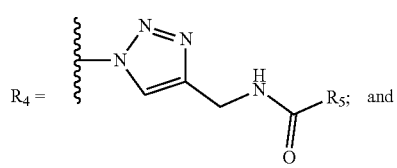
$R_5 =$ 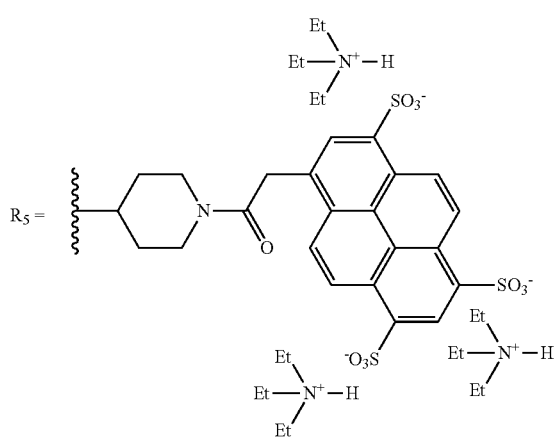
$R_4 =$ 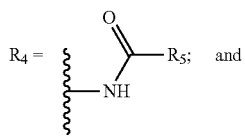
$R_5 =$ 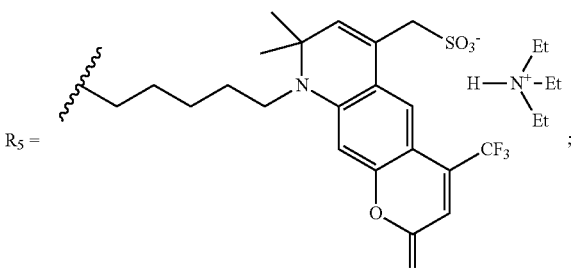
$R_4 =$ 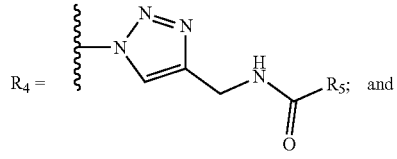
-continued
$R_5 =$ 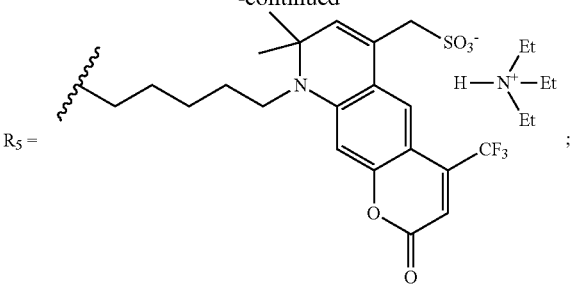
$R_4 =$ 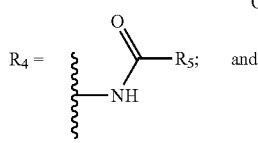
$R_5 =$ 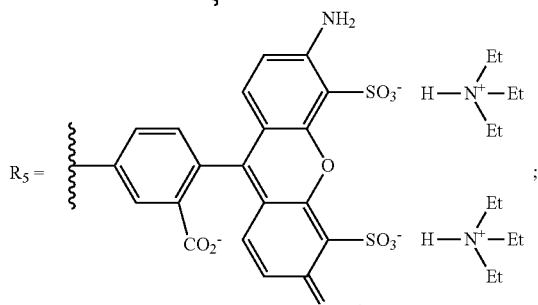
$R_4 =$ 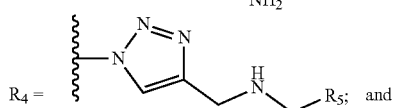
$R_5 =$ 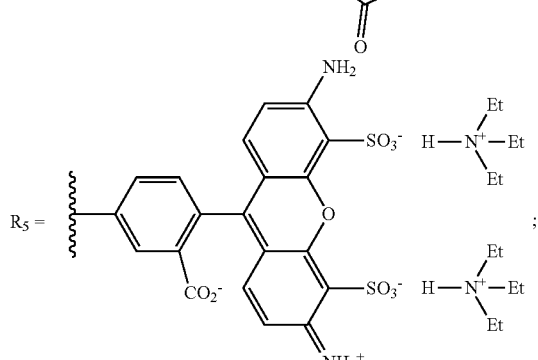
$R_4 =$ 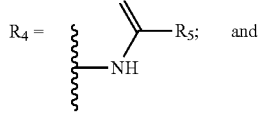
$R_5 =$ 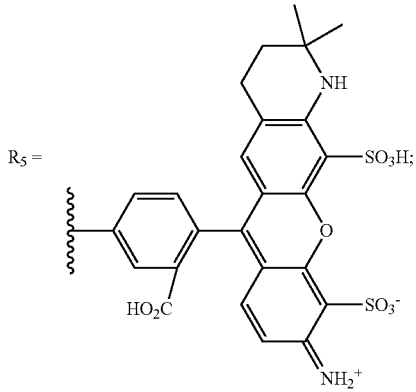

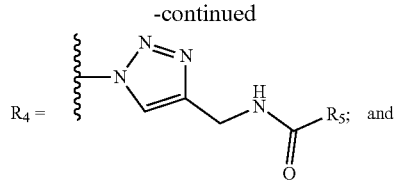
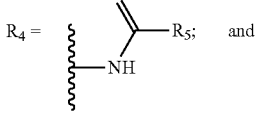
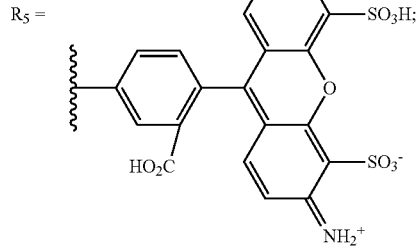
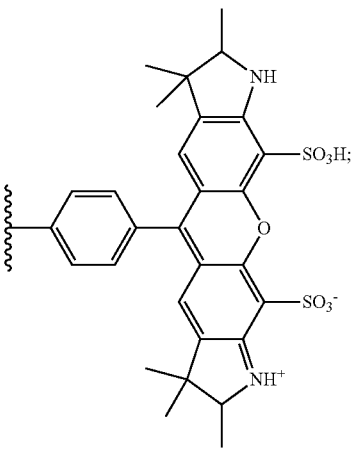
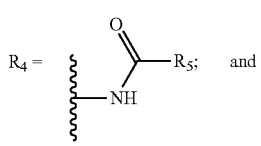
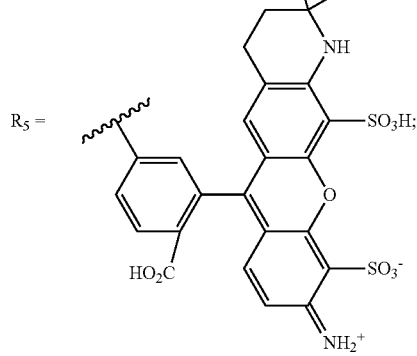
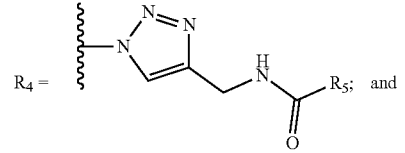
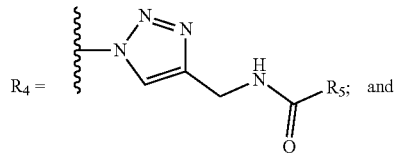
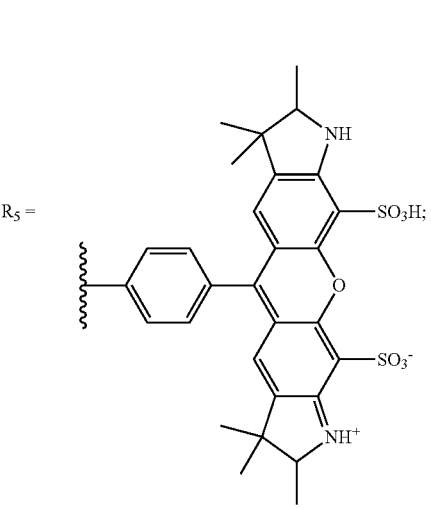
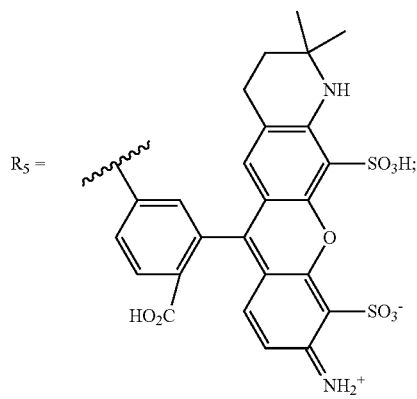
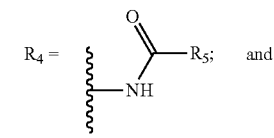

45
-continued
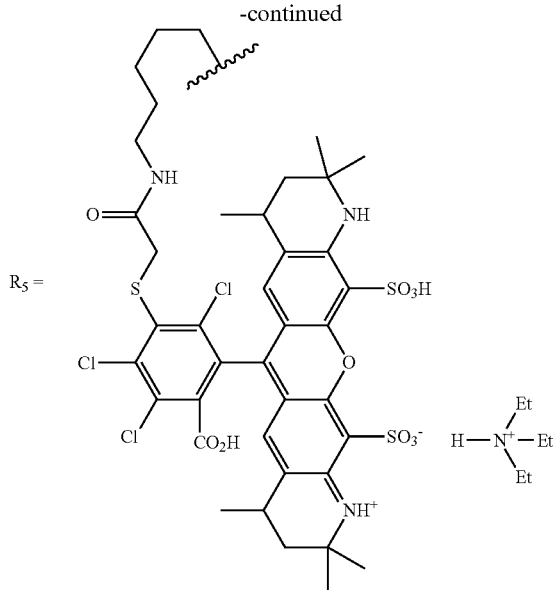
$R_5 =$
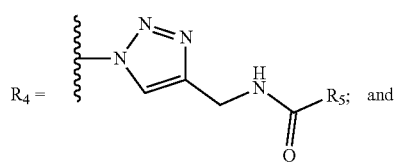
$R_4 =$ ; and
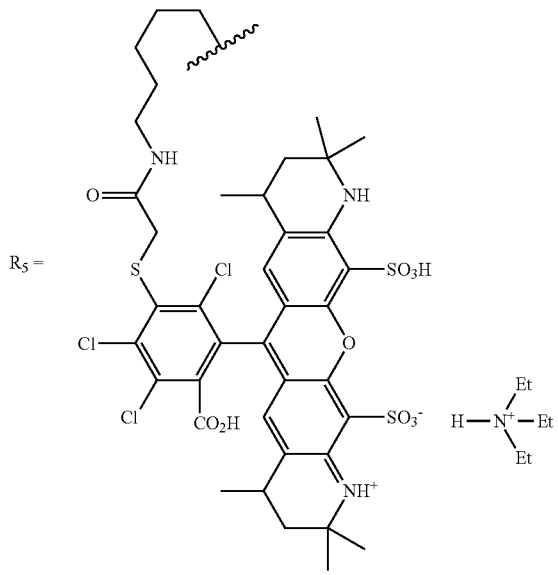
$R_5 =$
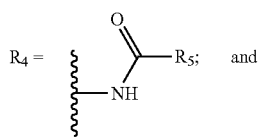
$R_4 =$ ; and
46
-continued
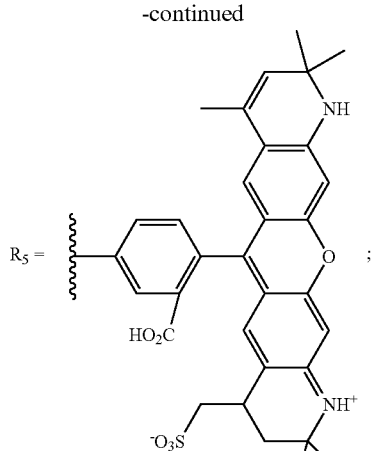
$R_5 =$ ;
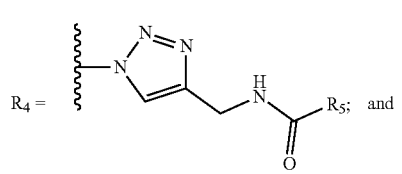
$R_4 =$ ; and
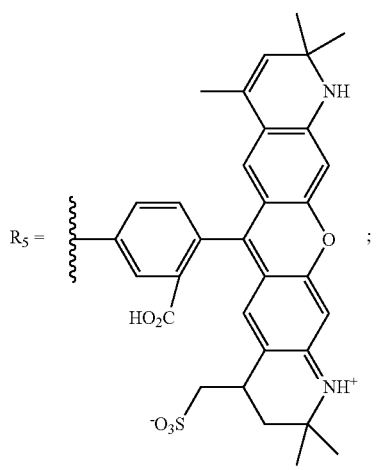
$R_5 =$ ;
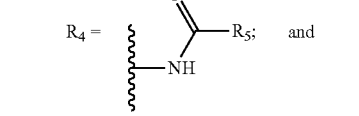
$R_4 =$ ; and
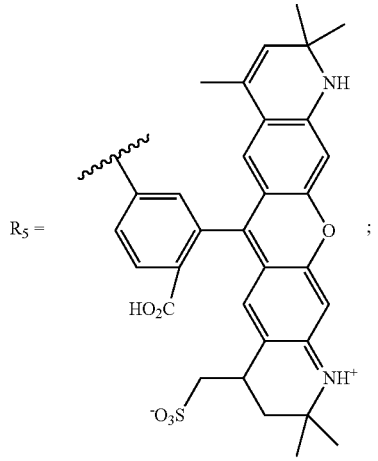
$R_5 =$ ;

-continued
R<sub>4</sub> = 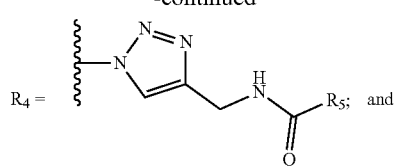 ; and
R<sub>5</sub> = 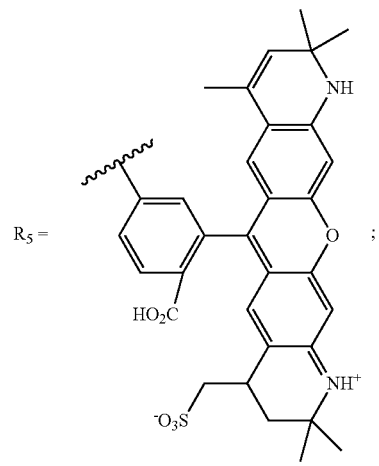 ;
R<sub>4</sub> = 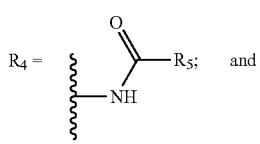 ; and
R<sub>5</sub> = 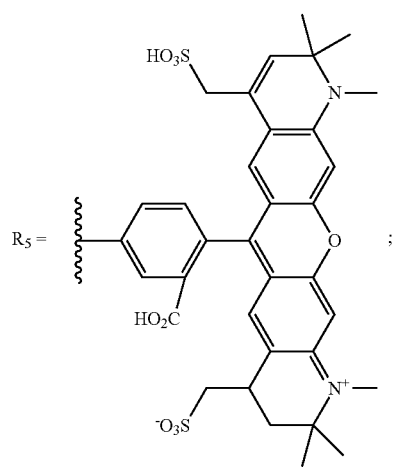 ;
R<sub>4</sub> = 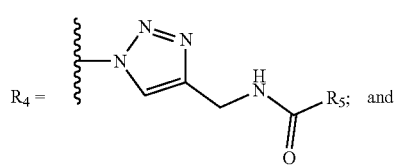 ; and
-continued
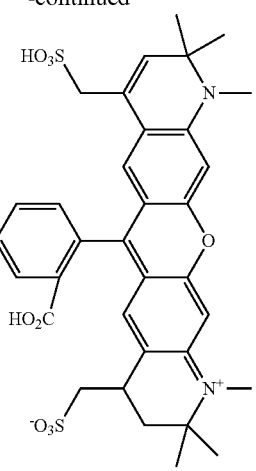
R<sub>5</sub> = ;
R<sub>4</sub> = 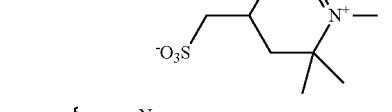 ; and
R<sub>5</sub> = 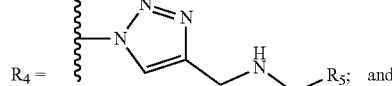 ;
R<sub>4</sub> = 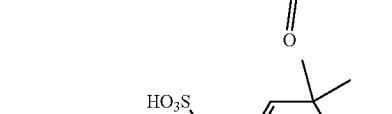 ; and
R<sub>5</sub> = 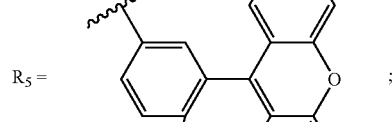 ;

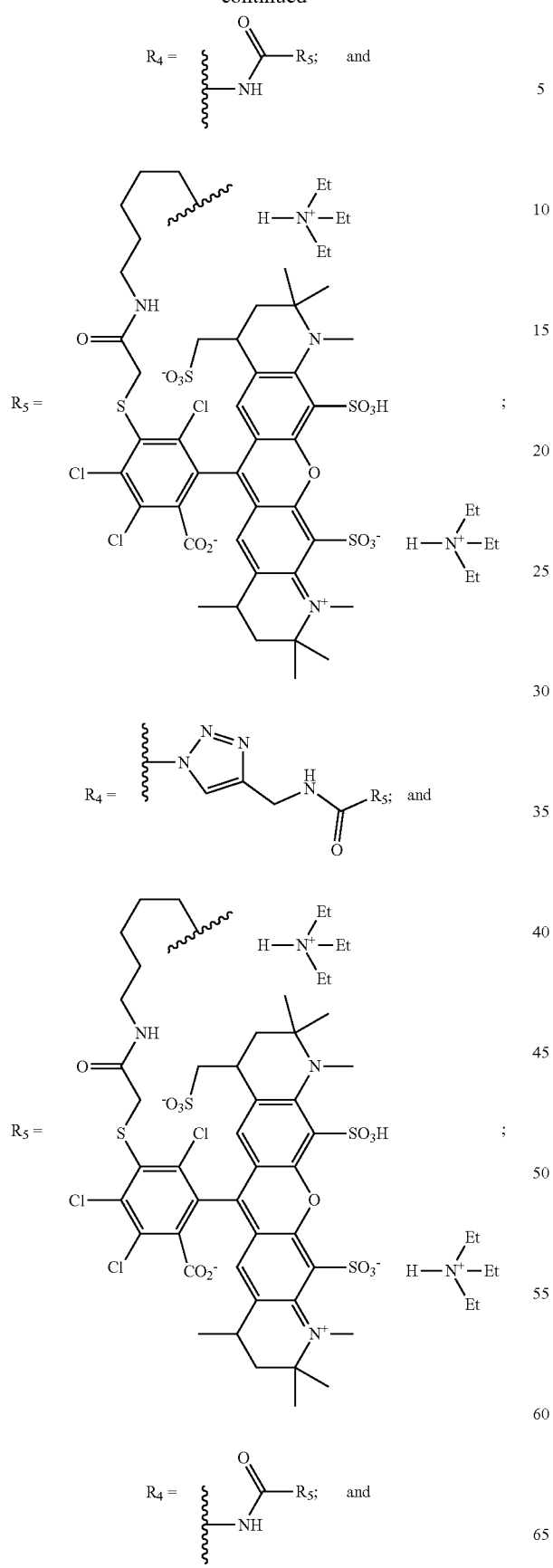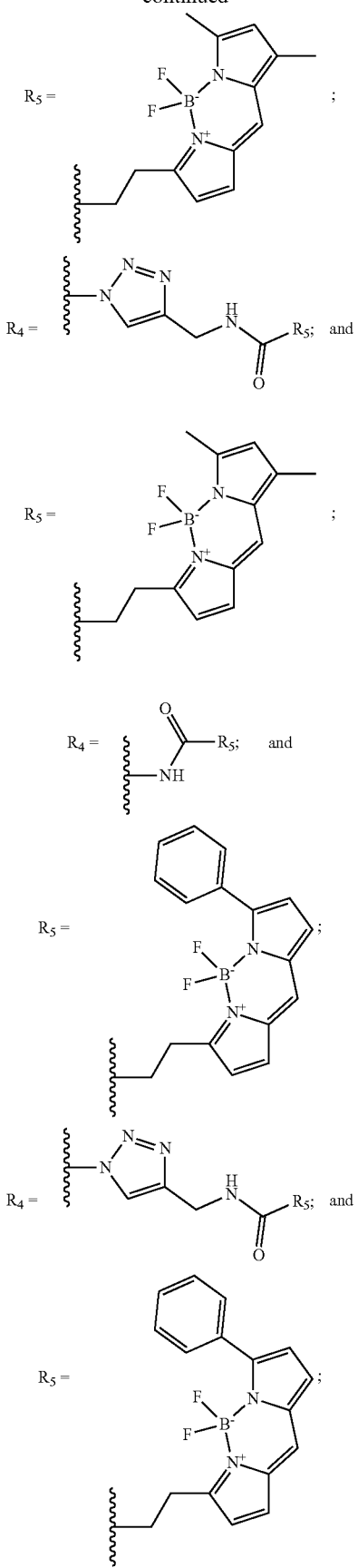

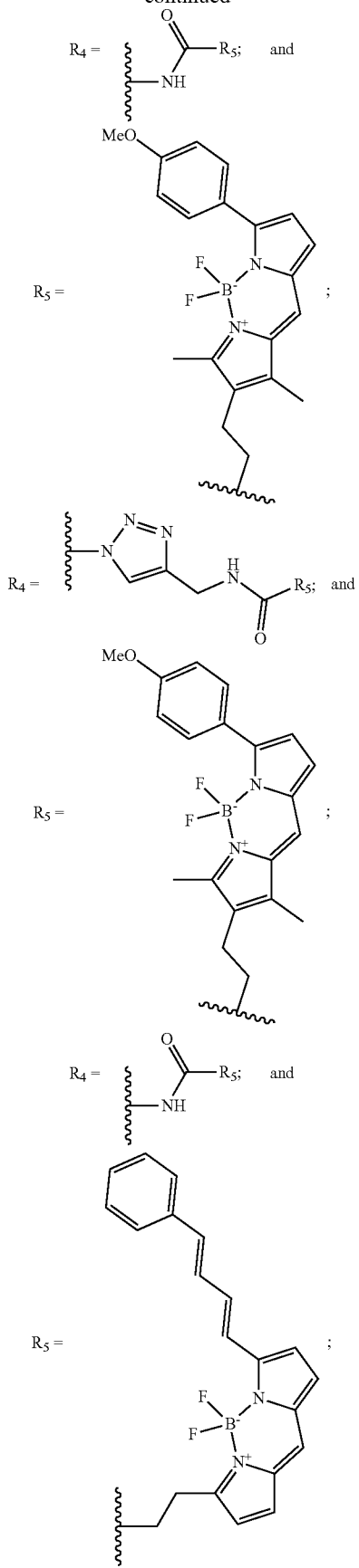
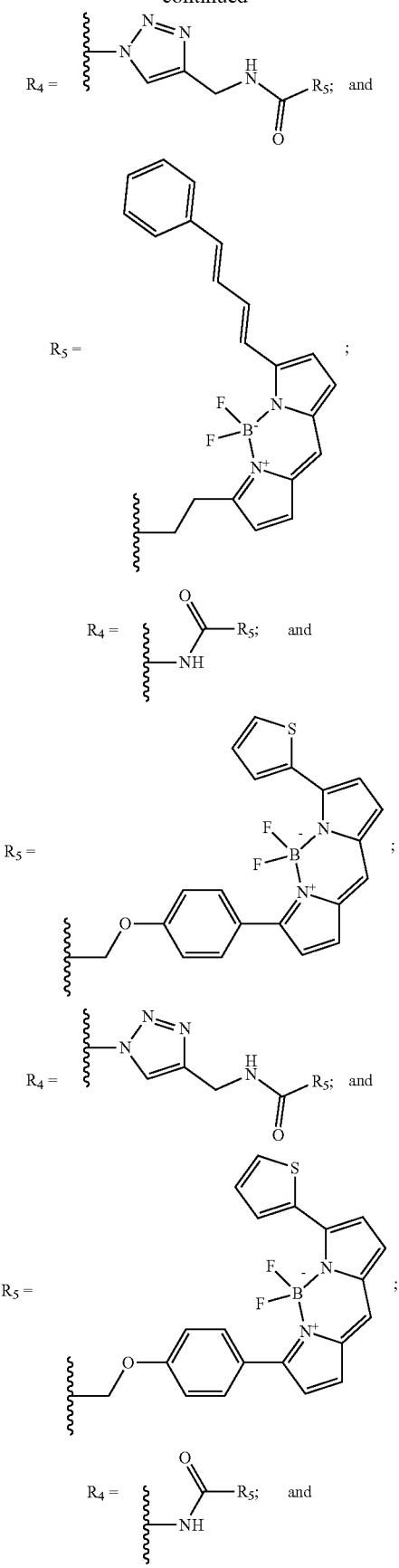

R5 = 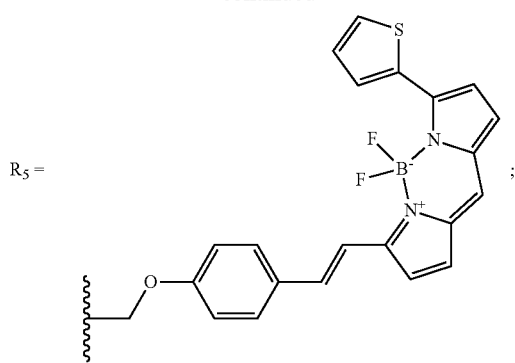;
R4 = 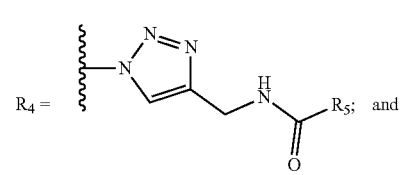; and
R5 = 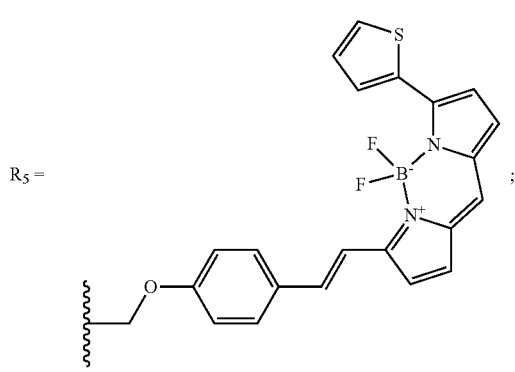;
R4 = 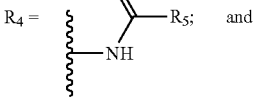; and
R5 = 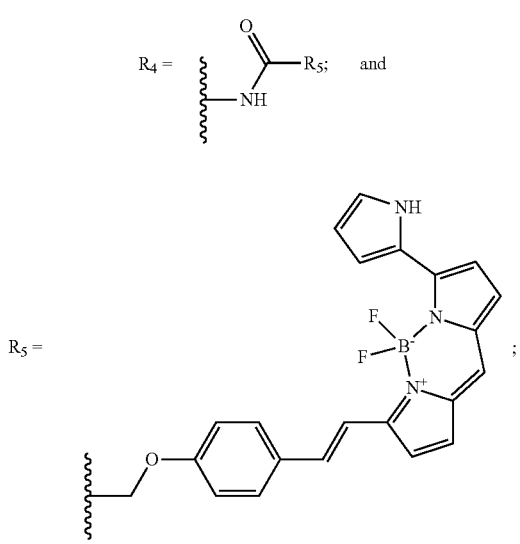;
R4 = 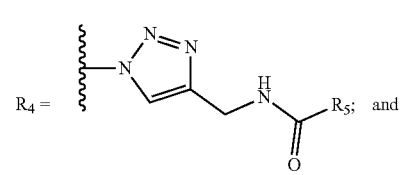; and
R5 = 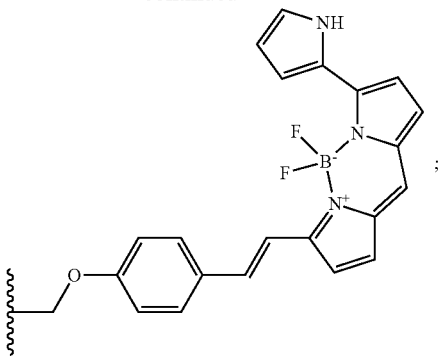;
R4 = 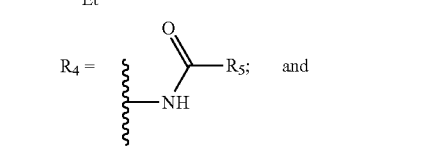; and
R5 = 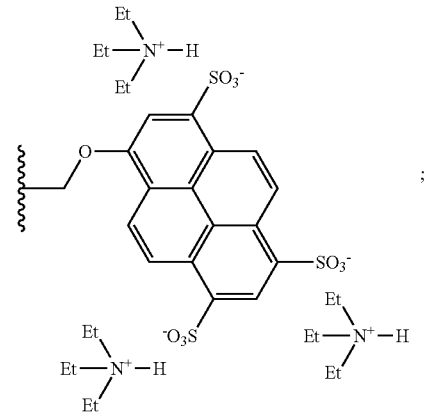;
R4 = 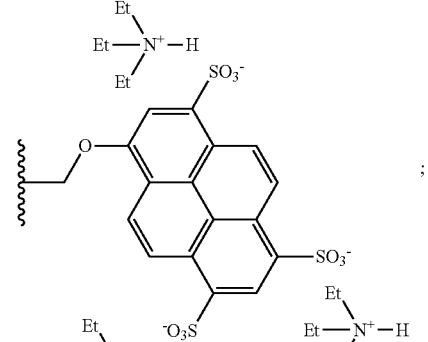; and
R5 = 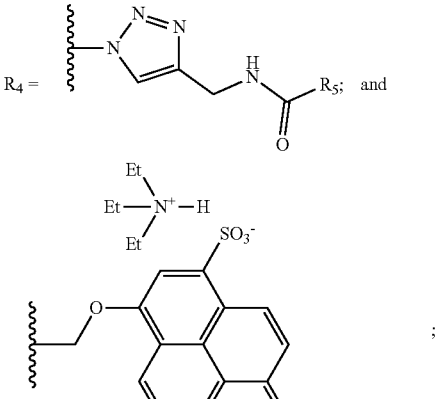;
R4 = 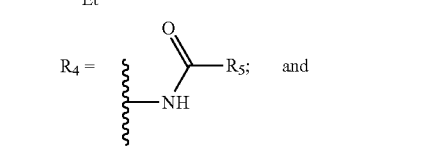; and

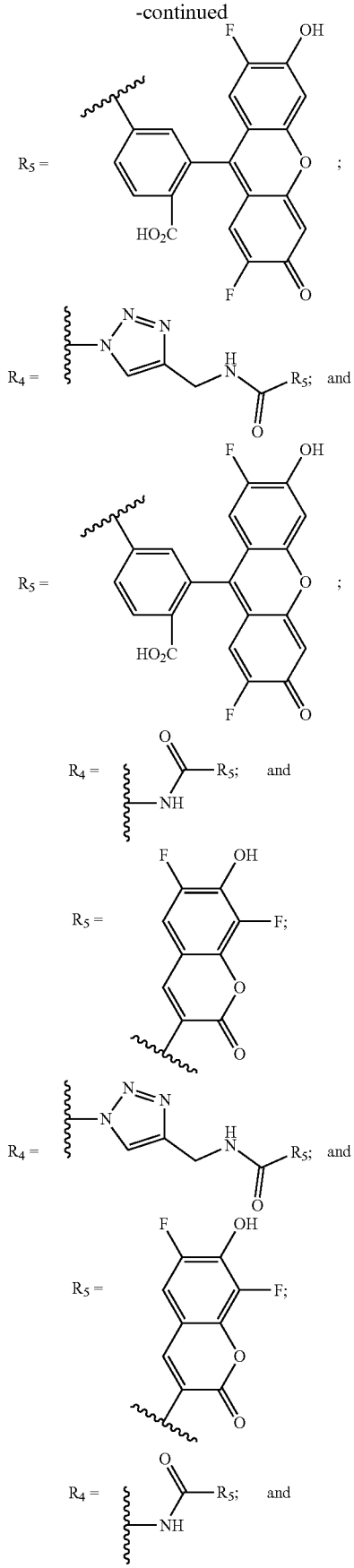
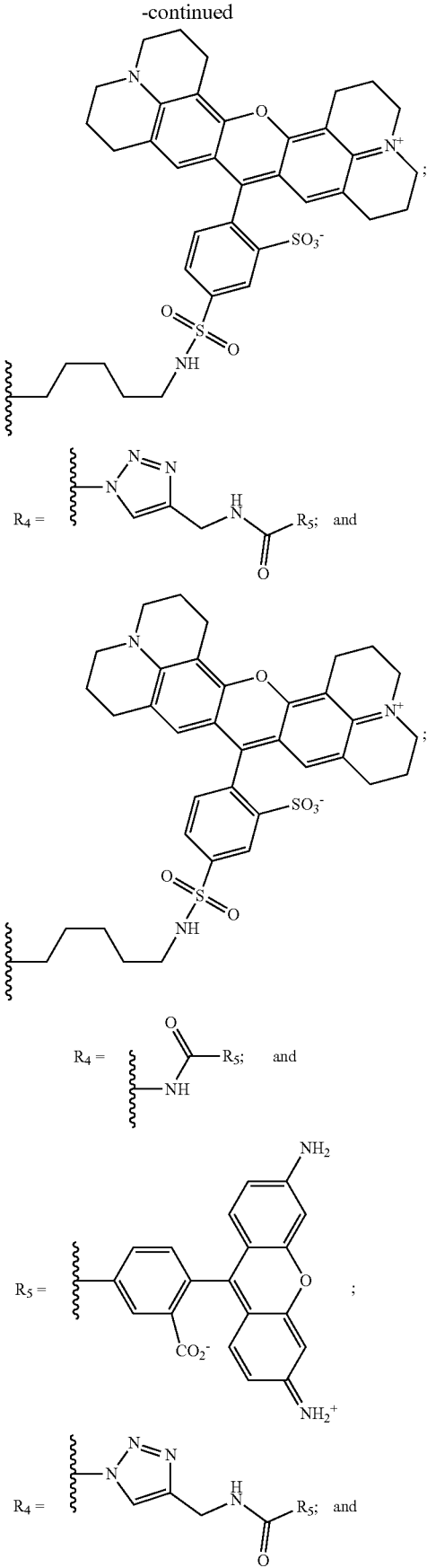

R₅ = 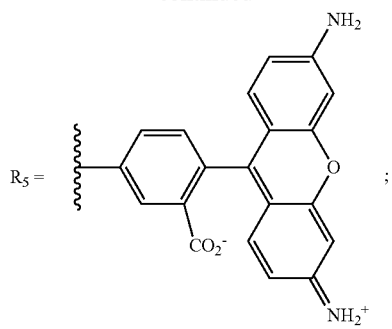;
R₄ = 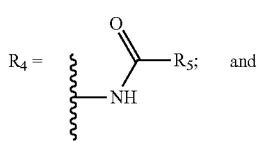 and
R₅ = 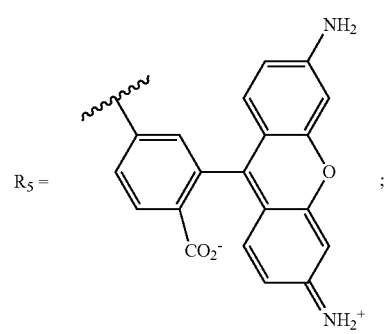;
R₄ = 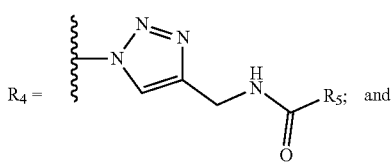 and
R₅ = 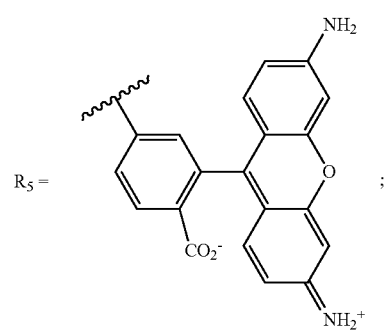;
R₄ = 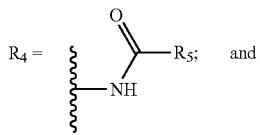 and
R₅ = 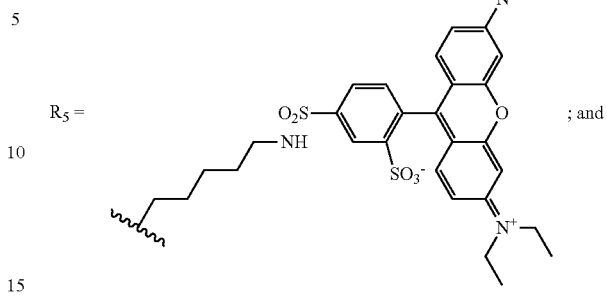; and
R₄ = 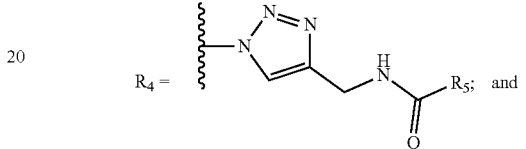 and
R₅ = 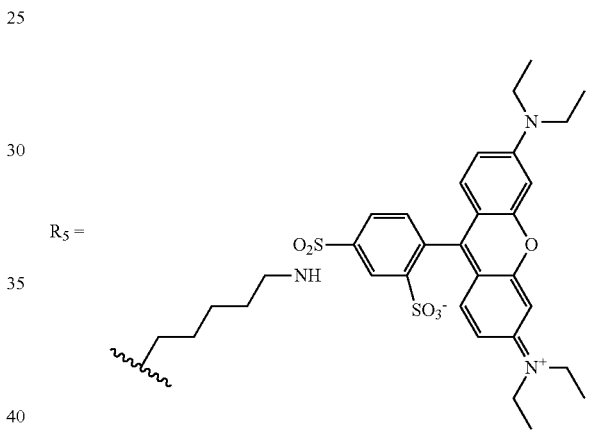
In another aspect, the invention provides a compound of Formula IV, or salt, hydrate, solvate, or prodrug thereof:
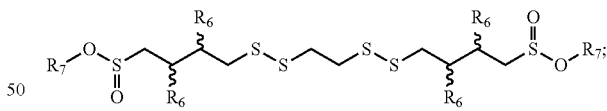
wherein, each R₆ is independently selected from
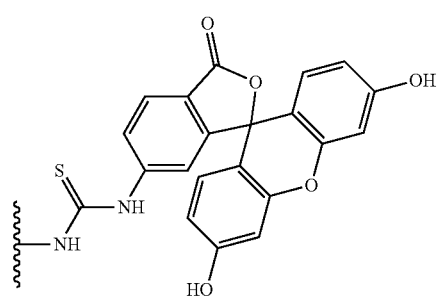
and -continued

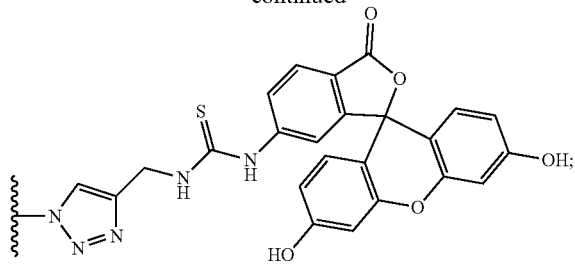

and each $R_7$ is independently H, Na, K, optionally substituted alkyl, optionally substituted aryl, or optionally substituted arylalkyl. In another aspect, the compound of Formula IV is represented by Formula VI:

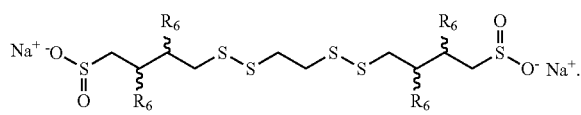

In any of the embodiments described herein, the compound of Formulae III-XIX, or salt, solvate, hydrate or prodrug thereof, is (+/−)-

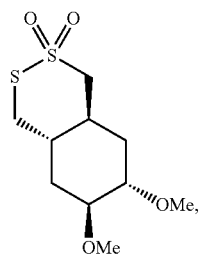 [SMILES: CO[C@H]1C[C@@H]2CS(=O)(=O)SC[C@H]2C[C@@H]1OC]

or salt, solvate, hydrate or prodrug thereof.

In any of the embodiments described herein, the DR5 agonist is TRAIL or TRAIL analog (e.g., TRAIL trimer, stabilized form of TRAIL, and the like), a DR5 agonist antibody, or a TRAIL synthesis inducer (e.g., TIC10).

In any of the embodiments described herein, the compound of Formulae III-XIX, or salt, solvate, hydrate or prodrug thereof, is (+/−)-

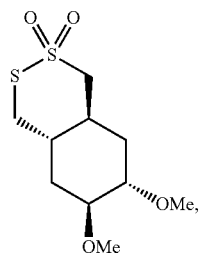 [SMILES: CO[C@H]1C[C@@H]2CS(=O)(=O)SC[C@H]2C[C@@H]1OC]

or salt, solvate, hydrate or prodrug thereof, and the DR5 agonist is TRAIL.

In any of the embodiments described herein, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

Other aspects and embodiments of the invention are disclosed infra.

BRIEF DESCRIPTION OF THE DRAWINGS

The present invention is further described below with reference to the following non-limiting examples and with reference to the following figures, in which.

DETAILED DESCRIPTION OF THE INVENTION

Figure 1:
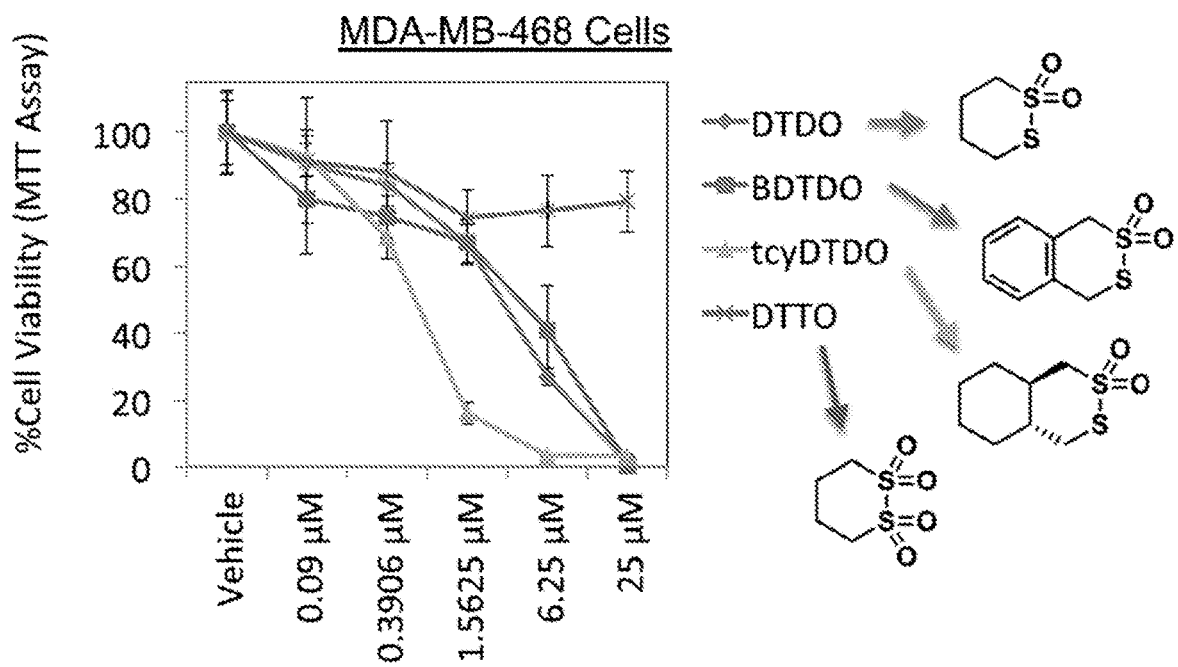
FIG. 1. depicts the profiling of various compounds of the invention in a MDA-MB-468 cell viability assay.

EGFR, HER2, and HER3 share evolutionarily conserved extracellular domains stabilized by disulfide bonds [Ogiso, H., Ishitani, R., Nureki, O., Fukai, S., Yamanaka, M., Kim, J. H., Saito, K., Sakamoto, A., Inoue, M., Shirouzu, M., and Yokoyama, S. (2002) Crystal structure of the complex of human epidermal growth factor and receptor extracellular domains Cell 110, 775-787; Garrett, T. P., McKern, N. M., Lou, M., Elleman, T. C., Adams, T. E., Lovrecz, G. O., Kofler, M., Jorissen, R. N., Nice, E. C., Burgess, A. W., and Ward, C. W. (2003) The crystal structure of a truncated ErbB2 ectodomain reveals an active conformation, poised to interact with other ErbB receptors Mol Cell 11, 495-505; Cho, H. S., Mason, K., Ramyar, K. X., Stanley, A. M., Gabelli, S. B., Denney, D. W., Jr., and Leahy, D. J. (2003) Structure of the extracellular region of HER2 alone and in complex with the Herceptin Fab Nature 421, 756-760; Cho, H. S., and Leahy, D. J. (2002) Structure of the extracellular region of HER3 reveals an interdomain tether Science 297, 1330-1333]. Given the intricate and extensive network of disulfide bonding in these receptors, compounds able to disrupt disulfide bonds (e.g., any of the compounds herein or formulae presented herein) would preferentially inactivate these oncogenic proteins.

1. Definitions

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally affect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In certain embodiments, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In one embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In certain embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, or about 0.01 to 25 mg/kg body weight, or about 0.1 to 20 mg/kg body weight, or about 1 to 10 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or can include a series of treatments. In one example, a subject is treated with a compound of the invention in the range of between about 0.1 to 20 mg/kg body weight, one time per week for between about 1 to 10 weeks, or between 2 to 8 weeks, or between about 3 to 7 weeks, or for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In certain embodiments, this term refers to any qualitative or quantitative improved therapeutic property of a compound of the invention, such as reduced toxicity.

The term "cell proliferative disorder" includes disorders involving the undesired or uncontrolled proliferation of a cell. Examples of such disorders include, but are not limited to, tumors (e.g., brain, lung (small cell and non-small cell), ovary, prostate, breast or colon) or other carcinomas or sarcomas (e.g., leukemia, lymphoma).

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-($C_1$-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound capable of inhibiting CDCP1" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a cell proliferative disorder.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" of the invention includes all vertebrates, e.g., mammals; e.g., rodents; e.g., mice; and non-mammals, such as non-human primates; e.g., sheep, dog, cow, chickens, amphibians, reptiles, etc.

The term "susceptible to a cell proliferative disorder" is meant to include subjects at risk of developing disorder of cell proliferation, e.g., cancer, i.e., subjects suffering from viral infection with cancer causing viruses, subjects that have been exposed to ionizing radiation or carcinogenic compounds, subjects having a family or medical history of cancer, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment.

The term "DR5 agonist" refers to any molecule that partially or fully enhances, stimulates or activates one or more biological activities of DR5, in vitro, in situ, or in vivo. Exemplary DR5 agonists include DR5 binding scaffolds, such as anti-DR5 antibodies ("DR5 antibodies"), e.g., chimeric, humanized or fully human antibodies, an antigen binding portion thereof, or molecules that are based on or derived from any of these. DR5 agonists may also be non-antibody proteins. DR5 agonist also includes DR5 ligands (e.g., TRAIL) and molecules that are derived from or based on TRAIL (e.g., TRAIL trimers or stabilized forms of TRAIL). DR5 agonist also includes molecules that induce the production or synthesis of TRAIL (e.g., TIC10).

Exemplary DR5 antibodies include, but are not limited to, Conatumumab, Drozitumab, Apomab, DAB4, PRO95780, Lexatumumab, HGS-ETR2, Tigatuzumab, CS-1008, TRA-8, HGSTR2J, KMTRS, and LBY-135.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides a compound that inhibits or is capable of inhibiting EGFR, HER2, and/or HER3. In another aspect, the compound inhibits or is capable of inhibiting at least two of EGFR, HER2, and HER3. In another aspect, the compound inhibits or is capable of inhibiting all three of EGFR, HER2, and HER3. In another aspect, the compound is capable of treating HER2-positive breast cancer. In another aspect, the compound is capable of treating breast cancer modulated by EGFR, HER2, and/or HER3.

In one aspect, the invention provides a pharmaceutical composition that inhibits or is capable of inhibiting EGFR, HER2, and/or HER3, the pharmaceutical composition comprising: 1) a compound of Formula (I)-(VI), or salt, solvate, hydrate or prodrug thereof; 2) a DR5 agonist; and 3) a pharmaceutically acceptable carrier. In another aspect, the composition inhibits or is capable of inhibiting at least two of EGFR, HER2, and HER3. In another aspect, the composition inhibits or is capable of inhibiting all three of EGFR, HER2, and HER3. In another aspect, the composition is capable of treating HER2-positive breast cancer. In another aspect, the compound is capable of treating breast cancer modulated by EGFR, HER2, and/or HER3.

In one aspect, the invention provides a pharmaceutical composition that inhibits or is capable of inhibiting EGFR, HER2, and/or HER3, the pharmaceutical composition comprising: 1) a compound of any one of Formulae III-XIX, or salt, solvate, hydrate or prodrug thereof; and 2) a pharmaceutically acceptable carrier. In another aspect, the invention provides a pharmaceutical composition that inhibits or is capable of inhibiting EGFR, HER2, and/or HER3, the pharmaceutical composition comprising: 1) a compound of any one of Formulae III-XIX, or salt, solvate, hydrate or prodrug thereof; 2) a DR5 agonist; and 3) a pharmaceutically acceptable carrier. In another aspect, the composition inhibits or is capable of inhibiting at least two of EGFR, HER2, and HER3. In another aspect, the composition inhibits or is capable of inhibiting all three of EGFR, HER2, and HER3. In another aspect, the composition is capable of treating HER2-positive breast cancer. In another aspect, the compound is capable of treating breast cancer modulated by EGFR, HER2, and/or HER3.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

3. Uses of the Compounds of the Invention

As described herein below, it has now surprisingly been found that the combination of a compound of Formula (I)-(VI) and a DR5 agonist can treat disorders of cell proliferation, including cancer, in a synergistic manner (i.e., the anticancer effect of the combination of a compound of Formula (I)-(VI) and a DR5 agonist is greater than the anticancer effect of each component alone).

In another aspect, the combination of a compound of any one of Formulae III-XIX, or salt, solvate, hydrate or prodrug thereof, and a DR5 agonist can treat disorders of cell proliferation, including cancer, in a synergistic manner (i.e., the anticancer effect of the combination of a compound of Formulae III-XIX and a DR5 agonist is greater than the anticancer effect of each component alone).

As described herein below, it has now surprisingly been found that a dosing regimen comprising the combination of a compound of Formula (I)-(VI) and a DR5 agonist can treat disorders of cell proliferation, including cancer, in a synergistic manner (i.e., the anticancer effect of the combination of a compound of Formula (I)-(VI) and a DR5 agonist is greater than the anticancer effect of each component alone).

In another aspect, a dosing regimen comprising the combination of a compound of any one of Formulae III-XIX, or salt, solvate, hydrate or prodrug thereof, and a DR5 agonist can treat disorders of cell proliferation, including cancer, in a synergistic manner (i.e., the anticancer effect of the combination of a compound of Formulae III-XIX and a DR5 agonist is greater than the anticancer effect of each component alone).

As described herein below, it has now surprisingly been found that a pharmaceutical composition comprising the combination of a compound of Formula (I)-(VI) and a DR5 agonist can treat disorders of cell proliferation, including cancer, in a synergistic manner (i.e., the anticancer effect of the combination of a compound of Formula (I)-(VI) and a DR5 activator is greater than the anticancer effect of each component alone).

In another aspect, a pharmaceutical composition comprising the combination of a compound of any one of Formulae III-XIX, or salt, solvate, hydrate or prodrug thereof, and a DR5 agonist can treat disorders of cell proliferation, including cancer, in a synergistic manner (i.e., the anticancer effect of the combination of a compound of Formulae II-XIX and a DR5 activator is greater than the anticancer effect of each component alone).

Thus, in one embodiment, the invention provides methods for treating a subject for a cell proliferative disorder, by administering to the subject an effective amount of a compound of Formula (I)-(VI) and an effective amount of a DR5 agonist (or a dosing regimen or pharmaceutical composition comprising a compound of Formula (I)-(VI) and a DR5 agonist). A cell proliferative disorder includes cancer. In certain embodiments, the subject is a mammal, e.g., a primate, e.g., a human.

Thus, in one embodiment, the invention provides methods for treating a subject for a cell proliferative disorder, by administering to the subject an effective amount of a compound of any one of Formulae III-XIX, or salt, solvate, hydrate or prodrug thereof (or a dosing regimen or pharmaceutical composition thereof). In another aspect, the invention provides methods for treating a subject for a cell proliferative disorder, by administering to the subject an effective amount of a compound of any one of Formulae III-XIX, or salt, solvate, hydrate or prodrug thereof, and an effective amount of a DR5 agonist (or a dosing regimen or pharmaceutical composition comprising a compound of Formulae III-XIX and a DR5 agonist). A cell proliferative disorder includes cancer. In certain embodiments, the subject is a mammal, e.g., a primate, e.g., a human.

A further aspect presents a method of treating a subject suffering from or susceptible to cancer, including administering to the subject an effective amount of a compound of Formula (I)-(VI) and an effective amount of a DR5 agonist (or a dosing regimen or pharmaceutical composition comprising a compound of Formula (I)-(VI) and a DR5 agonist) to thereby treat the subject suffering from or susceptible to cancer.

A further aspect presents a method of treating a subject suffering from or susceptible to cancer, including administering to the subject an effective amount of a compound of any one of Formulae III-XIX, or salt, solvate, hydrate or prodrug thereof (or a dosing regimen or pharmaceutical composition thereof) to thereby treat the subject suffering from or susceptible to cancer.

A further aspect presents a method of treating a subject suffering from or susceptible to cancer, including administering to the subject an effective amount of a compound of any one of Formulae III-XIX, or salt, solvate, hydrate or prodrug thereof, and an effective amount of a DR5 agonist (or a dosing regimen or pharmaceutical composition comprising a compound of Formulae III-XIX and a DR5 agonist) to thereby treat the subject suffering from or susceptible to cancer.

In certain embodiments, the methods of the invention include administering to a subject a therapeutically effective amount of a compound of Formula (I)-(VI) and an effective amount of a DR5 agonist (or a dosing regimen or pharmaceutical composition comprising a compound of Formula (I)-(VI) and a DR5 agonist) in combination with another pharmaceutically active compound. Examples of pharmaceutically active compounds include compounds known to treat cell proliferative disorders, e.g., imatinib (Gleevec). Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the methods of the invention include administering to a subject a therapeutically effective amount of a compound of any one of Formulae I-XIX, or salt, solvate, hydrate or prodrug thereof (or a dosing regimen or pharmaceutical composition thereof) in combination with another pharmaceutically active compound. In certain embodiments, the methods of the invention include administering to a subject a therapeutically effective amount of a compound of any one of Formulae II-XIX, or salt, solvate, hydrate or prodrug thereof, and an effective amount of a DR5 agonist (or a dosing regimen or pharmaceutical composition comprising a compound of Formulae III-XIX and a DR5 agonist) in combination with another pharmaceutically active compound. Examples of pharmaceutically active compounds include compounds known to treat cell proliferative disorders, e.g., imatinib (Gleevec). Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell New Jersey, Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times)

In certain embodiments, the compound of Formula (I)-(VI) and an effective amount of a DR5 agonist (or a dosing regimen or pharmaceutical composition comprising a compound of Formula (I)-(VI) and a DR5 agonist) can be used in combination therapy with conventional cancer chemotherapeutics. Conventional treatment regimens for leukemia and for other tumors include radiation, surgery, drugs, or combinations thereof. In addition to radiation, the following drugs, usually in combinations with each other, are often used to treat acute leukemias: vincristine, prednisone, methotrexate, mercaptopurine, cyclophosphamide, and cytarabine. In chronic leukemia, for example, busulfan, melphalan, and chlorambucil can be used in combination. Most conventional anti-cancer drugs are highly toxic and tend to make patients quite ill while undergoing treatment. Vigorous therapy is based on the premise that unless every cancerous cell is destroyed, the residual cells will multiply and cause a relapse.

In certain embodiments, the compound of Formulae III-XIX, or salt, solvate, hydrate or prodrug thereof, (or a dosing regimen or pharmaceutical composition thereof) can be used in combination therapy with conventional cancer chemotherapeutics. In certain embodiments, the compound of Formulae III-XIX, or salt, solvate, hydrate or prodrug thereof and an effective amount of a DR5 agonist (or a dosing regimen or pharmaceutical composition comprising a compound of Formulae III-XIX and a DR5 agonist) can be used in combination therapy with conventional cancer chemotherapeutics. Conventional treatment regimens for leukemia and for other tumors include radiation, surgery, drugs, or combinations thereof. In addition to radiation, the following drugs, usually in combinations with each other, are often used to treat acute leukemias: vincristine, prednisone, methotrexate, mercaptopurine, cyclophosphamide, and cytarabine. In chronic leukemia, for example, busulfan, melphalan, and chlorambucil can be used in combination. Most conventional anti-cancer drugs are highly toxic and tend to make patients quite ill while undergoing treatment. Vigorous therapy is based on the premise that unless every cancerous cell is destroyed, the residual cells will multiply and cause a relapse.

In certain aspects, the DR5 agonist is TRAIL or TRAIL analog (e.g., TRAIL, trimer, stabilized form of TRAIL, and the like), a DR5 agonist antibody, or a TRAIL synthesis inducer (e.g., TIC10).

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a cell proliferative disorder by methods well known in the art (e.g., determining tumor size or screening for tumor markers where the cell proliferative disorder is cancer) and then administering a therapeutically effective amount of an inhibitor of cell proliferation (e.g., a compound of any formula herein or otherwise described herein) according to the invention to the subject. After an appropriate period of time after the administration of the compound (e.g., 1 day, 1 week, 2 weeks, one month, six months), the extent of the cell proliferative disorder is determined again. The modulation (e.g., decrease) of the extent or invasiveness of the cell proliferative disorder indicates efficacy of the treatment. The extent or invasiveness of the cell proliferative disorder may be determined periodically throughout treatment. For example, the extent or invasiveness of the cell proliferative disorder may be checked every few hours, days or weeks to assess the further efficacy of the treatment. A decrease in extent or invasiveness of the cell proliferative disorder indicates that the treatment is efficacious. The method described may be used to screen or select patients that may benefit from treatment with an inhibitor of a cell proliferative disorder.

As used herein, "obtaining a biological sample from a subject," includes obtaining a sample for use in the methods described herein. A biological sample is described above.

In another aspect, a compound of Formula (I)-(VI) and a DR5 agonist (or a dosing regimen or pharmaceutical composition comprising a compound of Formula (I)-(VI) and a DR5 agonist) is packaged in a therapeutically effective amount with a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In another aspect, methods of inhibiting a cell proliferative disorder in a subject include administering an effective amount of a compound of the invention to the subject. The administration may be by any route of administering known in the pharmaceutical arts. The subject may have a cell proliferative disorder, may be at risk of developing a cell proliferative disorder, or may need prophylactic treatment prior to anticipated or unanticipated exposure to conditions capable of increasing susceptibility to a cell proliferative disorder, e.g., exposure to carcinogens or to ionizing radiation.

In one aspect, a method of monitoring the progress of a subject being treated includes determining the pre-treatment status (e.g., size, growth rate, or invasiveness of a tumor) of the cell proliferative disorder, administering a therapeutically effective amount of compound of Formula (I)-(VI) and a DR5 agonist (or a dosing regimen or pharmaceutical composition comprising a compound of Formula (I)-(VI) and a DR5 agonist) to the subject, and determining the status of the cell proliferative disorder after an initial period of treatment, wherein the modulation of the status indicates efficacy of the treatment.

In one aspect, a method of monitoring the progress of a subject being treated includes determining the pre-treatment status (e.g., size, growth rate, or invasiveness of a tumor) of the cell proliferative disorder, administering a therapeutically effective amount of compound of Formulae III-XIX, or salt, solvate, hydrate or prodrug thereof, (or a dosing regimen or pharmaceutical composition thereof) to the subject, and determining the status of the cell proliferative disorder after an initial period of treatment, wherein the modulation of the status indicates efficacy of the treatment.

In one aspect, a method of monitoring the progress of a subject being treated includes determining the pre-treatment status (e.g., size, growth rate, or invasiveness of a tumor) of the cell proliferative disorder, administering a therapeutically effective amount of compound of Formulae III-XIX, or salt, solvate, hydrate or prodrug thereof, and a DR5 agonist (or a dosing regimen or pharmaceutical composition comprising a compound of Formulae III-XIX and a DR5 agonist) to the subject, and determining the status of the cell proliferative disorder after an initial period of treatment, wherein the modulation of the status indicates efficacy of the treatment.

The subject may be at risk of a cell proliferative disorder, may be exhibiting symptoms of a cell proliferative disorder, may be susceptible to a cell proliferative disorder and/or may have been diagnosed with a cell proliferative disorder.

The initial period of treatment may be the time in which it takes to establish a stable and/or therapeutically effective blood serum level of any of the compounds, compound combinations, dosing regimens, or pharmaceutical compositions delineated herein, or the time in which it take for the subject to clear a substantial portion of the compound, or any period of time selected by the subject or healthcare professional that is relevant to the treatment.

If the modulation of the status indicates that the subject may have a favorable clinical response to the treatment, the subject may be treated with the compound. For example, the subject can be administered a therapeutically effective dose or doses of the compound.

In another aspect, the invention provides methods for inhibiting EGFR, HER2, and/or HER3 signaling in a cell. The methods include contacting the cell with an effective amount of any of the compounds, compound combinations, dosing regimens, or pharmaceutical compositions delineated herein, such that the signaling of EGFR, HER2, and/or HER3 is reduced The contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

The EGFR, HER2, and/or HER3 may be within a cell, isolated from a cell, recombinantly expressed, purified or isolated from a cell or recombinant expression system or partially purified or isolated from a cell or recombinant expression system.

The contacting may be in vitro, e.g., by addition of the compound to a solution containing purified EGFR, HER2, and/or HER3, or, if EGFR, HER2, and/or HER3 is present in cells, by adding the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

Kits of the invention include kits for treating a cell proliferative disorder in a subject. The invention also includes kits for downregulating expression of EGFR, HER2, and/or HER3, stabilizing an interaction of EGFR, HER2, and/or HER3, assessing the efficacy of a treatment for a cell proliferative disorder in a subject, monitoring the progress of a subject being treated for a cell proliferative disorder, selecting a subject with a cell proliferative disorder for treatment according to the invention, and/or treating a subject suffering from or susceptible to a cell proliferative disorder. The kit may include any of the compounds, compound combinations, dosing regimens, or pharmaceutical compositions delineated herein and instructions for use. The instructions for use may include information on dosage, method of delivery, storage of the kit, etc. The kits may also include reagents, for example, test compounds, buffers, media (e.g., cell growth media), cells, etc. Test compounds may include known compounds or newly discovered compounds, for example, combinatorial libraries of compounds. One or more of the kits of the invention may be packaged together, for example, a kit for assessing the efficacy of a treatment for a cell proliferative disorder may be packaged with a kit for monitoring the progress of a subject being treated for a cell proliferative disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

Alternatively, the effects of compound of the invention can be characterized in vivo using animals models.

4. Pharmaceutical Compositions

In another aspect, the invention provides a pharmaceutical composition comprising: 1) a compound of Formula (I)-(VI), or salt, solvate, hydrate or prodrug thereof; 2) a DR5 agonist; and 3) a pharmaceutically acceptable carrier. In another aspect, the compound of Formula (I)-(VI) is

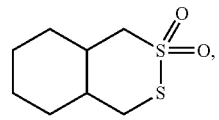 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TICO). In another aspect, the DR5 agonist is TRAIL. In another aspect, the compound of Formula (I)-(VI) is

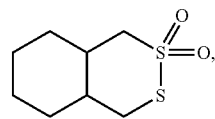 [SMILES: O=S1(=O)CC2CCCCC2CS1]

or salt, solvate, hydrate or prodrug thereof, and the DR5 agonist is TRAIL.

In another aspect, the invention provides a dosing regimen for treating a cell proliferative disorder in a subject, the dosing regimen comprising: 1) a compound of Formula (I)-(VI), or salt, solvate, hydrate or prodrug thereof; and 2) a DR5 agonist. In another aspect, the dosing regimen further comprises a pharmaceutically acceptable carrier. In another aspect, the compound of Formula (I)-(VI) is

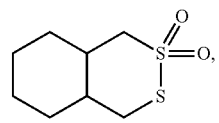 [SMILES: O=S1(=O)CC2CCCCC2CS1]

or salt, solvate, hydrate or prodrug thereof. In another aspect, the DR5 agonist is TRAIL or TRAIL analog (e.g., TRAIL trimer, stabilized form of TRAIL, and the like), a DR5 agonist antibody, or a TRAIL synthesis inducer (e.g., TIC10). In another aspect, the DR5 agonist is TRAIL. In another aspect, the compound of Formula (I)-(VI) is

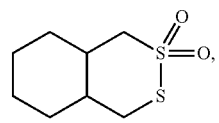 [SMILES: O=S1(=O)CC2CCCCC2CS1]

or salt, solvate, hydrate or prodrug thereof, and the DR5 agonist is TRAIL. In another aspect, the cell proliferative disorder is cancer. In a further aspect, the cancer is HER2 mediated. In a further aspect, the cancer is breast cancer. In a further aspect, the breast cancer is HER2-positive breast cancer. In another aspect, the breast cancer is modulated by HER2, HER3, and/or EGFR.

In another aspect, the invention provides a pharmaceutical composition comprising a compound of any one of Formulae III-XIX, or salt, solvate, hydrate or prodrug thereof, and a pharmaceutically acceptable carrier. In another aspect, the pharmaceutical composition comprises an additional agent. In another aspect, the additional agent is a DR5 agonist.

In another aspect, the invention provides a dosing regimen for treating a cell proliferative disorder in a subject, the dosing regimen comprising: 1) a compound of Formulae III-XIX, or salt, solvate, hydrate or prodrug thereof; and 2) a DR5 agonist. In another aspect, the dosing regimen further comprises a pharmaceutically acceptable carrier.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also be used in the pharmaceutical compositions herein.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount of a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BA), butylated hydroxytoluene (BT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, or from about 5 percent to about 70 percent, or from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH 5 to pH 7, with a pH of about pH 5.5 being typical.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the presently disclosed subject matter, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the invention could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Goodman and Gilman's *The Pharmaco-*

*logical Basis of Therapeutics,* 13th or latest edition, McGraw Hill Medical, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

Another object of the present invention is the use of a compound as described herein (e.g., of any formulae herein) in the manufacture of a medicament for use in the treatment of a metalloenzyme-mediated disorder or disease. Another object of the present invention is the use of a compound as described herein (e.g., of any formulae herein) for use in the treatment of a metalloenzyme-mediated disorder or disease. Another object of the present invention is the use of a compound as described herein (e.g., of any formulae herein) in the manufacture of an agricultural composition for use in the treatment or prevention of a metalloenzyme-mediated disorder or disease in agricultural or agrarian settings.

EXAMPLES

The invention is further illustrated by the following examples which are intended to illustrate but not limit the scope of the invention.

General Methods

Reagents and solvents were purchased from commercial sources and used without further purification unless otherwise specified. Anhydrous solvents were obtained using a commercial solvent drying system (using activated alumina for THF, dichloromethane) and transferred via syringe to flame-dried glassware that had been cooled under an argon or nitrogen atmosphere. $^1$H and $^{13}$C NMR spectra were recorded using commercially-obtained deuterated solvents on a Bruker-400 ($^1$H at 400 MHz; $^{13}$C at 101 MHz) spectrometer. Chemical shifts (δ) are given in parts per million (ppm) relative to TMS and referenced to residual protonated solvent (CDCl$_3$: $\delta_H$ 7.26 ppm, $\delta_C$ 77.16 ppm; CD$_3$OD: $\delta_H$ 4.87 ppm, $\delta_C$ 49.00 ppm; DMSO-d$_6$: $\delta_H$ 2.50 ppm, $\delta_C$ 39.52 ppm; D$_2$O: $\delta_H$ 4.79 ppm). Coupling constants (J) are reported in Hz. Spin multiplicities are presented by the following symbols: s (singlet), bs (broad singlet), d (doublet), t (triplet), q (quartet), p (pentet), and m (multiplet). Electrospray ionization (ESI) high-resolution mass spectra (HRMS) were recorded on an Agilent 6230 ESI-TOF instrument, operating in positive or negative ion mode as stated, with methanol as the carrier solvent.

Example 1

Compound Synthesis
Method A: Synthesis of Cyclic Analogs

A solution of the appropriate dithiol or diselenol (24.7 mmol) in AcOH (25 mL) is cooled in an ice bath and a 30% aqueous H$_2$O$_2$ solution (8.8 mL) is added slowly such that the temperature does not rise above 35° C. After stirring for an appropriate amount of time, the solvent is removed under vacuum, and the residue is diluted with water (25 mL), neutralized with NaHCO$_3$, and extracted with toluene (4×50 mL). The organic extract is dried with MgSO$_4$, and the solvent is removed under vacuum. The resulting solid may be recrystallized (e.g., from Et$_2$O) to afford the product.

Method B: Synthesis of Mono-Disulfide Acyclic Analogs

To a solution of the appropriate dithiane-dioxide or diselenane-dioxide (2.56 mmol) in anhydrous MeOH (6.4 mL) at room temperature (rt) under argon atmosphere, a solution of NaOMe (prepared from 58.9 mg of Na$^0$ in 5.1 mL of anhydrous MeOH) is added dropwise. The mixture is stirred. The reaction mixture is then concentrated under vacuum until a precipitate is formed and acetone is then added to further facilitate the precipitation. The solid is filtered, washed with acetone (3×10 mL), and dried under reduced pressure to afford the mono-disulfide acyclic product.

Method C: Synthesis of Poly-Disulfide Acyclic Analogs

To a mixture of the appropriate dithiane-dioxide or diselenane-dioxide (3.28 mmol) and 1,2-ethanedithiol (92 µL, 1.10 mmol) in anhydrous MeOH with stirring in ice bath, a solution of NaOMe (prepared by dissolution of 50 mg of Na0 in 2.2 mL of anhydrous MeOH) is slowly added. After the addition is complete, dry Et$_2$O is added to the reaction mixture until no additional precipitate is formed. The solid is filtered under vacuum and dissolved with a minimum amount of MeOH. The solution is transferred to centrifuge tubes and Et$_2$O is carefully added until the solution becomes turbid. The precipitate is removed by centrifugation and the supernatant is transferred to another flask, where Et$_2$O is added until precipitation is complete. The solid is collected by vacuum filtration and dried under reduced pressure to afford the poly-disulfide acyclic product.

Method D: Attachment to Dyes

The compounds described herein can also be conjugated to dyes through various functionalities present in the compounds of the invention (e.g., amino, carboxylic acid, thiol, etc.) using conventional chemistries well-known in the art. As just one non-limiting example, the dyes can be attached through amino moieties on the compounds described herein by reaction with various electrophilic sources of the dyes. Examples of such electrophilic moieties are activated esters (e.g., succinimidyl esters, sulfosuccinimidyl esters, tetrafluorophenyl esters, sulfodichlorophenol esters), isothiocyanates, sulfonyl chlorides, dichlorotriazines, halides, and acyl azides. Examples of dyes are biotin, fluorescein, AlexaFluor® dyes, BODIPY®, Cascade Blue®, coumarins, Oregon Green®, Pacific Blue™, Pacific Green™, Pacific Orange™, Rhodamine Green™, Rhodamine Red™, and Texas Red®.

Compounds 10b/10b* (or mixtures thereof) can be reacted with activated esters (e.g., succinimidyl esters) of various dyes (e.g., biotin), as depicted in Scheme I, to afford the conjugated analogs (e.g., Example 11).

Scheme I

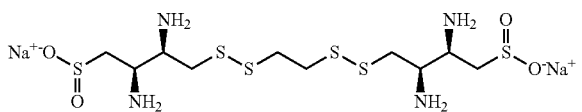
Example 10b

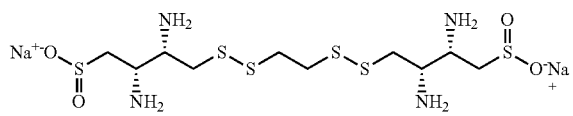
Example 10b*

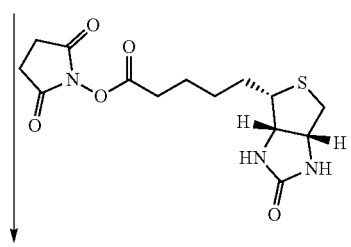

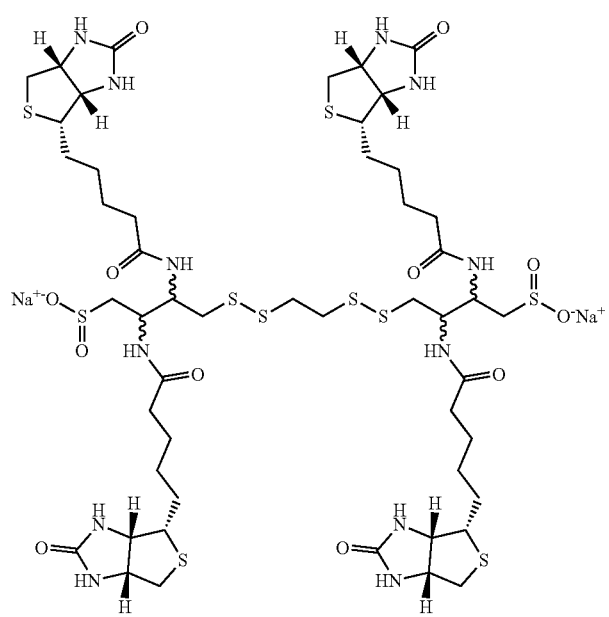
Example 11

As shown in Scheme 11, various dyes capped with a propargyl moiety (e.g., Biotin-NHCH2-≡) can be reacted with azides, 10c/10c*, to afford triazole, 12.

Scheme II

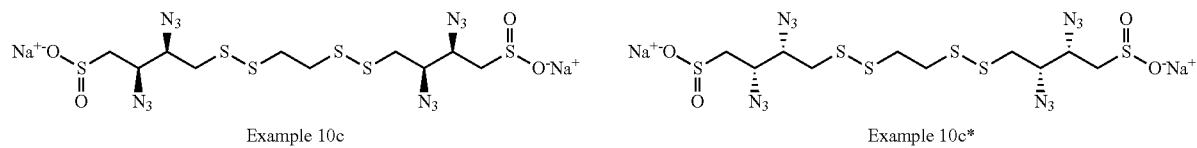

Example 10c                                   Example 10c*

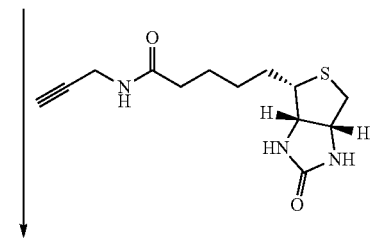

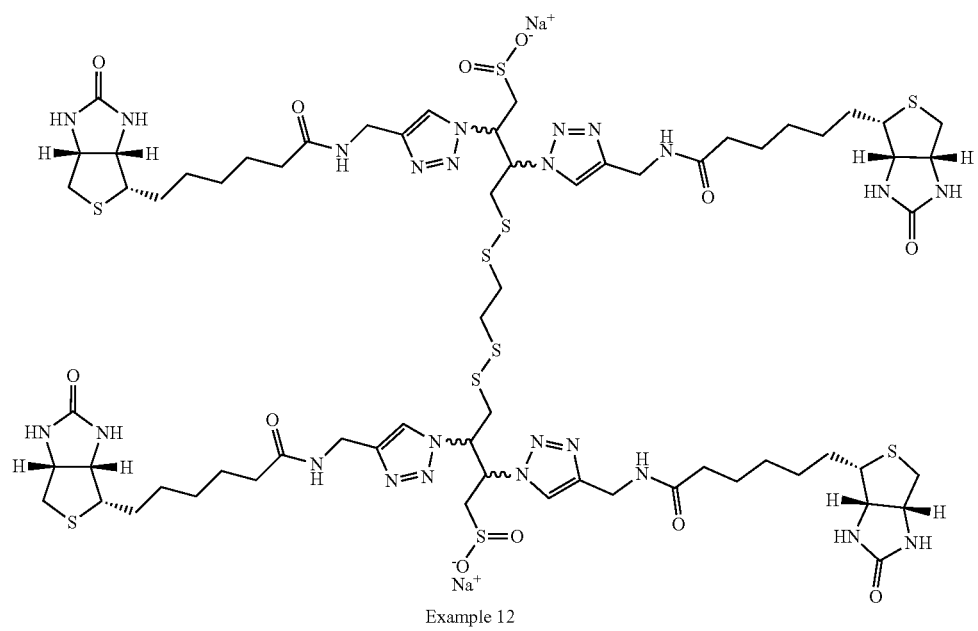

Example 12

Scheme III depicts synthetic methodology to attach various dyes (e.g., fluorescein) to compounds of the invention employing thioisocyanate dyes (e.g., fluorescein-NCS) to afford the corresponding thiourea-linked compounds (e.g., Example 66).

Scheme III
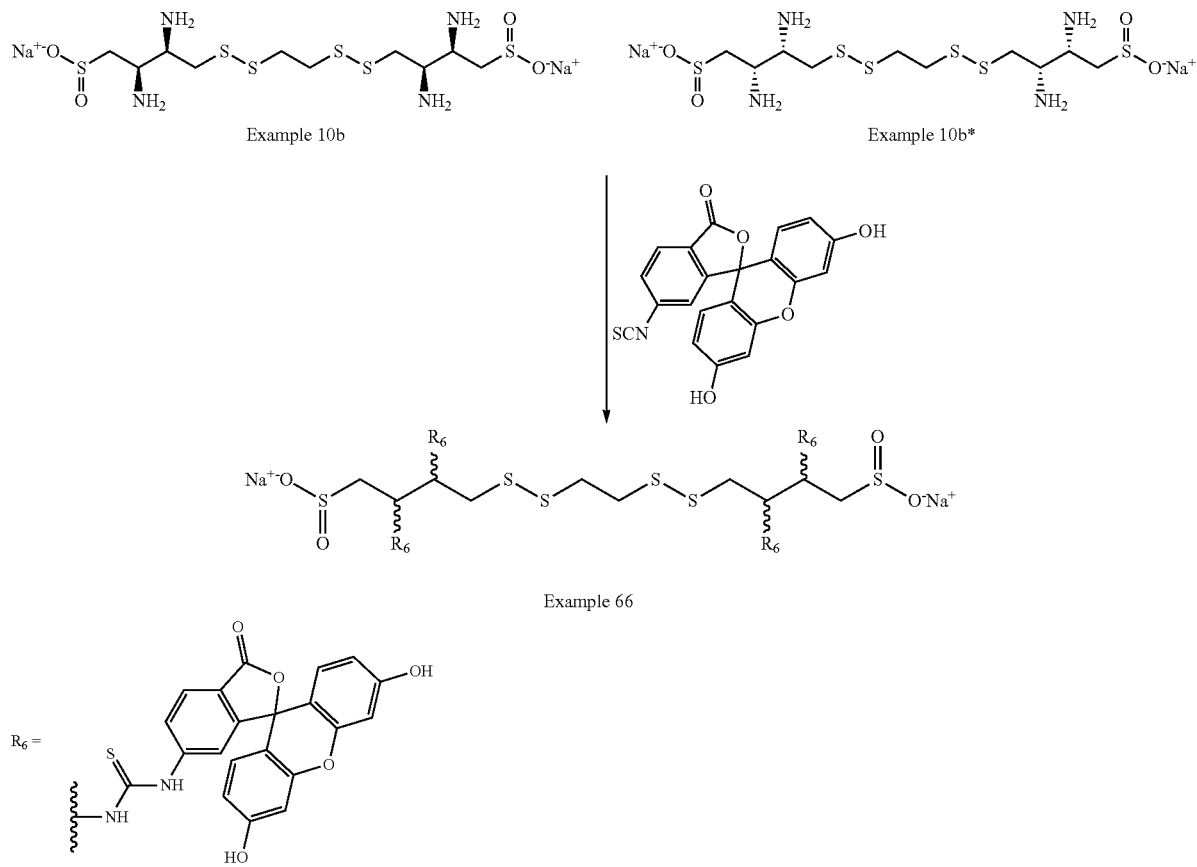
Alternatively, the isocyanate dye analogs (e.g., fluorescein-NCS) can be converted to the corresponding propoargyl-thiourea intermediates, which when reacted with azides 10c/10c*, affords Example 67 (Scheme IV).
Scheme IV
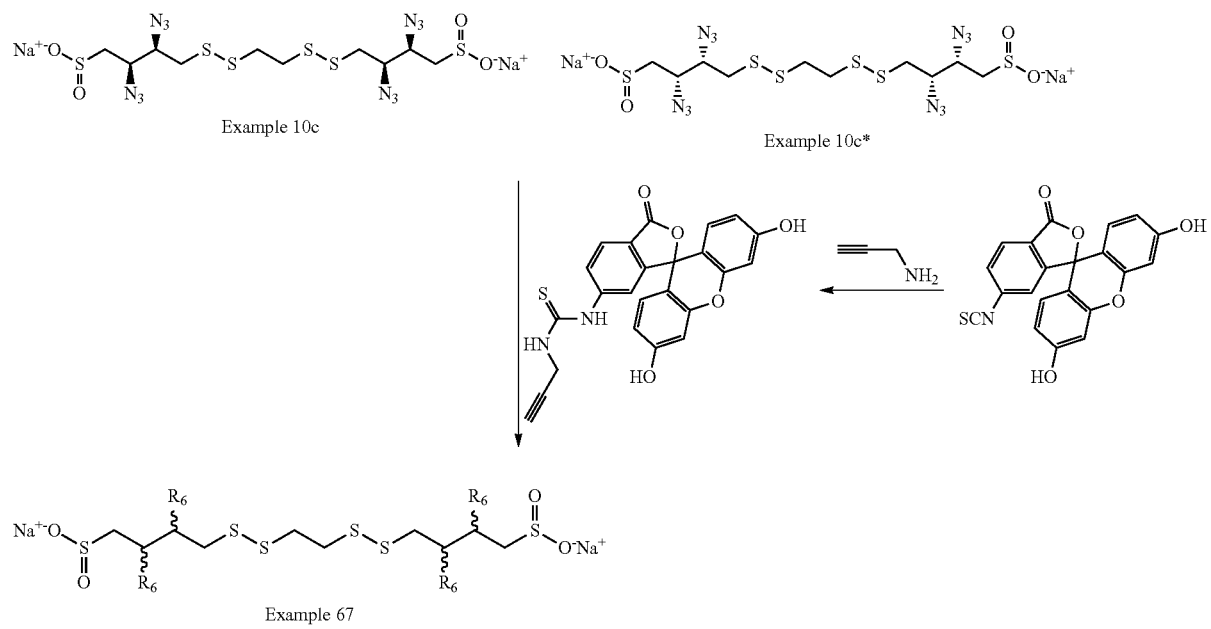

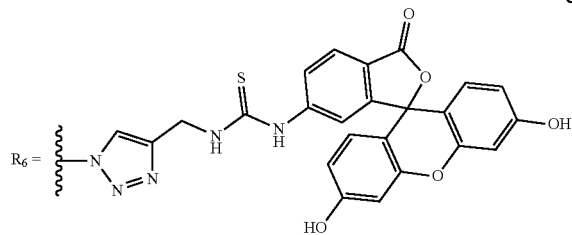

The following examples can be prepared according to one of Methods A, B, C, and/or D.

Example 1

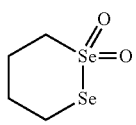

1,2-diselenane-1,1-dioxide (Method A)

Example 2

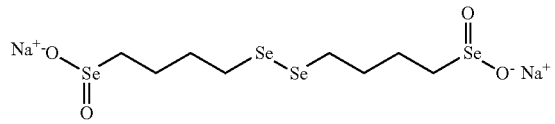

sodium 4,4'-diselanediyldibutane-1-seleninate (Method B)

Example 3

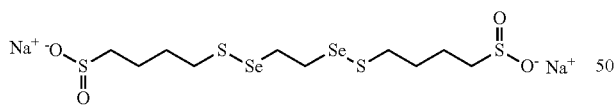

sodium 5,10-dithia-6,9-diselenatetradecane-1,14-disulfinate (Method C)

Example 4

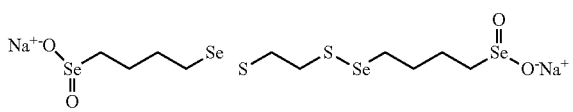

sodium 6,9-dithia-5,10-diselenatetradecane-1,14-diseleninate (Method C)

Example 5

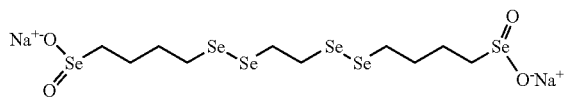

sodium 4,4'-(ethane-1,2-diylbis(diselanediyl))dibutane-1-seleninate (Method C)

Example 6

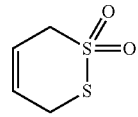

3,6-dihydro-1,2-dithiine-1,1-dioxide (Method A)

Example (Z,Z)-7

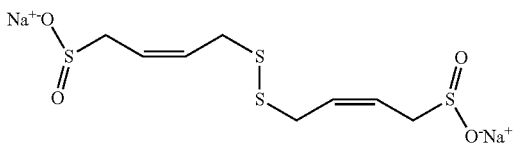

sodium (2Z,2'Z)-4,4'-disulfanediyldibit-2-ene-1-sulfinate (Method B)

Example (E,E)-7

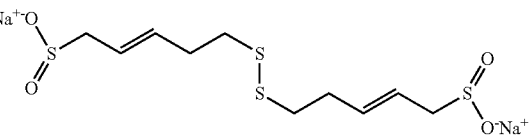

sodium (2E,2'E)-5,5'-disulfanediyldipent-2-ene-1-sulfinate (Method B)

Example 8a

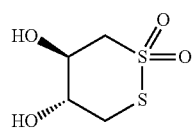

trans-1,2-dithiane-4,5-diol-1,1-dioxide (Method A)

Example 8b

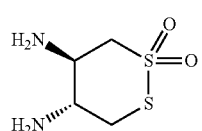

trans-1,2-dithiane-4,5-diamino-1,1-dioxide (Method A)

Example 8c

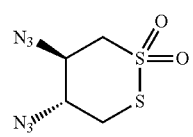 [SMILES: [N-]=[N+]=N[C@H]1CSS(=O)(=O)C[C@@H]1N=[N+]=[N-]]

trans-1,2-dithiane-4,5-diazido-1,1-dioxide (Method A)

Example 8d

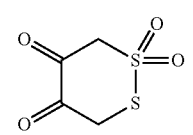

1,2-dithiane-4,5-dione-1,1-dioxide (Method A)

Example 8e

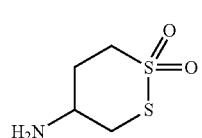

1,2-dithiane-4-amino-1,1-dioxide (Method A)

Example 8f

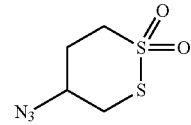

1,2-dithiane-4-azido-1,1-dioxide (Method A)

Example 8g

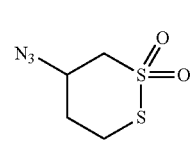

1,2-dithiane-5-amino-1,1-dioxide (Method A)

Example 8h

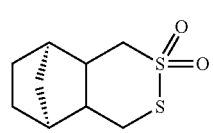 [SMILES: O=S1(=O)CC2C(CS1)[C@H]1CC[C@@H]2C1]

1,2-dithiane-5-azido-1,1-dioxide (Method A)

Example 8i (Method A)

Example 9a

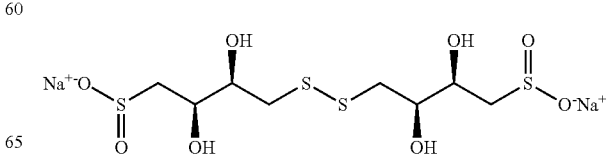

sodium (2R,2'R,3R,3'R)-4,4'-disulfanediylbis(2,3-dihydroxybutane-1-sulfinate) (Method B)

Example 9a*

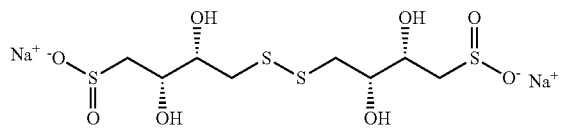

sodium (2S,2'S,3S,3'S)-4,4'-disulfanediylbis(2,3-dihydroxybutane-1-sulfinate) (Method B)

Example 9b

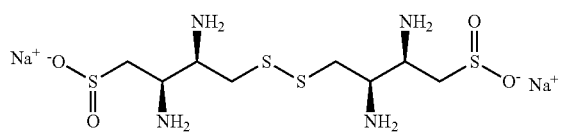

sodium (2R,2'R,3R,3'R)-4,4'-disulfanediylbis(2,3-diaminobutane-1-sulfinate) (Method B)

Example 9b*

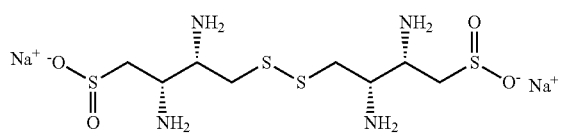

sodium (2S,2'S,3S,3'S)-44'-disulfanediylbis(2,3-diaminobutane-1-sulfinate) (Method B)

Example 9c

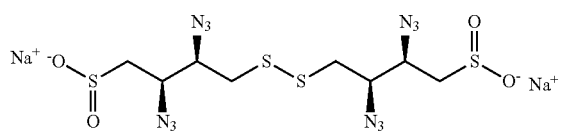

sodium (2R,2'R,3R,3'R)-4,4'-disulfanediylbis(2,3-diazidobutane-1-sulfinate) (Method B)

Example 9c*

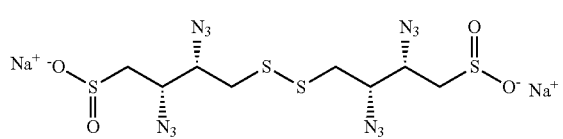

sodium (2S,2'S,3S,3'S)-4,4'-disulfanediylbis(2,3-diazidobutane-1-sulfinate) (Method B)

Example 9d

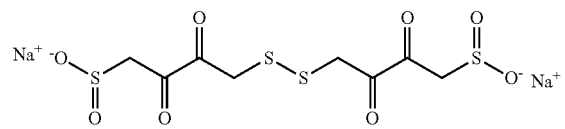

sodium 4,4'-disulfanediylbis(2,3-dioxobutane-1-sulfinate) (Method B)

Example 9e

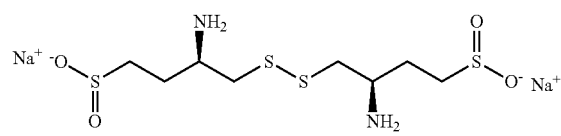

sodium (3R,3'R)-4,4'-disulfanediylbis(3-aminobutane-1-sulfinate) (Method B)

Example 9e*

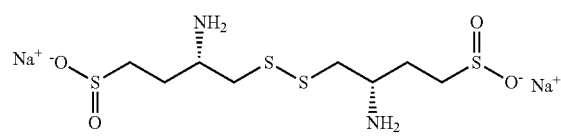

sodium (3S,3'S)-4,4'-disulfanediylbis(3-aminobutane-1-sulfinate) (Method B)

Example 9f

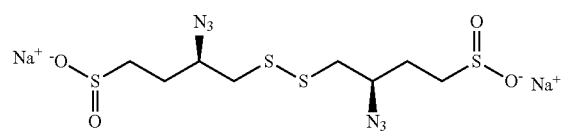

sodium (3R,3'R)-4,4'-disulfanediylbis(3-azidobutane-1-sulfinate) (Method B)

Example 9f*

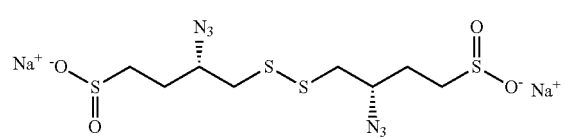

sodium (3S,3'S)-4,4'-disulfanediylbis(3-azidobutane-1-sulfinate) (Method B)

Example 9g

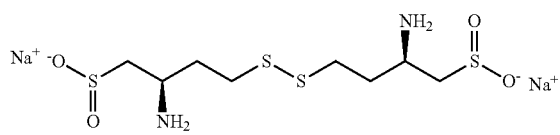

sodium (2R,2'R)-4,4'-disulfanediylbis(2-aminobutane-1-sulfinate) (Method B)

Example 9g*

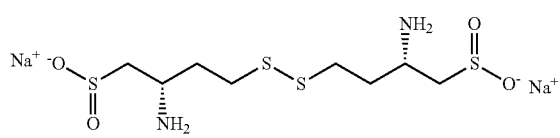

sodium (2S,2'S)-4,4'-disulfanediylbis(2-aminobutane-1-sulfinate) (Method B)

Example 9h

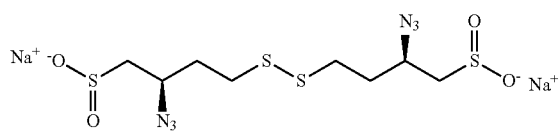

sodium (2R,2'R)-4,4'-disulfanediylbis(2-azidobutane-1-sulfinate) (Method B)

Example 9h*

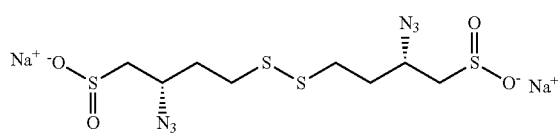

sodium (2S,2'S)-4,4'-disulfanediylbis(2-azidobutane-1-sulfinate) (Method B)

Example 9i

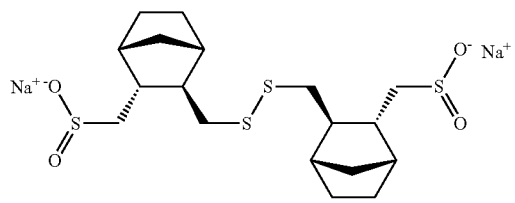

sodium (1R,1'R,2R,2'R,3R,3'R,4S,4'S)-3,3'-disulfanediylbis(methylene)bis(bicyclo[2.2.1]heptane-3,2-diyl)dimethanesulfinate (Method B)

Example 9i*

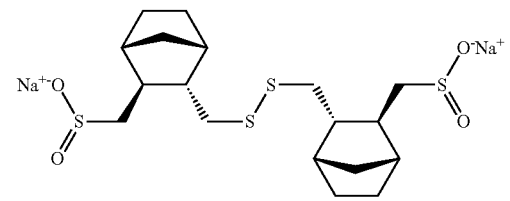

sodium (1R,1'R,2S,2'S,3S,3'S,4S,4'S)-3,3'-disulfanediylbis(methylene)bis(bicyclo[2.2.1]heptane-3,2-diyl)dimethanesulfinate (Method B)

Example 10a

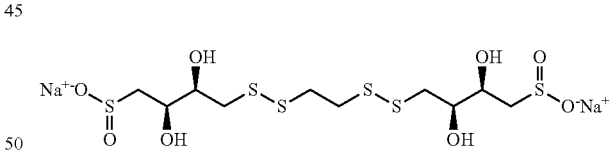

sodium (2R,2'R,3R,3'R)-4,4'-(ethane-1,2-diylbis(disulfanediyl))bis(2,3-dihydroxybutane-1-sulfinate) (Method C)

Example 10a*

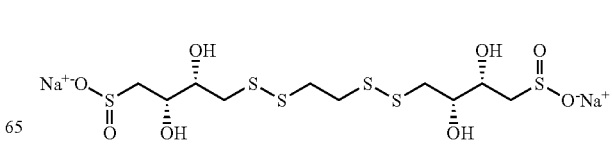

sodium (2S,2'S,3S,3'S)-4,4'-(ethane-1,2-diylbis(disulfanediyl))bis(2,3-dihydroxybutane-1-sulfinate) (Method C)

Example 10b

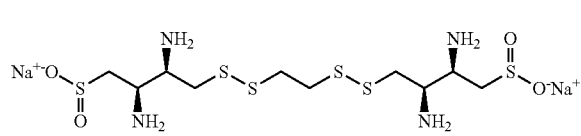

sodium (2R,2'R,3R,3'R)-4,4'-(ethane-1,2-diylbis(disulfanediyl))bis(2,3-diaminobutane-1-sulfinate) (Method C)

Example 10b*

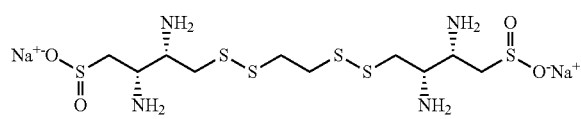

(2S,2'S,3S,3'S)-4,4'-(ethane-1,2-diylbis(disulfanediyl))bis(2,3-diaminobutane-1-sulfinate) (Method C)

Example 10c

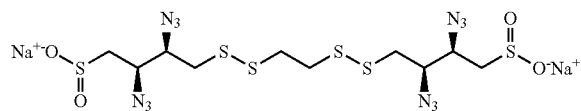

(2R,2'R,3R,3'R)-4,4'-(ethane-1,2-diylbis(disulfanediyl))bis(2,3-diazidobutane-1-sulfinate) (Method C)

Example 10c* sodium (2S,2'S,3S,3'S)-4,4'-(ethane-1,2-diylbis(disulfanediyl))bis(2,3-diazidobutane-1-sulfinate) (Method C)

Example 10d

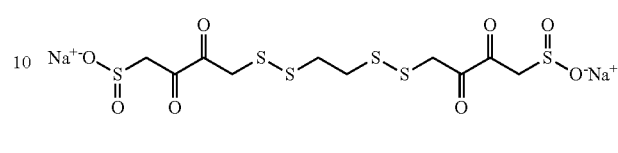

sodium 4,4'-(ethane-1,2-diylbis(disulfanediyl))bis(2,3-dioxobutane-1-sulfinate) (Method C)

Example 10e

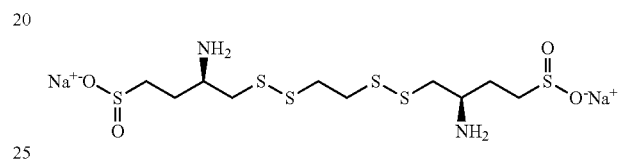

sodium (3R,3'R)-4,4-(ethane-1,2-diylbis(disulfanediyl))bis(3-aminobutane-1-sulfinate) (Method C)

Example 10e*

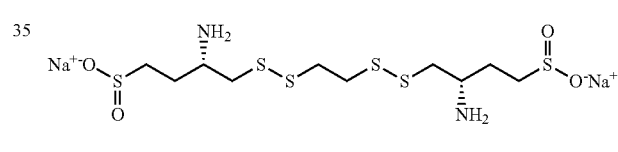

sodium (3S,3'S)-4,4'-(ethane-1,2-diylbis(disulfanediyl))bis(3-aminobutane-1-sulfinate) (Method C)

Example 10f

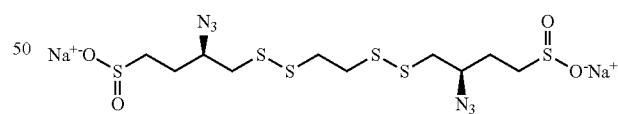

sodium (3R,3'R)-4,4-(ethane-1,2-diylbis(disulfanediyl))bis(3-azidobutane-1-sulfinate) (Method C)

Example 10f*

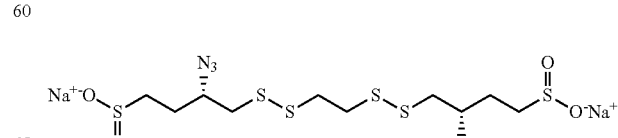

101 sodium (3S,3'S)-4,4'-(ethane-1,2-diylbis(disul-fanediyl))bis(3-azidobutane-1-sulfinate) (Method C)

Example 10g

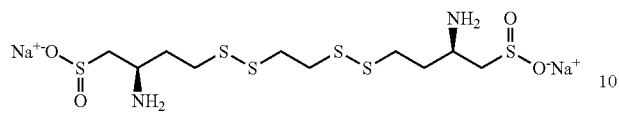

sodium (2R,2'R)-4,4-(ethane-1,2-diylbis(disul-fanediyl))bis(2-aminobutane-1-sulfinate) (Method C)

Example 10g*

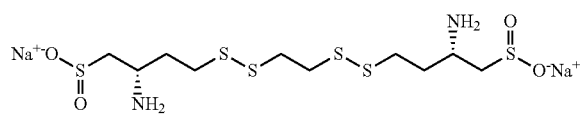

sodium (2S,2'S)-4,4'-(ethane-1,2-diylbis(disul-fanediyl))bis(2-aminobutane-1-sulfinate) (Method C)

Example 10h

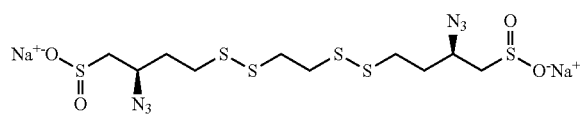

sodium (2R,2'R)-4,4'-(ethane-1,2-diylbis(disul-fanediyl))bis(2-azidobutane-1-sulfinate) (Method C)

Example 10h*

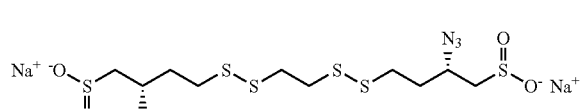

102 sodium (2S,2'S)-4,4'-(ethane-1,2-diylbis(disul-fanediyl))bis(2-azidobutane-1-sulfinate) (Method C)

Example 10i

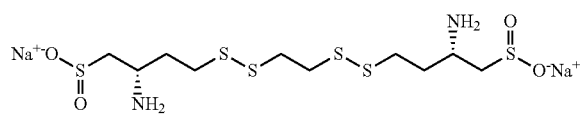

sodium (1R,1'R,2R,2'R,3R,3'R,4S,4'S)-3,3'-(ethane-1,2-diylbis(disulfanediyl))bis(methylene)bis(bicyclo[2.2.1]heptane-3,2-diyl)dimethanesulfinate (Method C)

Example 10i

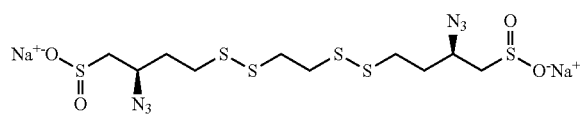

sodium (1R,1'R,2S,2'S,3S,3'S,4S,4'S)-3,3'-(ethane-1,2-diylbis(disulfanediyl))bis(methylene)bis(bicyclo[2.2.1]heptane-3,2-diyl)dimethanesulfinate (Method C)

The following compounds of Formula III can be prepared in accordance with the general procedures presented herein.

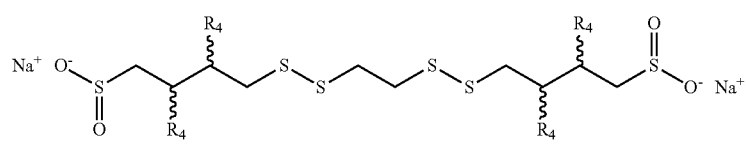

Formula III

103
Example 11
Compound of Formula III, wherein
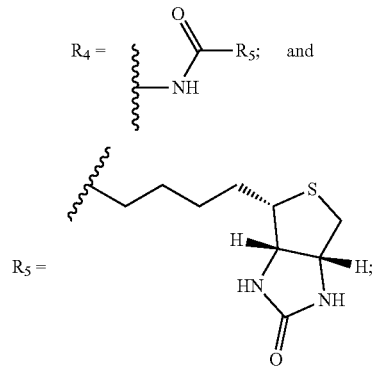
Example 12
Compound of Formula III, wherein
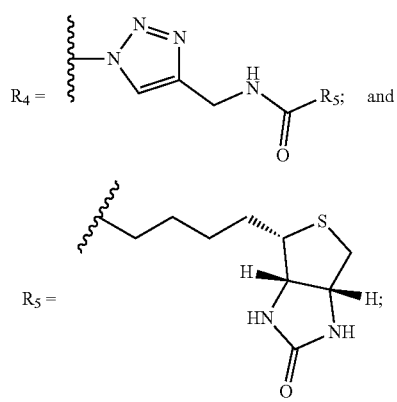
Example 13
Compound of Formula III, wherein
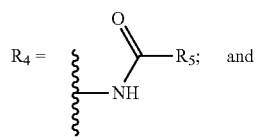
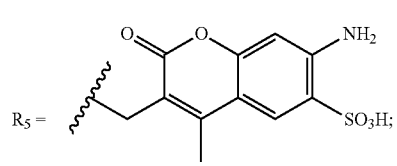
104
Example 14
Compound of Formula III, wherein
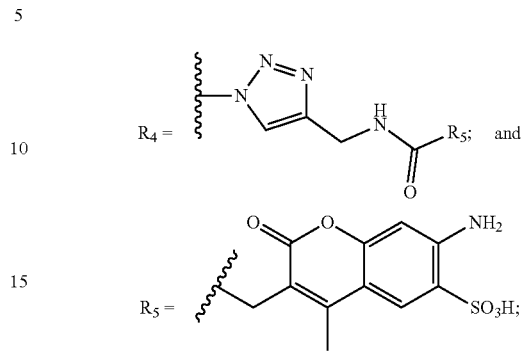
Example 15
Compound of Formula III, wherein
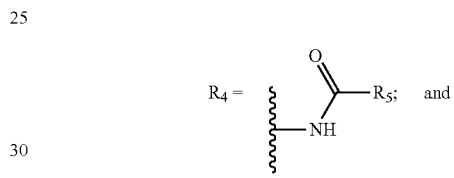
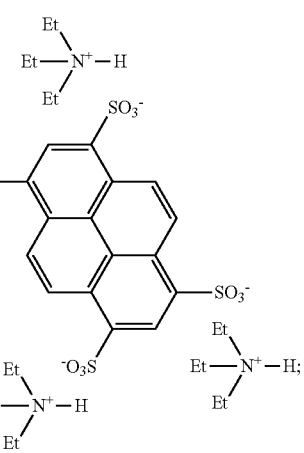
Example 16
Compound of Formula III, wherein
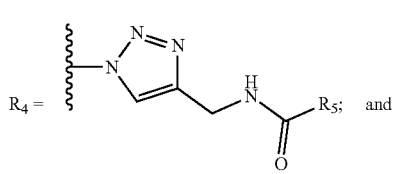

Example 17
Compound of Formula III, wherein
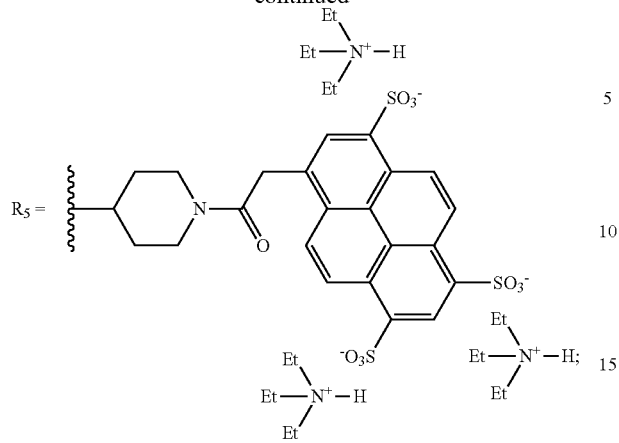
Example 18
Compound of Formula III, wherein
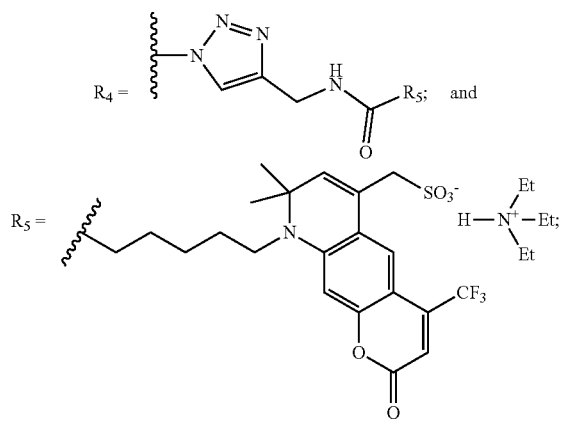
Example 19
Compound of Formula III, wherein
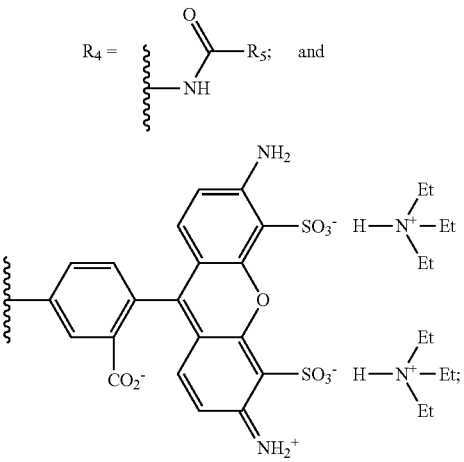
Example 20
Compound of Formula III, wherein
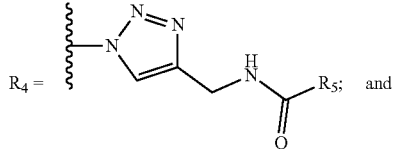
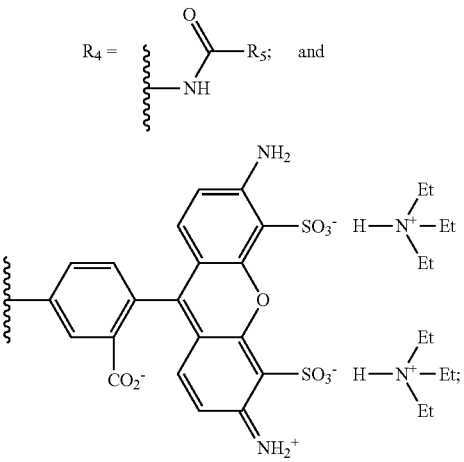
Example 21
Compound of Formula III, wherein
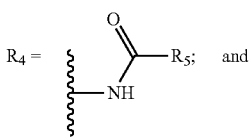

Example 22
Compound of Formula III, wherein
R5 = 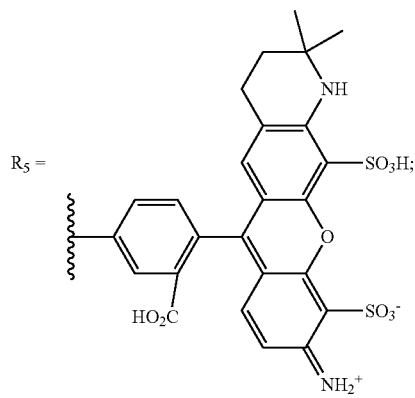
R4 = 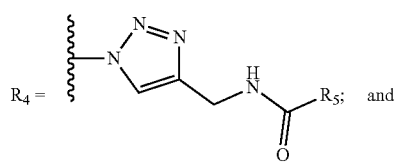; and
Example 23
Compound of Formula III, wherein
R5 = 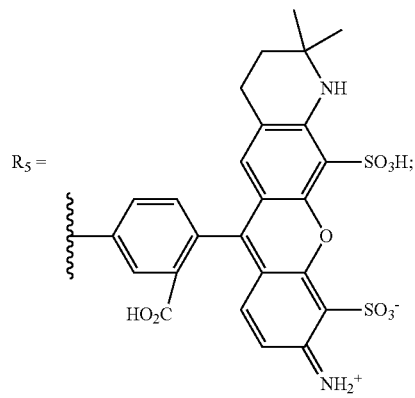
R4 = 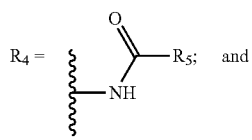; and
Example 24
Compound of Formula III, wherein
R5 = 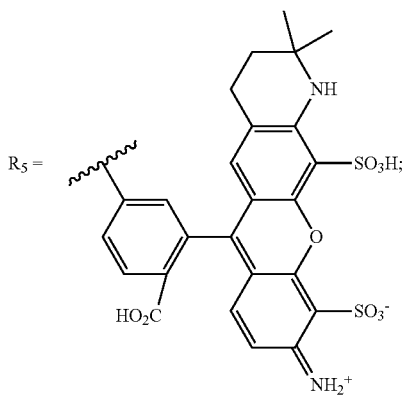
R4 = (same triazole-methylene-amide linker as Example 22); and
Example 25
Compound of Formula III, wherein
R5 = 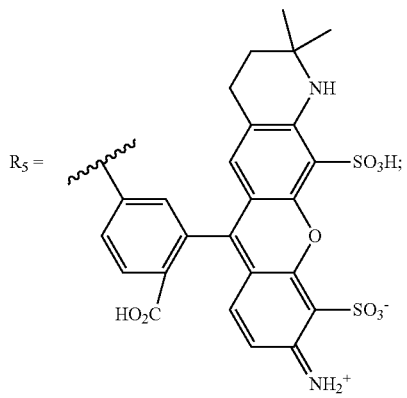
R4 = 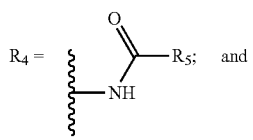; and -continued
R₅ = 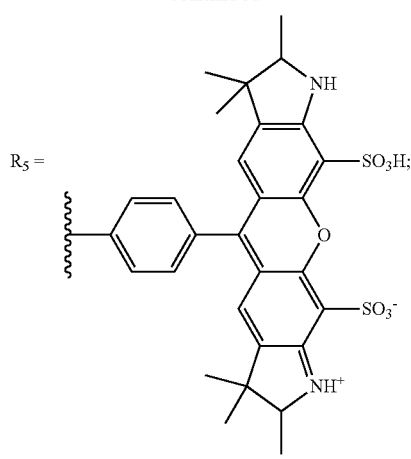
Example 26
Compound of Formula III, wherein
R₄ = 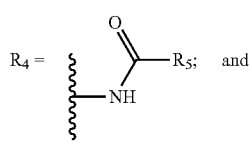; and
-continued
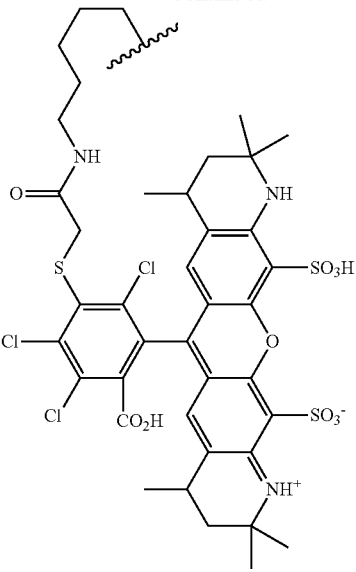
R₅ = 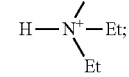
Example 28
Compound of Formula III, wherein
R₄ = ; and
R₅ = 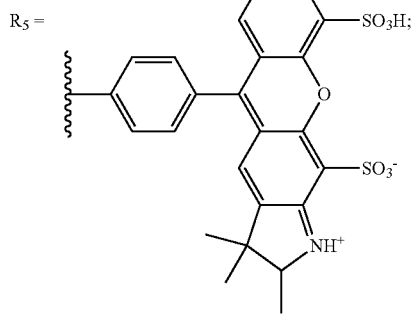
Example 27
Compound of Formula III, wherein
R₄ = (structure shown); and
R₅ = 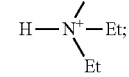
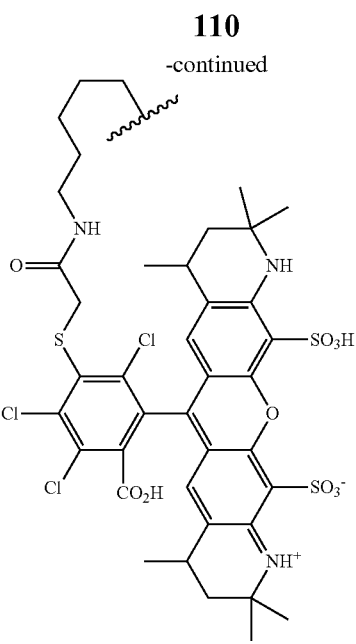

Example 28
Compound of Formula III, wherein
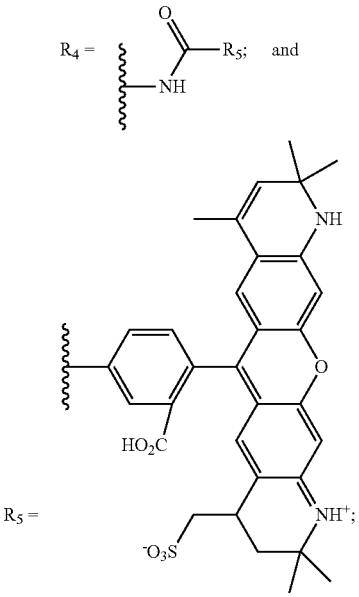
Example 29
Compound of Formula III, wherein
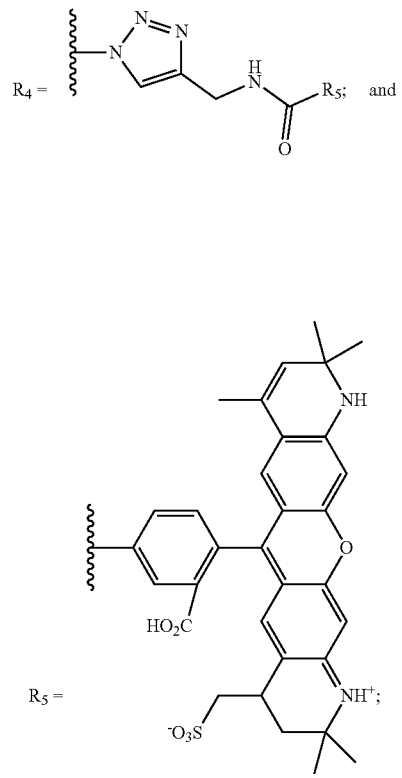
Example 30
Compound of Formula III, wherein
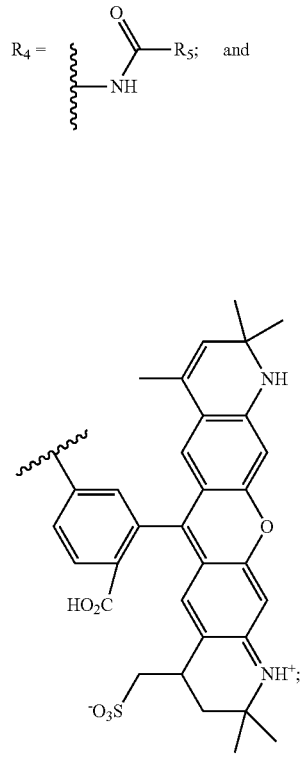
Example 31
Compound of Formula III, wherein
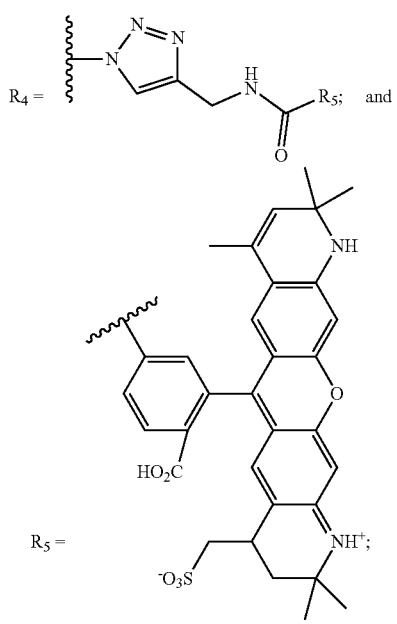

Example 32
Compound of Formula III, wherein
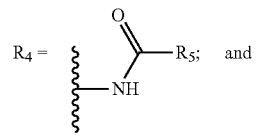
R₄ = ... ; and
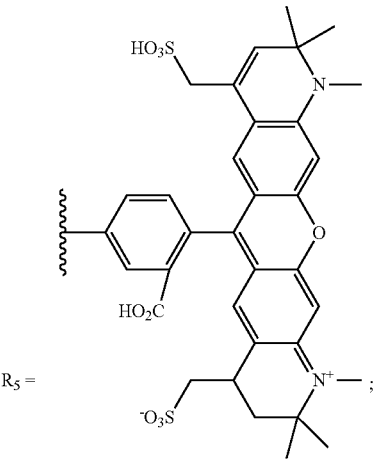
R₅ =
Example 33
Compound of Formula III, wherein
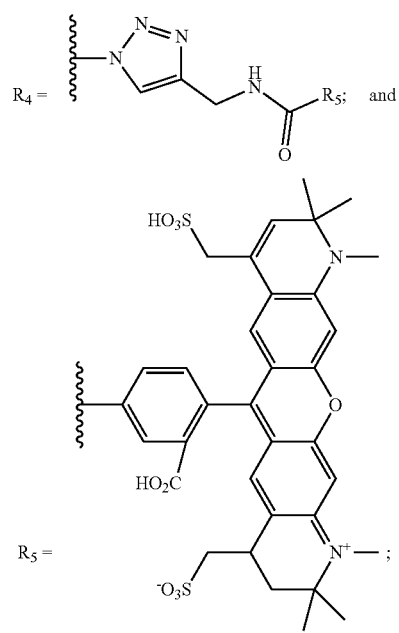
R₄ = ... ; and
R₅ =
Example 34
Compound of Formula III, wherein
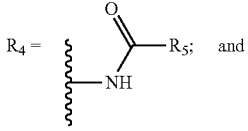
R₄ = ... ; and
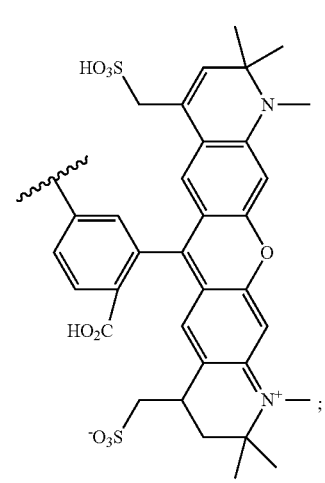
R₅ =
Example 35
Compound of Formula III, wherein
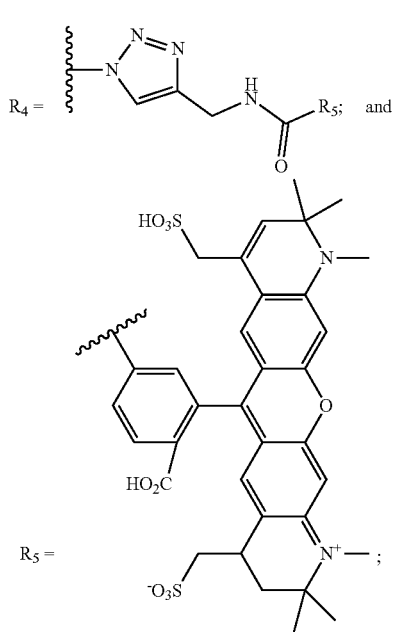
R₄ = ... ; and
R₅ =

Example 36
Compound of Formula III, wherein
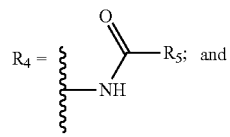
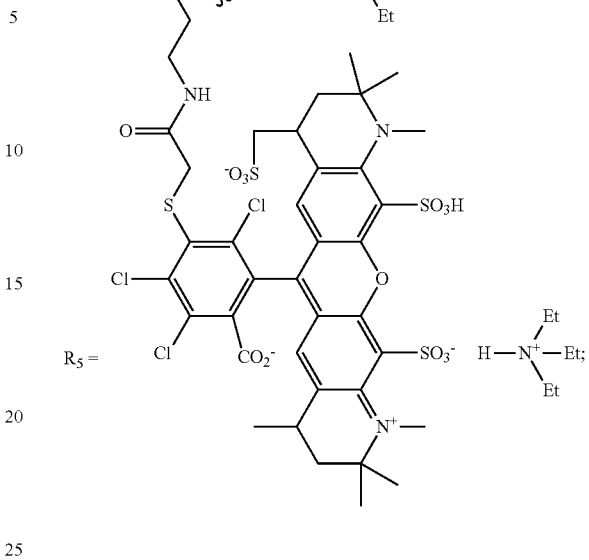
Example 38
Compound of Formula III, wherein
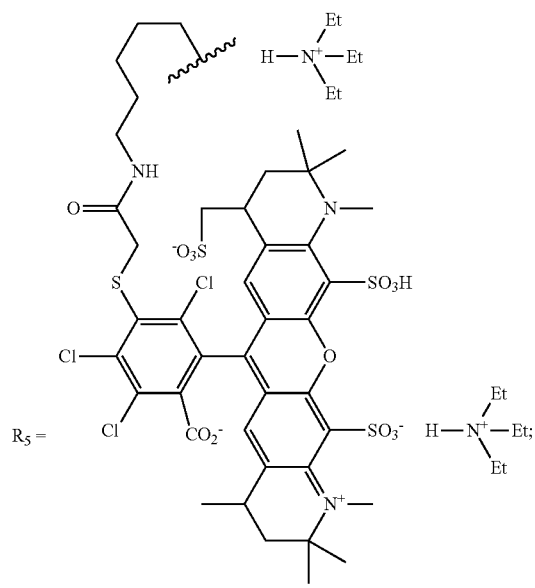
Example 37
Compound of Formula III, wherein
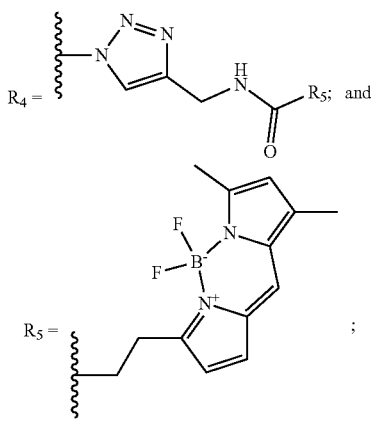
Example 29
Compound of Formula III, wherein
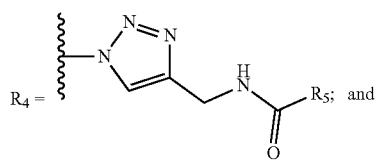

Example 40
Compound of Formula III, wherein
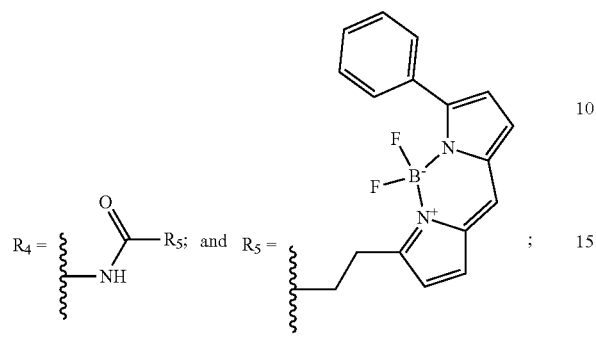
Example 41
Compound of Formula III, wherein
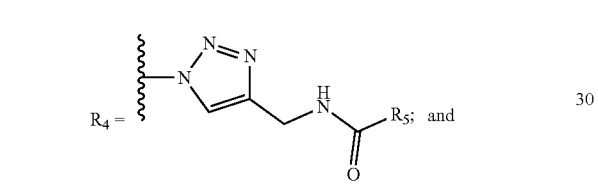
Example 42
Compound of Formula III, wherein
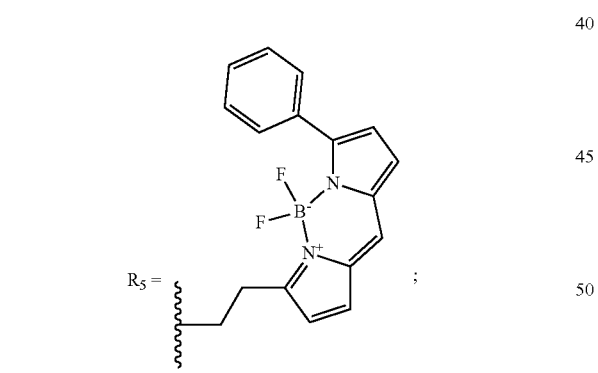
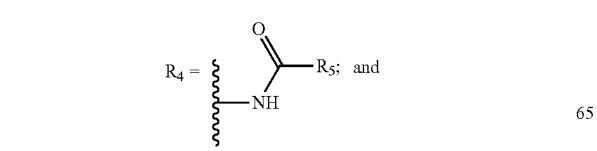
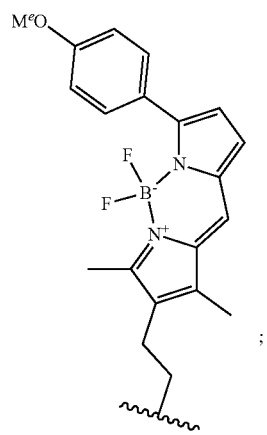
Example 43
Compound of Formula III, wherein
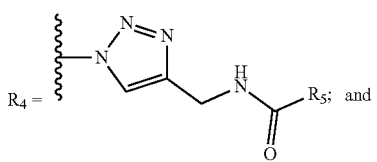
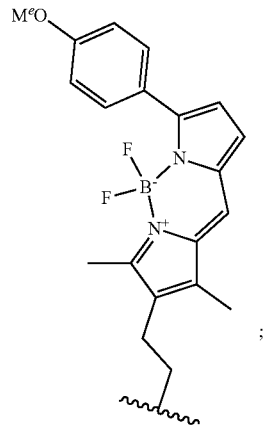

Example 44
Compound of Formula III, wherein
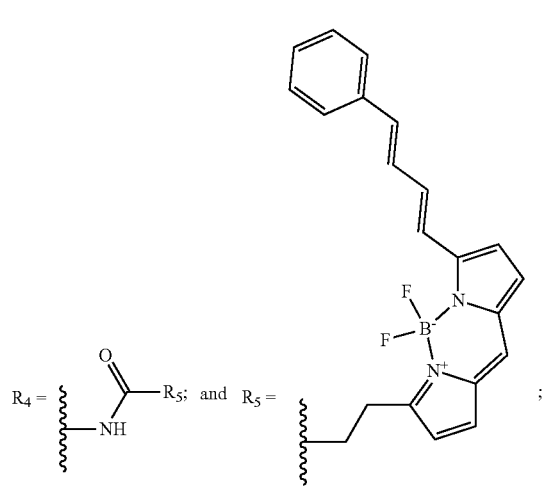
Example 45
Compound of Formula III, wherein
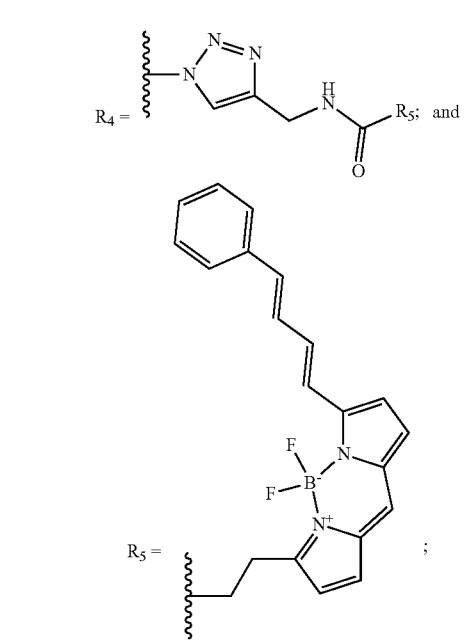
Example 46
Compound of Formula III, wherein
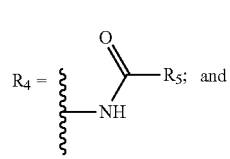
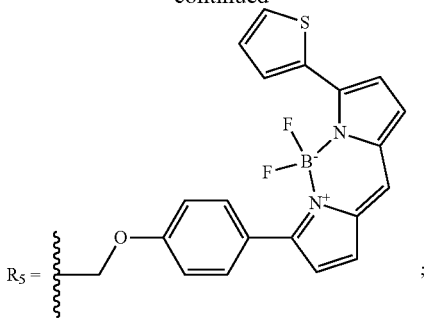
Example 47
Compound of Formula III, wherein
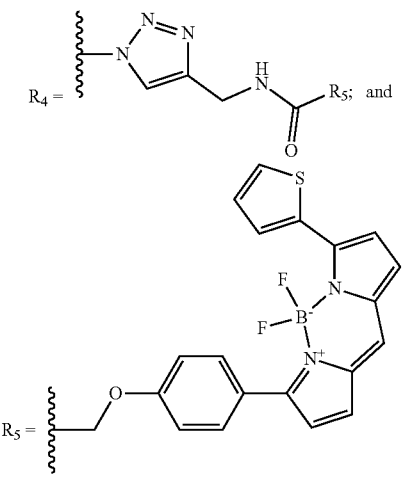
Example 48
Compound of Formula III, wherein
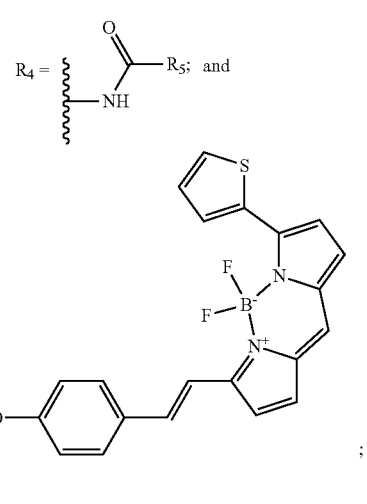

Example 49
Compound of Formula III, wherein
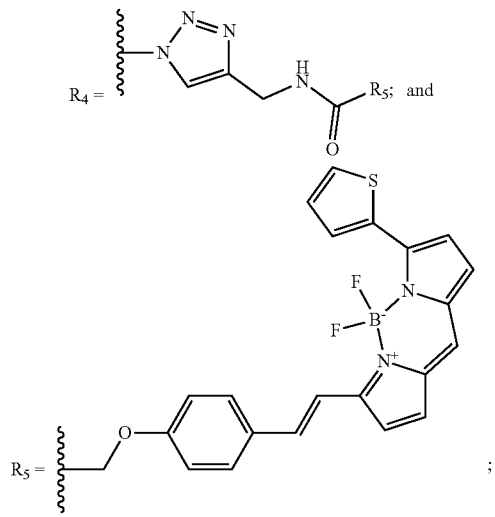
Example 50
Compound of Formula III, wherein
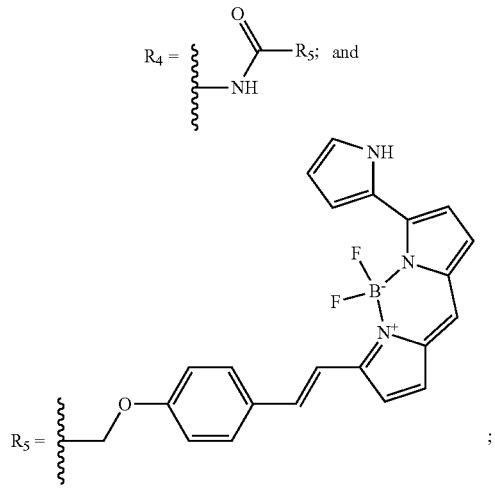
Example 51
Compound of Formula III, wherein
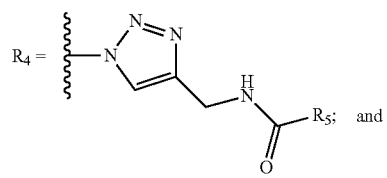
-continued
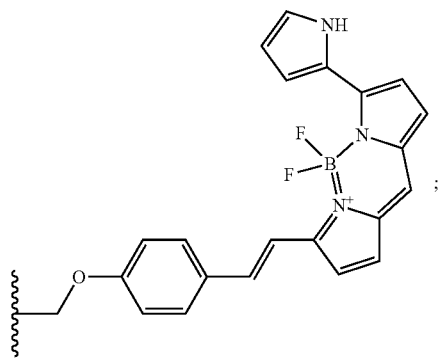
Example 52
Compound of Formula III, wherein
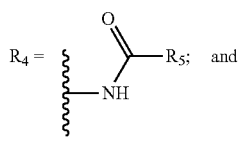
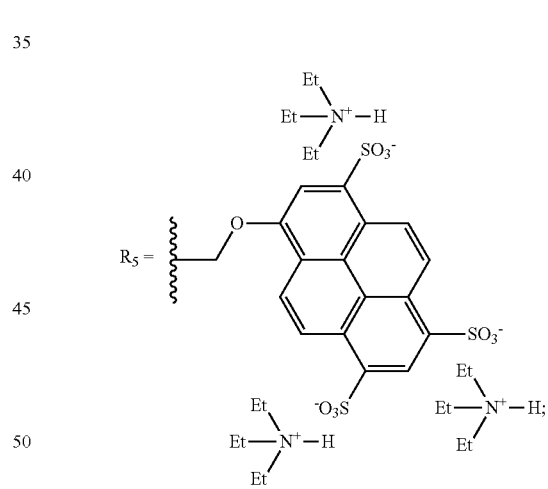
Example 53
Compound of Formula III, wherein
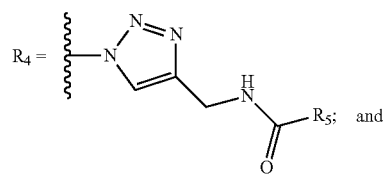

123
-continued
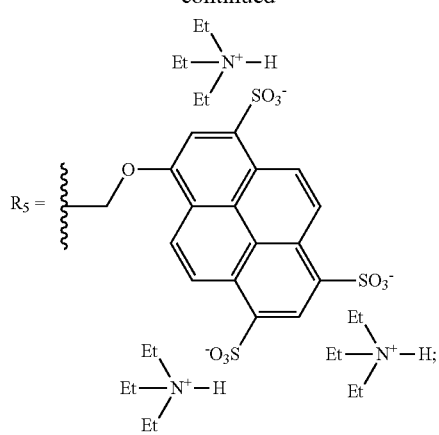
Example 54
Compound of Formula III, wherein
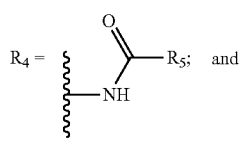
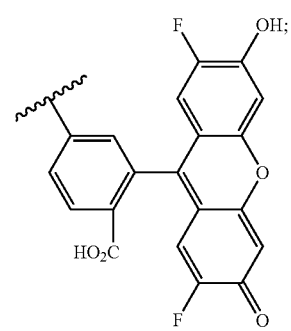
Example 55
Compound of Formula III, wherein
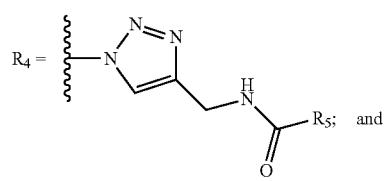
124
-continued
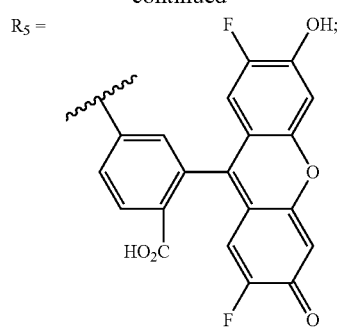
Example 56
Compound of Formula III, wherein
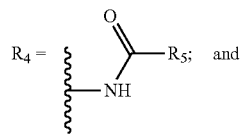
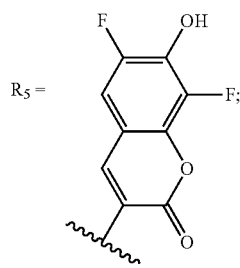
Example 57
Compound of Formula III, wherein
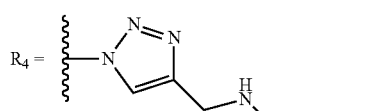
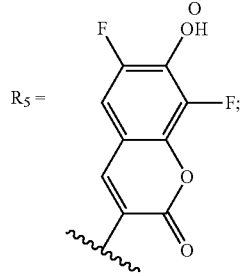

125
Example 58
Compound of Formula III, wherein
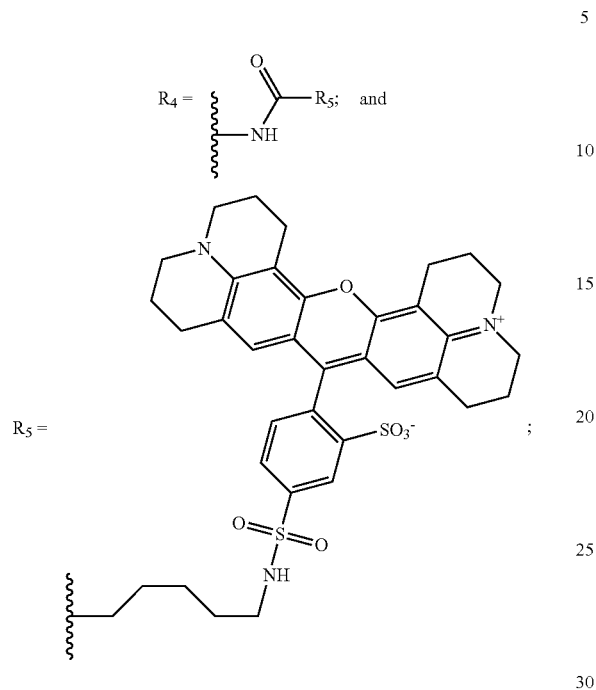
Example 59
Compound of Formula III, wherein
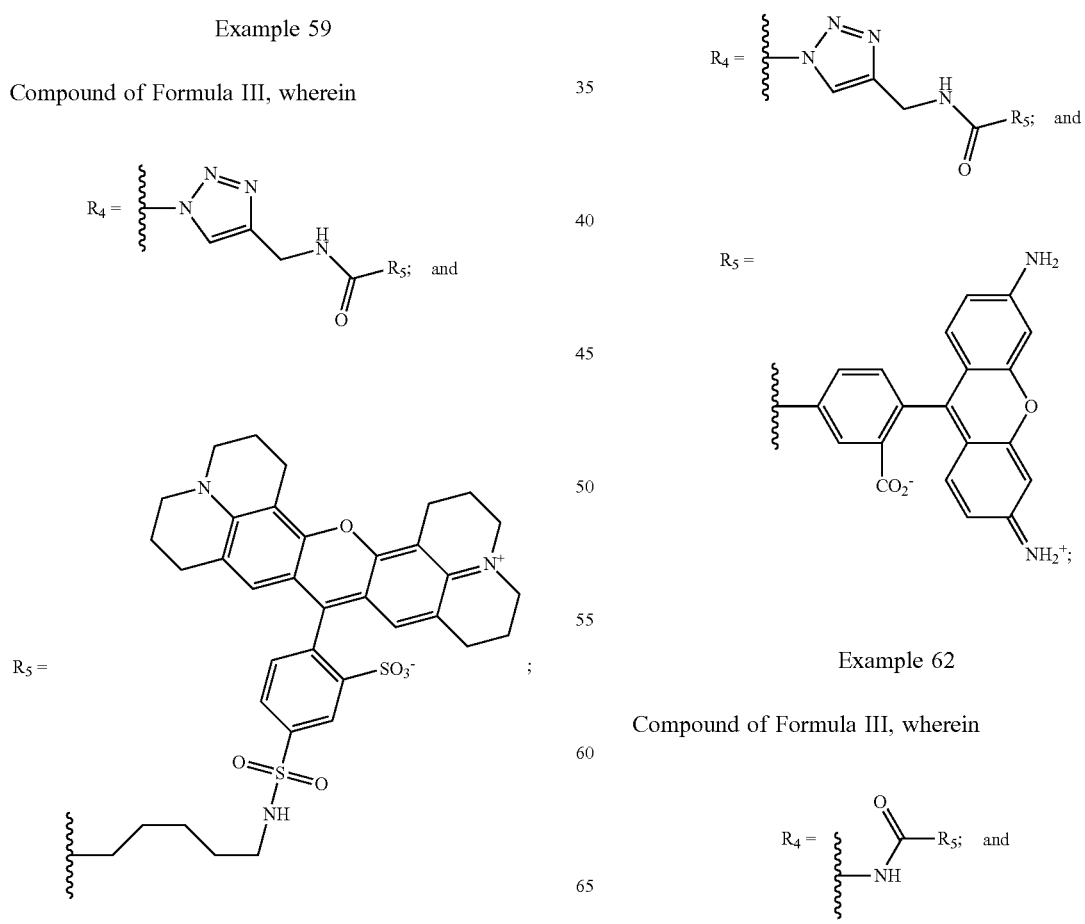
126
Example 60
Compound of Formula III, wherein
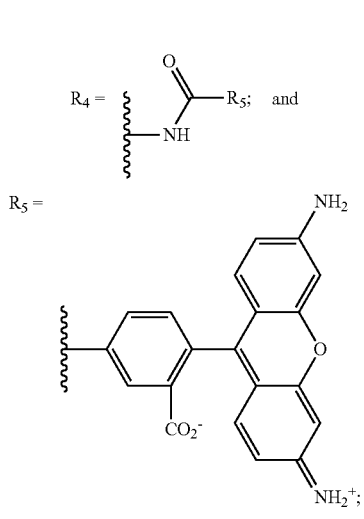
Example 61
Compound of Formula III, wherein
Example 62
Compound of Formula III, wherein -continued
$R_5 =$ 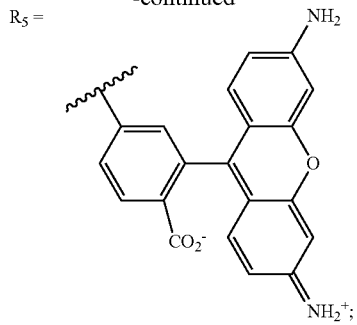
Example 63
Compound of Formula III, wherein
$R_4 =$ 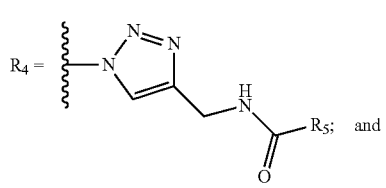 and
$R_5 =$ 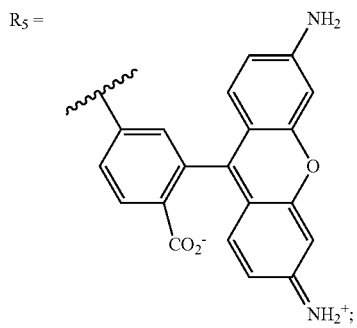
Example 64
Compound of Formula III, wherein
$R_4 =$ 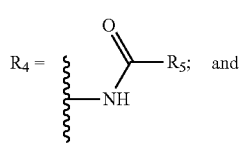 and
-continued
$R_5 =$ 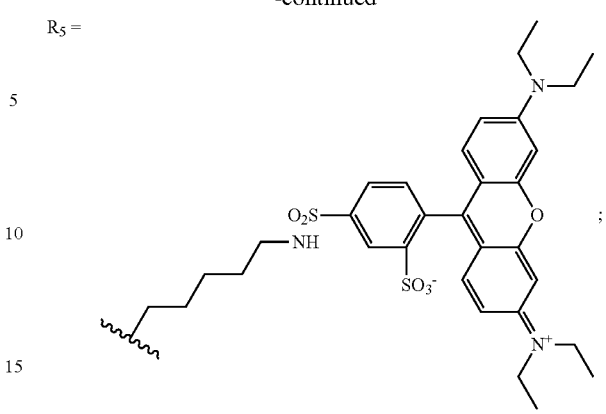
Example 65
Compound of Formula III, wherein
$R_4 =$ 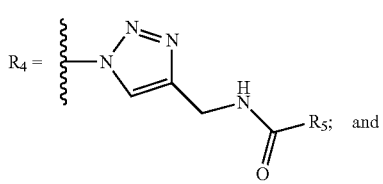 and
$R_5 =$ 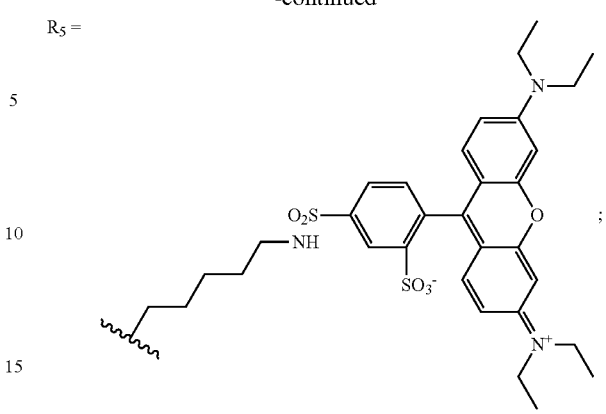
The following compounds of Formula IV can be prepared in accordance with the general procedures presented herein.
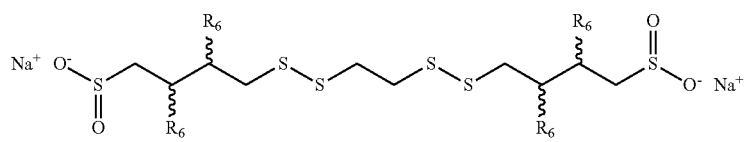
Formula IV Example 66

Compound of Formula IV, wherein

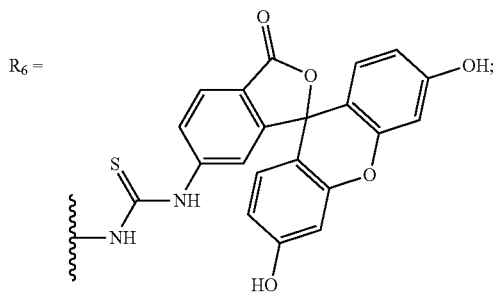 [SMILES: *NC(=S)Nc1ccc2c(c1)C1(OC2=O)c2ccc(O)cc2Oc2cc(O)ccc21]

Example 67

Compound of Formula IV, wherein

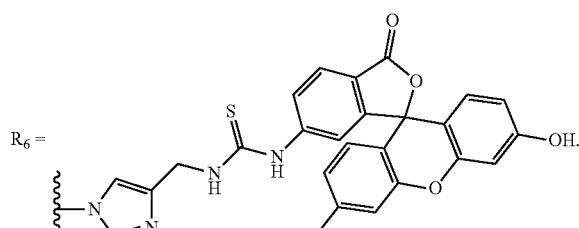

Example 68

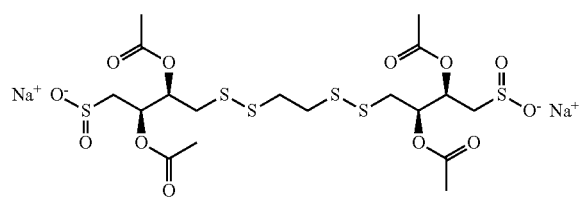 [SMILES: [Na+] ; CC(=O)O[C@@H](CSSCCSSC[C@H](OC(C)=O)[C@H](CS(=O)[O-])OC(C)=O)[C@H](CS(=O)[O-])OC(C)=O ; [Na+]]

sodium (2R,3R)-2,3-diacetoxy-4-((2-(((2R,3R)-2,3-diacetoxy-4-sulfinatobutyl)disulfanyl)ethyl)disulfanyl)butane-1-sulfinate Example 69

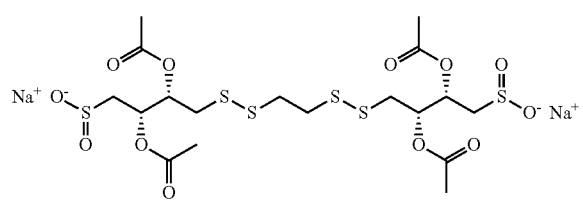 [SMILES: [Na+] ; CC(=O)O[C@H](CSSCCSSC[C@@H](OC(C)=O)[C@@H](CS(=O)[O-])OC(C)=O)[C@@H](CS(=O)[O-])OC(C)=O ; [Na+]]

sodium (2S,3S)-2,3-diacetoxy-4-((2-(((2S,3S)-2,3-diacetoxy-4-sulfinatobutyl)disulfanyl)ethyl)disulfanyl)butane-1-sulfinate Example 70

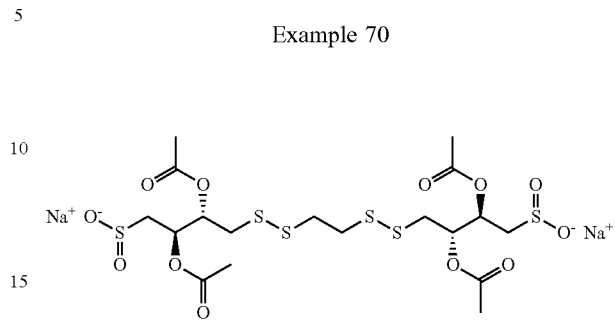

sodium (2S,3R)-2,3-diacetoxy-4-((2-(((2R,3S)-2,3-diacetoxy-4-sulfinatobutyl)disulfanyl)ethyl)disulfanyl)butane-1-sulfinate Example 71

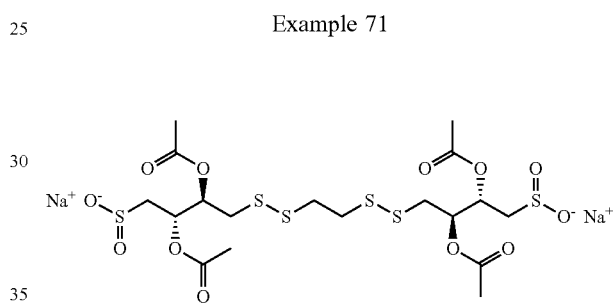

sodium (2R,3S)-2,3-diacetoxy-4-((2-(((2S,3R)-2,3-diacetoxy-4-sulfinatobutyl)disulfanyl)ethyl)disulfanyl)butane-1-sulfinate Example 72

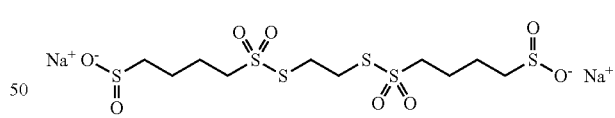

sodium 4-(2-(4-sulfinatobutylsiulfonylthio)ethyltlhiosulfonyl)butane-1-sulfinate Example 73

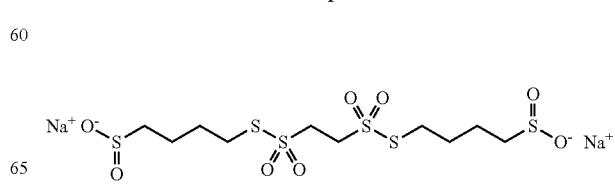

sodium 4-(2-(4-sulfinatobutylthiosulfonyl)ethyl-
sulfonylthio)butane-1-sulfinate Example 74

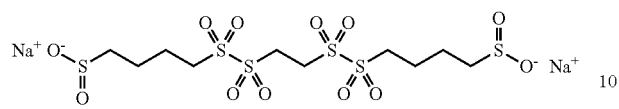

sodium 4-(2-(4-sulfinatobutylsulfonylsulfonyl)ethyl-
sulfonylsulfonyl)butane-1-sulfinate Example 75

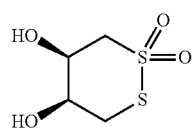

cis-1,2-dithiane-4,5-diol-1,1-dioxide

Example 76

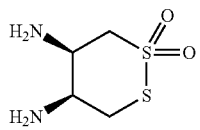

Example 77

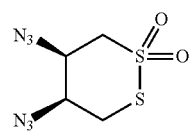

cis-1,2-dithiane-4,5-diazido-1,1-dioxide

Example 78

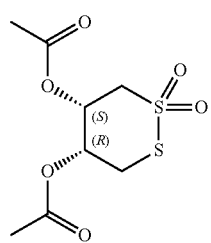

1,2-dithiane-(4R,5S-diacetoxy)-1,1-dioxide

Example 79

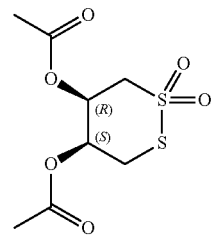

1,2-dithiane-(4S,5R-diacetoxy)-1,1-dioxide

Example 80

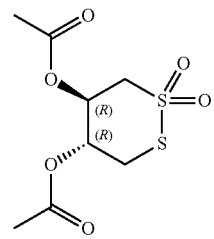

1,2-dithiane-(4R,5R-diacetoxy)-1,1-dioxide

Example 81

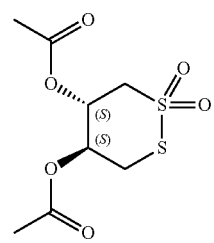

1,2-dithiane-(4S,5S-diacetoxy)-1,1-dioxide

Example 82

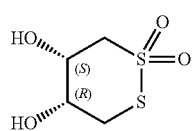

| 133 | 134 |
|---|---|
| 1,2-dithiane-(4R,5S-dihydroxy)-1,1-dioxide | Example 88 |
| Example 83 | 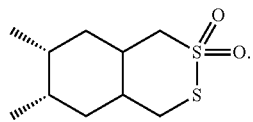 |
| 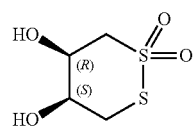 | Example 89 |
| 1,2-dithiane-(4S,5R-dihydroxy)-1,1-dioxide | 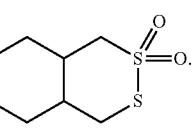 |
| Example 84 | Example 90 |
| 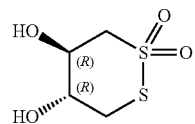 | |
| 1,2-dithiane-(4R,5R-dihydroxy)-1,1-dioxide | |
| Example 85 | Example 91 |
| 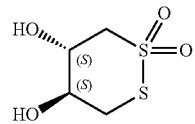 | 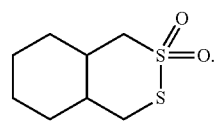 |
| 1,2-dithiane-(4S,5S-dihydroxy)-1,1-dioxide | |
| Example 86 | Example 92 |
| 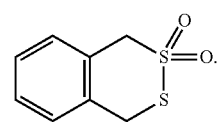 [SMILES: O=S1(=O)Cc2ccccc2CS1] | 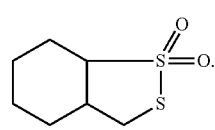 |
| Example 87 | Example 93 |
| 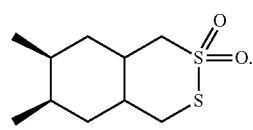 | 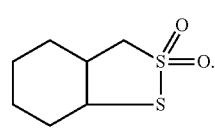 [SMILES: O=S1(=O)CC2CCCCC2S1] |

Example 94

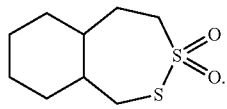 [SMILES: O=S1(=O)CCC2CCCCC2CS1]

Example 95

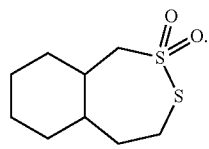 [SMILES: O=S1(=O)CC2CCCCC2CCS1]

Example 96—Synthesis of (±)-DMtcyDTDO (Also Referred to Herein as a Compound of Formula XIX)

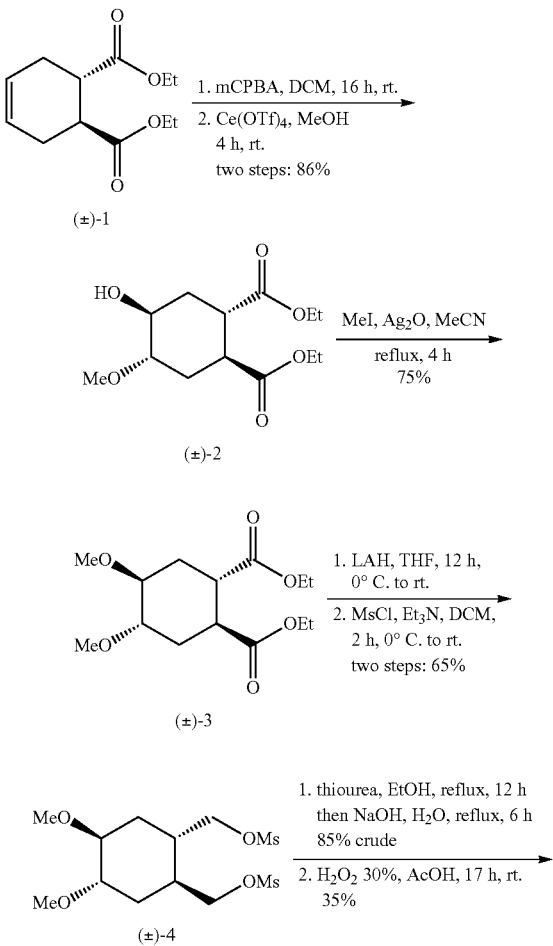

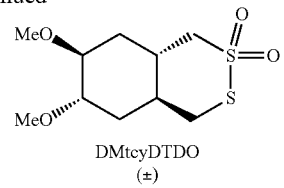

DMtcyDTDO
(±)

Preparation of Diethyl (1S,2S,4S,5S)- and (1R,2R,4R,5R)-4-hydroxy-5-methoxycyclohexane-1,2-dicarboxylate, (±)-2

MCPBA 77% (6.9 g, 31 mmol) was added to a solution of diester (±)-1 (5.0 g, 22 mmol) in anhydrous DCM (85 mL) at 0° C. The solution then was stirred at rt for 16 h, with monitoring by TLC. After reaction completion, the white precipitate was filtered off and saturated NaHSO$_3$ was then added to the filtrate and stirred for 10 min. The organic layer was separated, washed with NaHCO$_3$, dried over Na$_2$SO$_4$, and concentrated to give the crude epoxy diester, which was used without further purification in the next step.

Epoxy diester (5.2 g, 22 mmol, 1.0 equiv) was dissolved in dry MeOH (60 mL) then cat. Ce(OTf)$_4$ (0.6 g, 0.9 mmol, 0.04 equiv) was added. The solution was stirred at rt under Ar atmosphere until the starting material was consumed. After completion of the reaction the solvent was evaporated, water was added, and the crude mixture was extracted with DCM. The combined organic layers were dried over Na$_2$SO$_4$ and concentrated under reduced pressure. The crude material was then purified by flash silica gel column chromatography (0-40% EtOAc/hexanes) to afford the compound (±)-2 (5.2 g, 19 mmol, 86% yield) as a colorless oil. $^1$H NMR (CDCl$_3$, 400 MHz): δ 4.16-4.05 (m, 4H), 3.86-3.83 (m, 1H), 3.35 (s, 3H), 3.27 (q, J=4.9 Hz, 1H), 3.03 (td, J=10.0, 4.2 Hz, 1H), 2.95 (td, J=9.6, 4.2 Hz, 1H), 2.45 (s, 1H), 2.00-1.93 (m, 2H), 1.89 (dt, J=13.9, 4.7 Hz, 1H), 1.82 (dt, J=13.8, 4.8 Hz, 1H), 1.24-1.17 (m, 6H). $^{13}$C NMR (CDCl$_3$, 101 MHz): δ 174.6, 78.4, 67.4, 60.8, 56.7, 39.5, 39.2, 30.7, 26.5, 14.2. HRMS calcd for C$_{13}$H$_{22}$O$_6$ [M+H]$^+$: 275.1489; found: 275.1492.

Preparation of Diethyl (1S,2S,4S,5S)- and (1R,2R,4R,5R-4,5-dimethoxycyclohexane-1,2-dicarboxylate, (±)-3

Silver (I) oxide (8.8 g, 38 mmol) was added to a solution of compound (±)-2 (5.2 g, 19 mmol) and iodomethane (11.8 mL, 190 mmol) in acetonitrile (50 mL), then the mixture was heated to reflux for 4 h. After completion of the reaction the solid residue was removed by filtration. An aqueous NaHCO$_3$ solution was added and the reaction mixture was extracted with ethyl acetate, washed with brine, dried over Na$_2$SO$_4$, and concentrated under reduced pressure. The crude material was purified by flash silica gel column chromatography (0-20% EtOAc/hexanes) to afford the desired product (±)-3 (4.1 g, 14 mmol, 75% yield) as a white solid. $^1$H NMR (CDCl$_3$, 400 MHz): δ 4.26-4.00 (m, 411), 3.46-3.42 (m, 2H), 3.36 (s, 6H), 2.92-2.82 (m, 2H), 2.07 (d, J=14.0 Hz, 2H), 1.80-1.69 (m, 2H), 1.22 (t, J=7.1 Hz, 6H). $^{13}$C NMR (CDCl$_3$, 101 MHz,) δ 175.0, 75.4, 60.6, 56.6, 39.0, 27.0, 14.3. HRMS calcd for C$_{14}$H$_{24}$O [M+H]$^+$: 289.1651; found: 289.1650.

Preparation of ((1S,2S,4S,5S)- and (1R,2R,4R,5R)-4,5-Dimethoxycyclohexane-1,2-diyl)bis(methylene) dimethanesulfonate, (±)-4

To an ice-cooled solution of compound (±)-3 (4.4 g, 15 mmol) in anhydrous THF (85 mL) was added LiAlH$_4$ (1.7 g, 46 mmol) in small portions then the reaction mixture was stirred for 8 h at rt. After this time water was added dropwise, and the white precipitate formed was filtered through celite and washed with DCM. The filtrate was extracted with DCM, and the combined organic extracts were dried over $Na_2SO_4$, filtered, and concentrated to give the diol (2.8 g, 14 mmol, 90% yield) which was used without further purification in the next step.

A solution of the diol (1.5 g, 7.3 mmol) in anhydrous DCM (70 mL) was cooled to 0° C. and treated with triethylamine (4.0 mL, 29 mmol) followed by methanesulfonyl chloride (2.8 mL, 37 mmol). The reaction mixture was stirred at 0° C. for 15 min, then at rt for 2 h. After completion of the reaction, water was added, and the reaction mixture was extracted with DCM (3×50 mL). The combined organic layers were dried over $Na_2SO_4$, filtered, and concentrated. The crude material was purified by flash silica gel column chromatography (0-50% EtOAc/hexanes) to afford the desired dimesylate (±)-4 (1.9 g, 5.3 mmol, 72%) as a pale yellow solid. $^1H$ NMR (CDCl$_3$, 400 MHz) δ 4.26 (dd, J=10.2, 4.1 Hz, 2H), 4.11 (dd, J=10.2, 3.1 Hz, 2H), 3.47-3.43 (m, Hz, 2H), 3.32 (s, 6H), 3.01 (s, 6H), 2.00-1.94 (m, 2H), 1.89-1.74 (m, 2H), 1.72-1.61 (m, 1H). $^{13}C$ NMR (CDCl$_3$, 101 MHz) δ 75.4, 71.7, 56.7, 37.3, 32.5, 27.7. HRMS calcd for $C_{12}H_{24}O_8S_2$ $[M+Na]^+$. 383.0805; found: 383.0805.

Preparation of (4aS,6S,7S,8aS)- and (4aR,6R,7R, 8aR)-6,7-Dimethoxyoctahydrobenzo[d][1,2]dithiine 2,2-dioxide, (±)-DMtcyDTDO (Also Referred to Herein as a Compound of Formula XIX)

Thiourea (0.76 g, 10 mmol) was added to the solution of compound (±)-4 (1.45 g, 4.03 mmol) in EtOH (10 mL) and heated to reflux in an open flask for 8 h. EtOH was then removed under vacuum and the residue was dissolved in $H_2O$ (20 mL) and a solution of NaOH (0.64 g, 16 mmol) in $H_2O$ (6 mL) was added. The mixture was heated to reflux for 6 h, cooled to rt, acidified with HC, and extracted with DCM. The combined organic extracts were dried over $Na_2SO_4$ and evaporated to afford (i)-(4,5-dimethoxycyclohexane-1,2-diyl)dimethanethiol as a pale yellow oil (0.8 g, 3 mmol, 85% yield). which was used without further purification for the next step.

To an ice-cooled solution of the crude dithiol (0.8 g, 3 mmol) in AcOH (5.0 mL) was added a solution of $H_2O_2$ in AcOH (0.9 mL of aqueous 30% 1122 diluted in 1.5 mL of AcOH, 9 mmol of $H_2O_2$) and stirred under nitrogen, monitoring by TLC. After stirring for 17 h, the solvent was removed under vacuum, and the residue was diluted with water, neutralized with $NaHCO_3$, and extracted with $CHCl_3$. The organic extract was dried with $Na_2SO_4$, filtered, and the solvent was removed under vacuum. The crude material was purified by column chromatography (10-40% EtOAc/hexanes) to afford the desired product (±)-DMtcyDTDO (0.32 g, 1.2 mmol, 35% yield) as a white solid. $^1H$ NMR (CDCl$_3$, 400 MHz): δ 3.50 (q, J=2.8 Hz, 1H), 3.43 (q, J=2.8 Hz, 1H), 3.35 (s, 3H), 3.34 (s, 3H), 3.30 (dd, J=14.2, 11.7 Hz, 1H), 3.23-3.10 (m, 2H), 2.82 (dd, J=14.2, 2.9 Hz, 1H), 2.44 (qt, J 11.8, 3.8 Hz, 1H), 1.92 (qt, J=11.6, 3.2 Hz, 1H), 1.80 (dt, J=13.8, 3.0 Hz, 1H), 1.67 (dt, J=13.8, 3.1 Hz, 1H), 1.62-1.47 (m, 2H). $^{13}C$ NMR (CDCl$_3$, 101 MHz) δ 76.2, 74.4, 64.4, 56.8, 56.8, 39.8, 35.9, 35.6, 31.1, 30.1. HRMS calcd for $C_{10}H_{18}O_4S_2$ $[M+Na]^+$. 289.0539; found: 289.0527.

Example 97—MTT Assay

MTT cell viability was evaluated using MTT (3-(4,5-dimethylthiazol-2-yl)-2,5-diphenyltetrazolium bromide) assays carried out based on the manufacturer's instructions (kit CGD1, Sigma-Aldrich, St. Louis, MO). The assay results demonstrate that TcyDTDO was the most potent compound identified so far in reducing cancer cell viability (FIG. 1).

Example 98—Protein Thiolate Reactivity Assay

Figure 2:
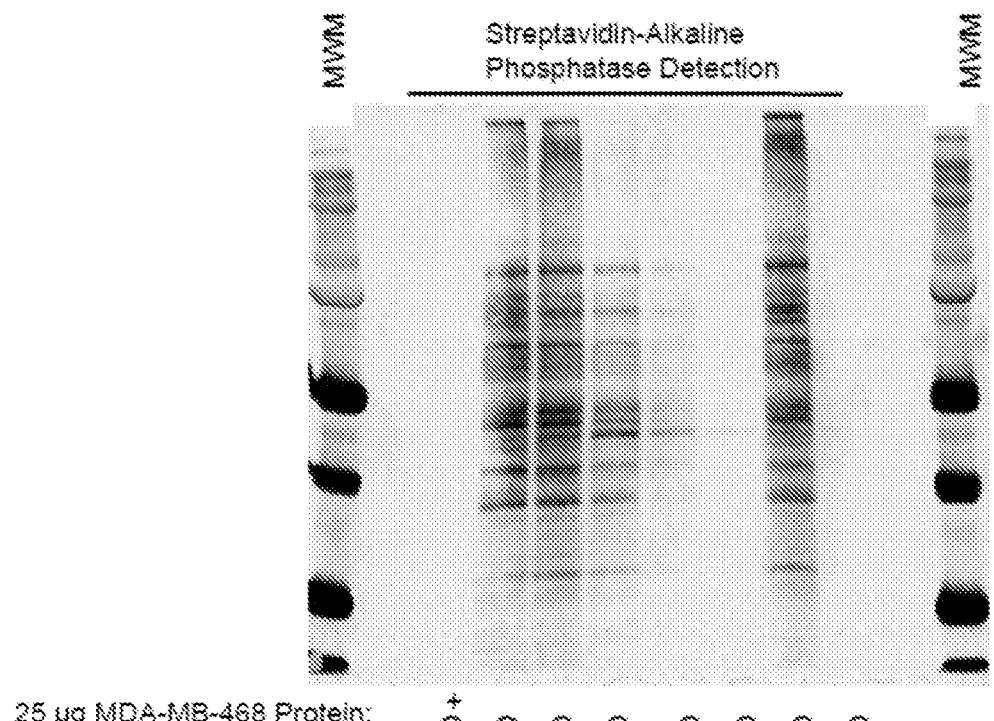
FIG. 2. depicts pretreatment of protein extracts with various compounds of the invention.
Figure 2:
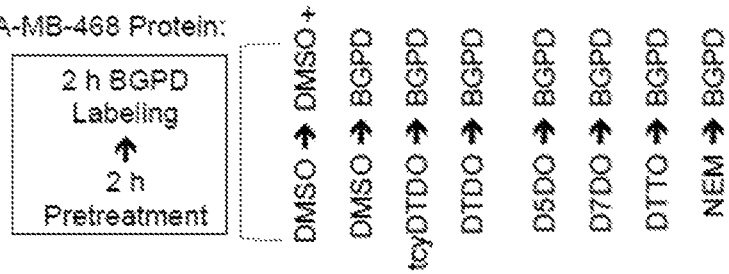
Figure 2:
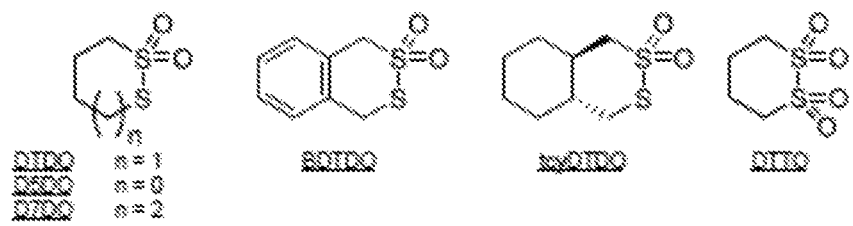
Figure 2:
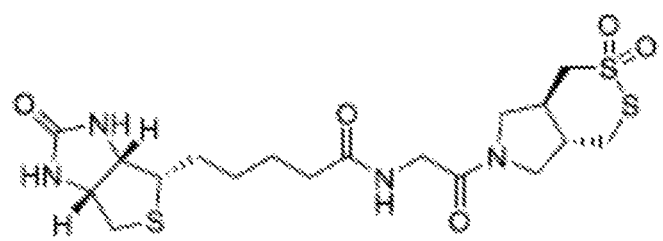

To assess tcyDTDO reactivity with protein thiolates, MDA-MB-468 cell lysates were treated with various compounds in sufficient molar excess to block all protein thiolates. A non-selective thiol-reactive biotinylated analog (BGPD, FIG. 2) was then added to quantify free thiolates remaining after the pre-labeling. The positive control for blocking protein thiols, N-ethylmaleimide (NEM), prevented BGPD labeling. DTTO, which in control experiments exhibited low reactivity with thiolates and is not toxic to cancer cells, did not interfere with BGPD labeling. However, the more strained and reactive compounds, D5DO and D7DO, did interfere with BGPD labeling, while the less strained tcyDTDO did not reduce BGPD labeling.

Example 99—Immunoblot Assays

Figure 3:
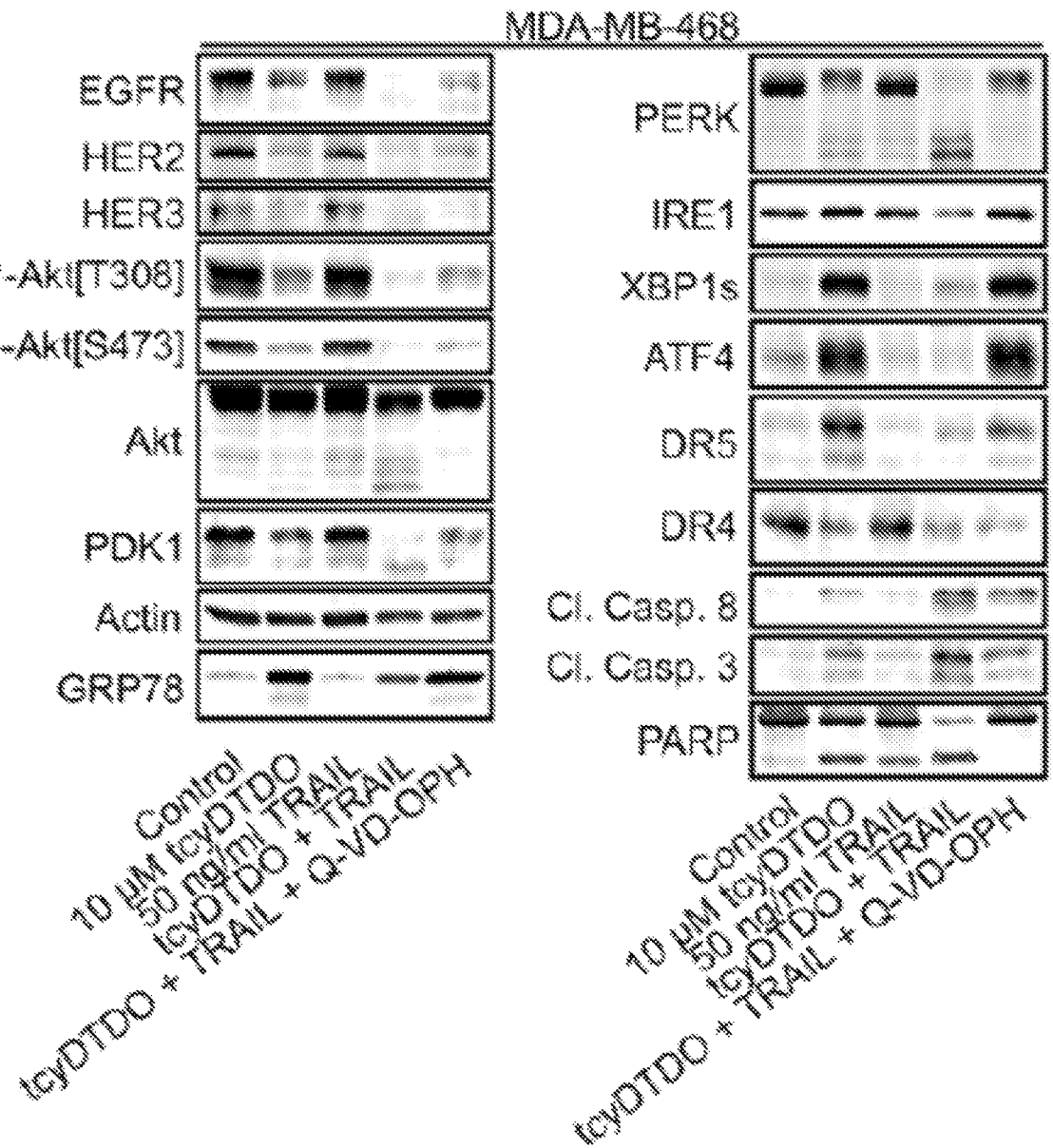
FIG. 3. depicts the induction of PARP and Caspase 8 cleavage by TcyDTDO and TRAIL in MDA-MB-468 cells.
Figure 4:
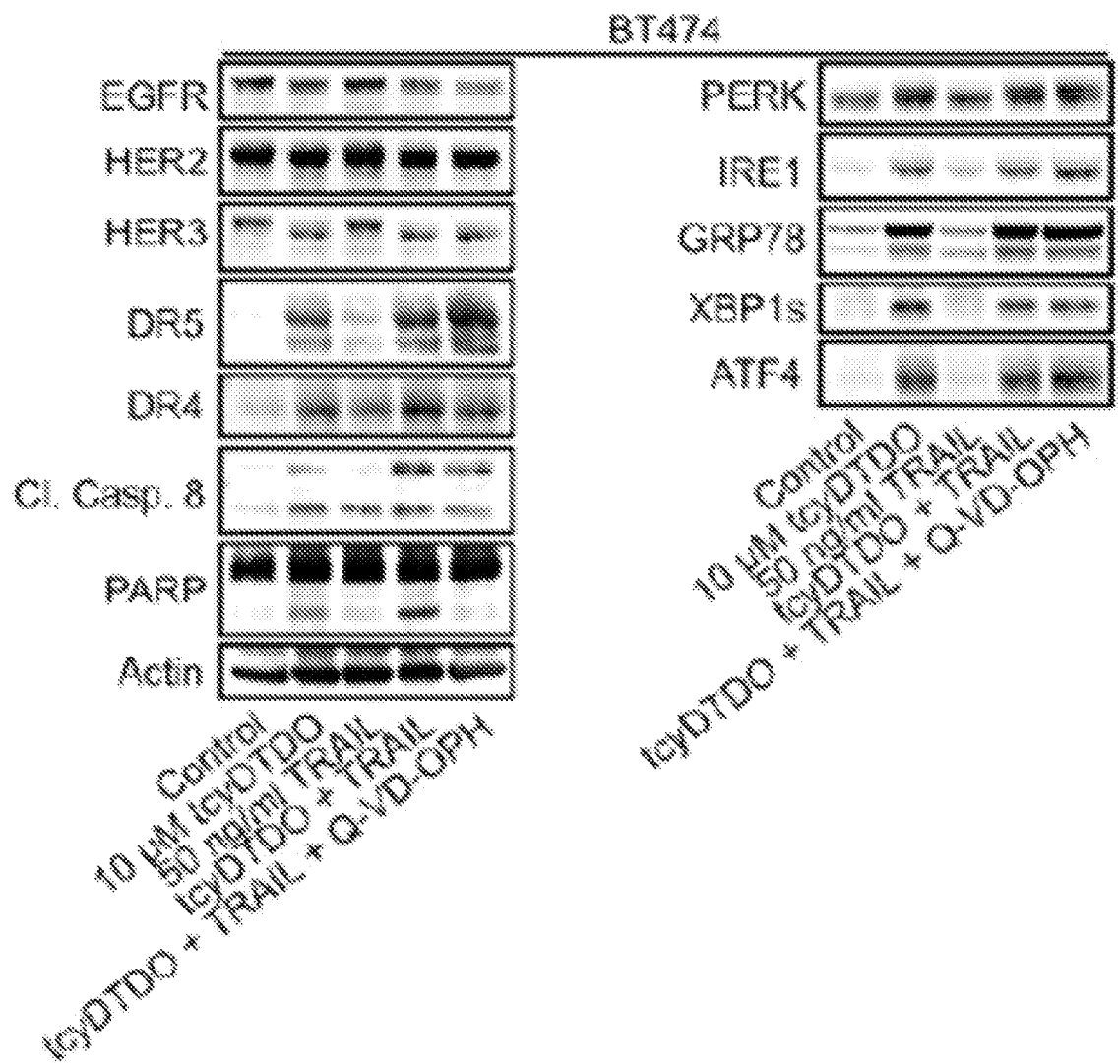
FIG. 4. depicts the induction of PARP and Caspase 8 cleavage by TcyDTDO and TRAIL in BT474 cells.

The ECFR±MDA-MB-468 TNBC line and the HER2±cancer line BT474 both harbor MYC amplification [A. Shadeo, W. L. Lam, Comprehensive copy number profiles of breast cancer cell model genomes, *Breast Cancer Res*, 8 (2006) R9], and are highly responsive to tcyDTDO, TRAIL, and tcyDTDO+TRAIL treatment. TcyDTDO and TRAIL cooperate to induce PARP and Caspase 8 cleavage in MDA-MB-468 (FIG. 3) and BT474 (FIG. 4) cells. PARP cleavage is blocked by Q-VD-OPH, a caspase inhibitor, but Q-VD-OPH does not alter tcyDTDO-mediated upregulation of DR5 or the ER stress response. Q-VD-OPH also partially reverses the tcyDTDO/TRAIL downregulation of EGFR, Akt, phospho-Akt, and the Akt kinase PDK1 in MDA-MB-468 cells. These results suggest that commitment tcyDTDO/TRAIL-induced apoptosis may be insured by caspase-dependent degradation of multiple elements of the HER1-3/PI3K/PDK1/Akt survival cascade. TcyDTDO effects correlate closely with increased DR5 expression, which is consistent with increased TRAIL responsiveness.

Figure 5:
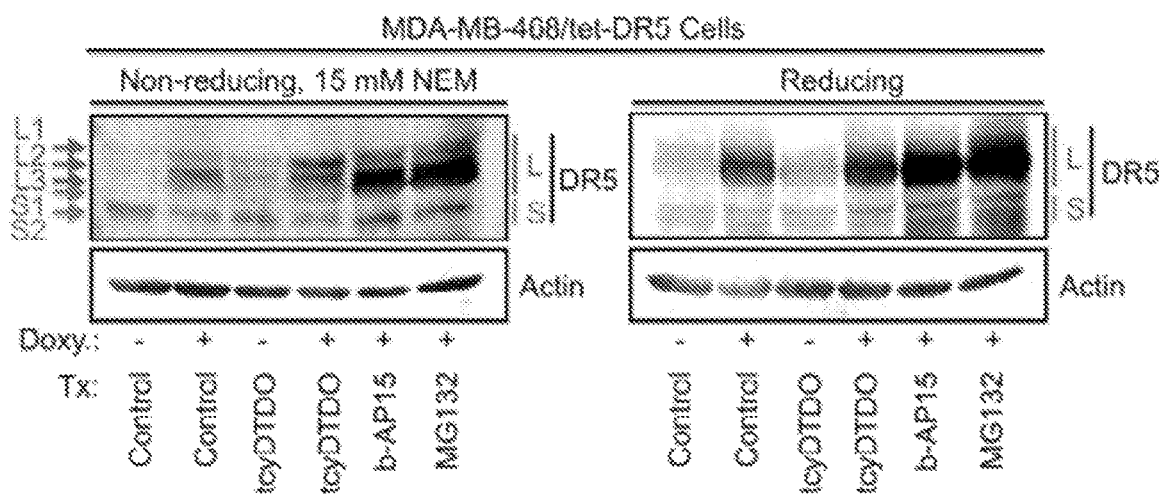
FIG. 5. depicts the doxycycline-inducible DR5 expression of MDA-MB-468 cells by TcyDTDO under reducing and non-reducing conditions.

A MDA-MB-468 cell line was engineered to stably express the long form of DR5 (DR5Long) in a tetracycline-inducible manner in order to separate DR5A effects on DR5 protein stability from transcriptional activation. TcyDTDO enhanced the doxycycline-mediated increase in DR5Long in samples analyzed under reducing conditions (FIG. 5). Increased DR5 expression is not due to the induction of ER stress since the ER stressors, Thapsigargin, Tunicamycin, Dithiothreitol (DTT), and Cyclosporine A (CsA) did not mimic the effects of tcyDTDO.

Figure 6:
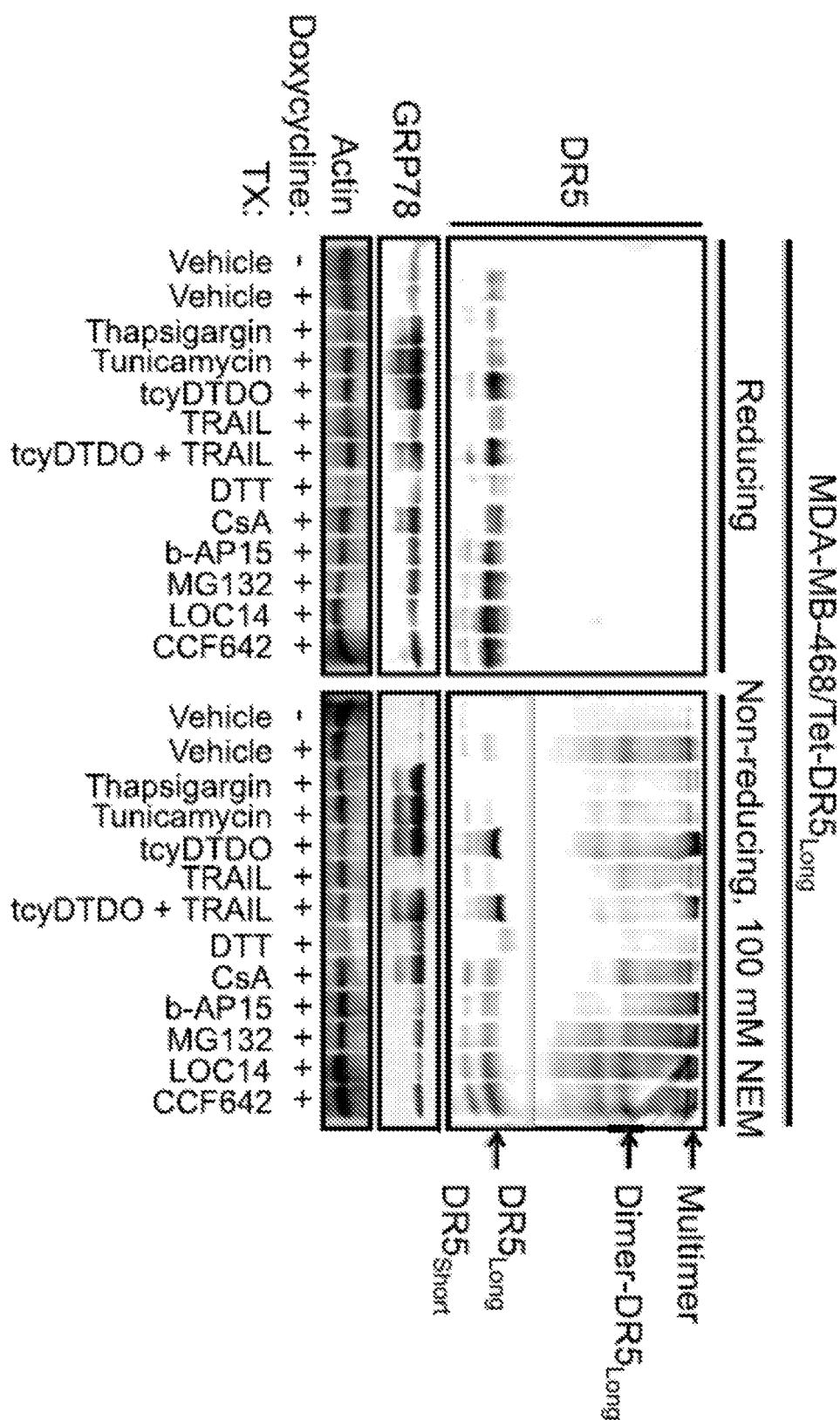
FIG. 6. depicts tcyDTDO mediated DR5 dimerization and oligomerization in MDA-MB-468 cells.
Figure 7:
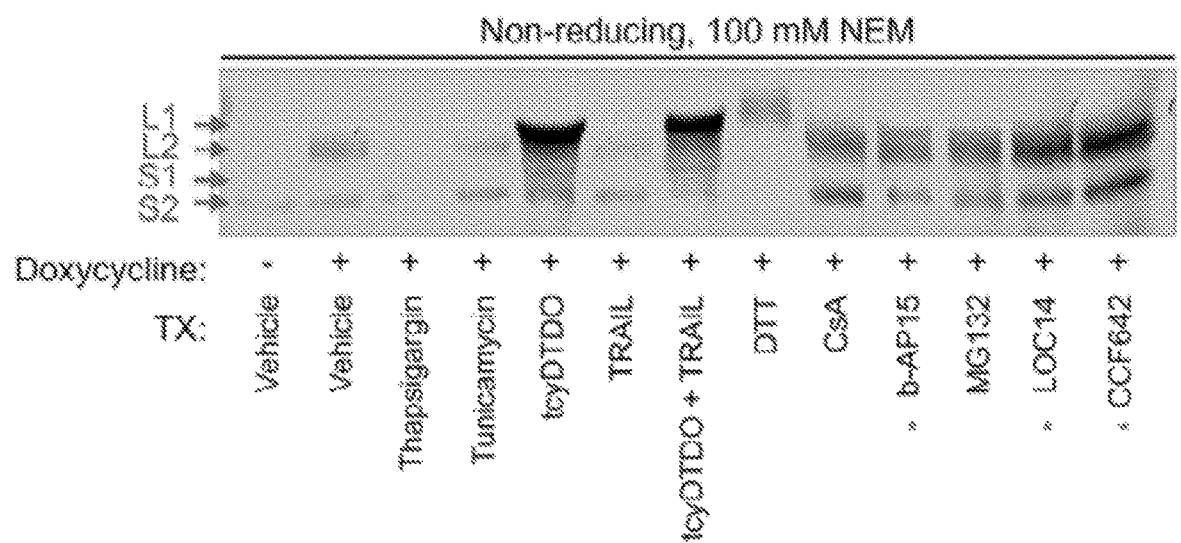
FIG. 7. depicts TcyDTDO enhancement of the doxycycline-mediated increase in DR5Long in samples analyzed under non-reducing conditions.

Oligomerization of DR5 was also investigated in MDA-MB-468 cells as shown in FIG. 6 and FIG. 7, which is a magnification of the $DR5_{Long}/DR5_{Short}$ portion of the immunoblot in FIG. 6. As demonstrated in FIGS. 6 and 7, tcyDTDO administration leads to an increase in DR5 dimerization and oligomerization.

Cell viability assays were performed in MDA-MB-468 (FIG. 8) and BT474 (FIG. 9) cell lines in the presence of increasing concentrations of tcyDTDO and/or TRAIL using the MTT method. The results were analyzed using the Chou-Talalay method [T. C. Chou, P. Talalay, Generalized equations for the analysis of inhibitions of Michaelis-Menten and higher-order kinetic systems with two or more mutually exclusive and nonexclusive inhibitors, *Eur J*

Figure 8:
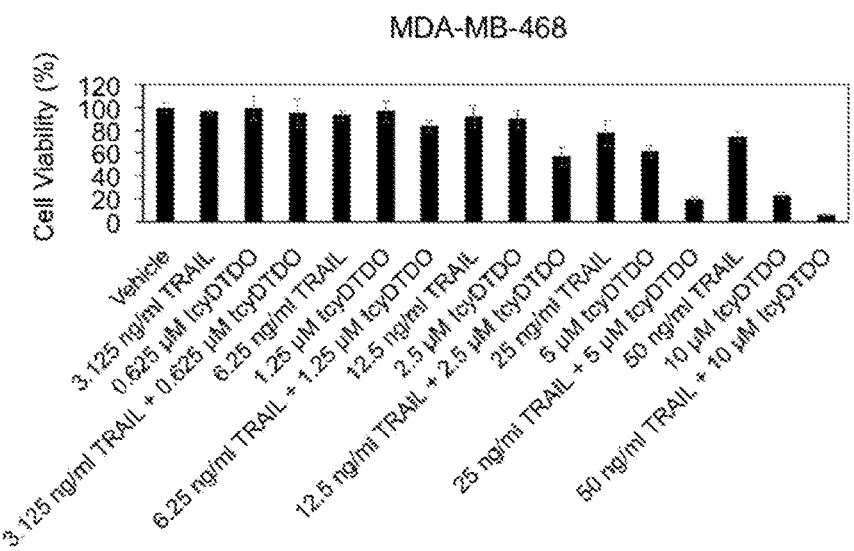
FIG. 8. depicts cell viability assays in MDA-MB-468 cells using various compounds and compound combinations of the invention.
Figure 9:
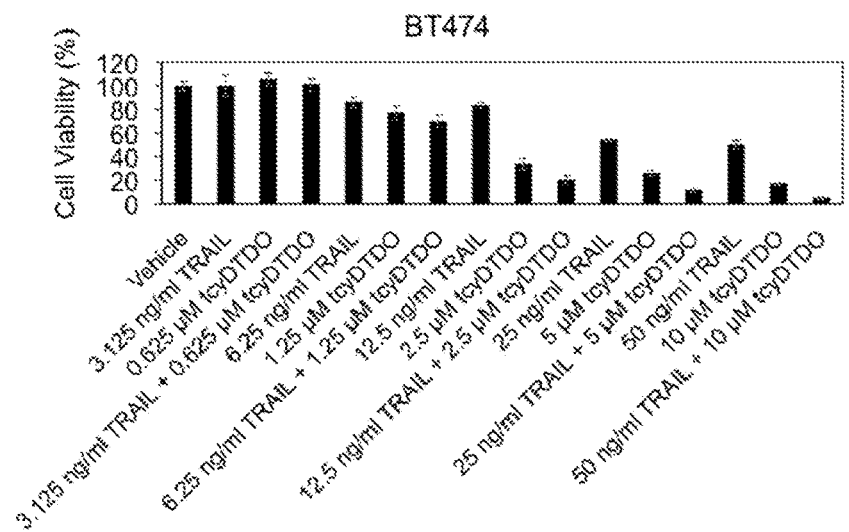
FIG. 9. depicts cell viability assays in BT474 cells using various compounds and compound combinations of the invention.

*Biochem,* 115 (1981) 207-216; T. C. Chou, P. Talalay, Quantitative analysis of dose-effect relationships: the combined effects of multiple drugs or enzyme inhibitors, *Adv Enzyme Regul,* 22 (1984) 27-55.] to calculate combination indices (Cis) where CI<1 denotes synergy, CI=1 denotes additivity, and C I>1 denotes antagonism. FIGS. 8 and 9 clearly demonstrate synergistic effects on cell viability with the combination of tcyDTDO and TRAIL.

Figure 12:
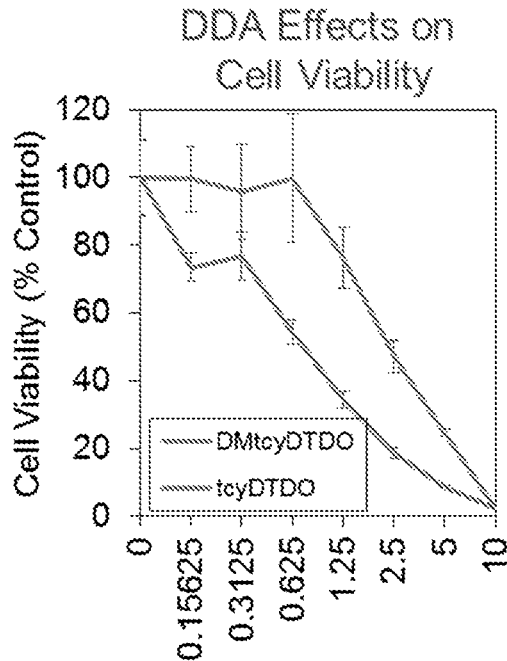
FIG. 12. depicts cell viability of MDA-MB-468 breast cancer cells after 24 treatment with tcyDTDO or DMtcyDTDO.
Figure 13:
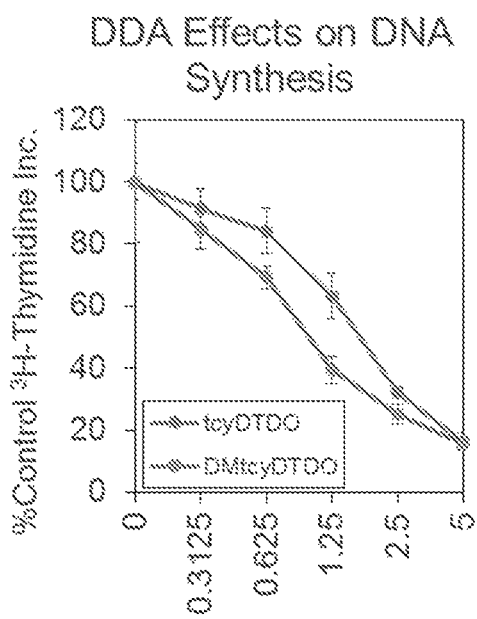
FIG. 13. depicts cell proliferation of MDA-MB-468 breast cancer cells after 24 treatment with tcyDTDO or DMtcyDTDO.
Figure 14:
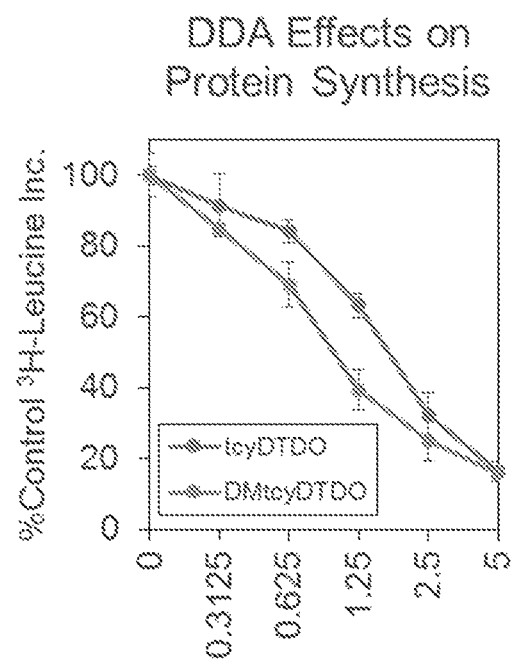
FIG. 14. depicts protein synthesis of MDA-MB-468 breast cancer cells after 24 treatment with tcyDTDO or DMtcyDTDO.

Cell viability (FIG. 12), proliferation (FIG. 13), and protein synthesis (FIG. 14) assays were performed in MDA-MB-468 cell line in the presence of increasing concentrations of tcyDTDO or DMtcyDTDO. The results clearly show that DMtcyDTDO exhibited a significantly greater effect on cell viability, proliferation, and protein synthesis when compared to equal doses of tcyDTDO.

Figure 15:
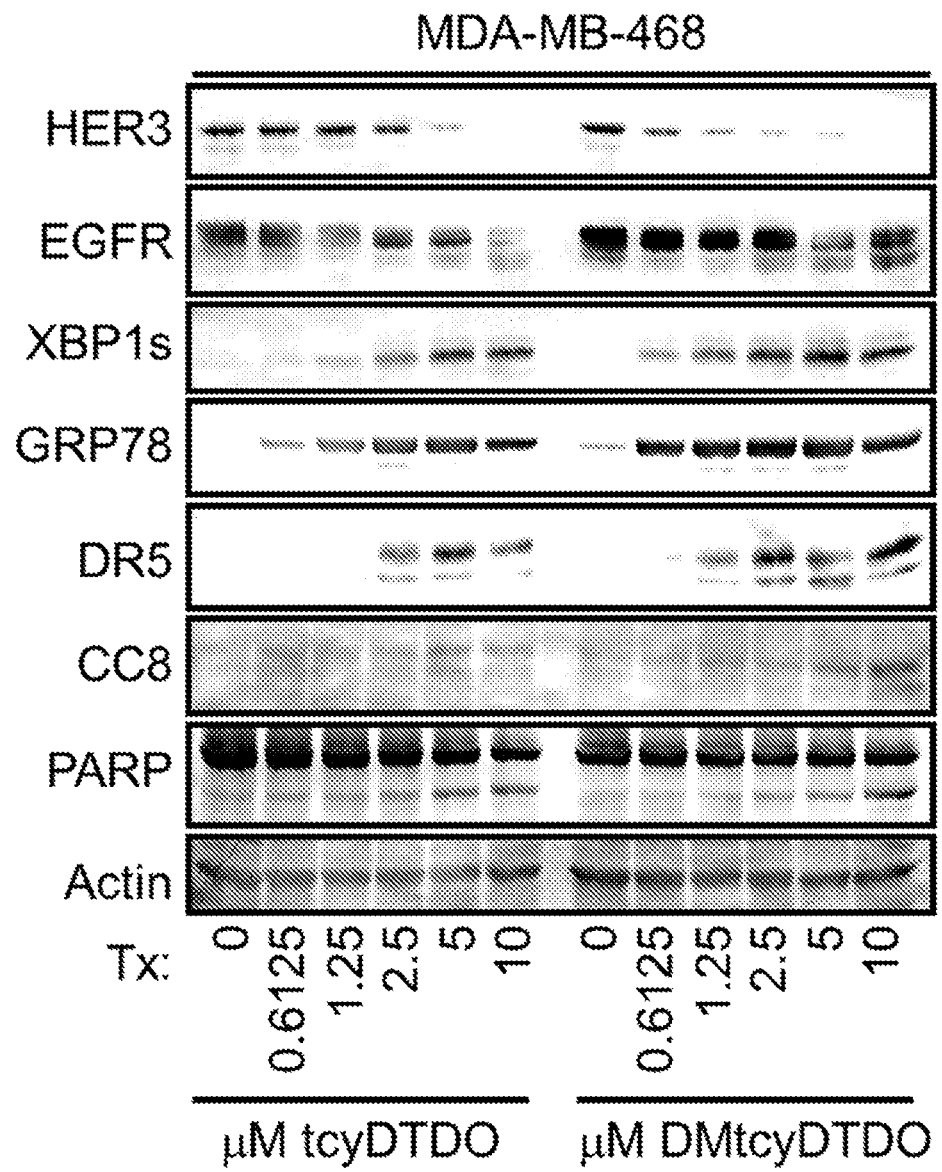
FIG. 15. depicts immunoblot analysis of HER-family members (EGFR, HER3), ER stress markers (XBP1s, GRP78), and cell death markers (DR5, CC8, and PARP) of MDA-MB-468 breast cancer cells after 24 treatment with tcyDTDO or DMtcyDTDO. Actin serves as a loading control.

The EGFR±MDA-MB-468 TNBC line harbors MYC amplification [A. Shadeo, W. L. Lam, Comprehensive copy number profiles of breast cancer cell model genomes, *Breast Cancer Res,* 8 (2006) R9], and are highly responsive to tcyDTDO and DMtcyDTDO treatment. TcyDTDO and DMtcyDTDO induce PARP cleavage in MDA-MB-468 (FIG. 15).

Figure 16:
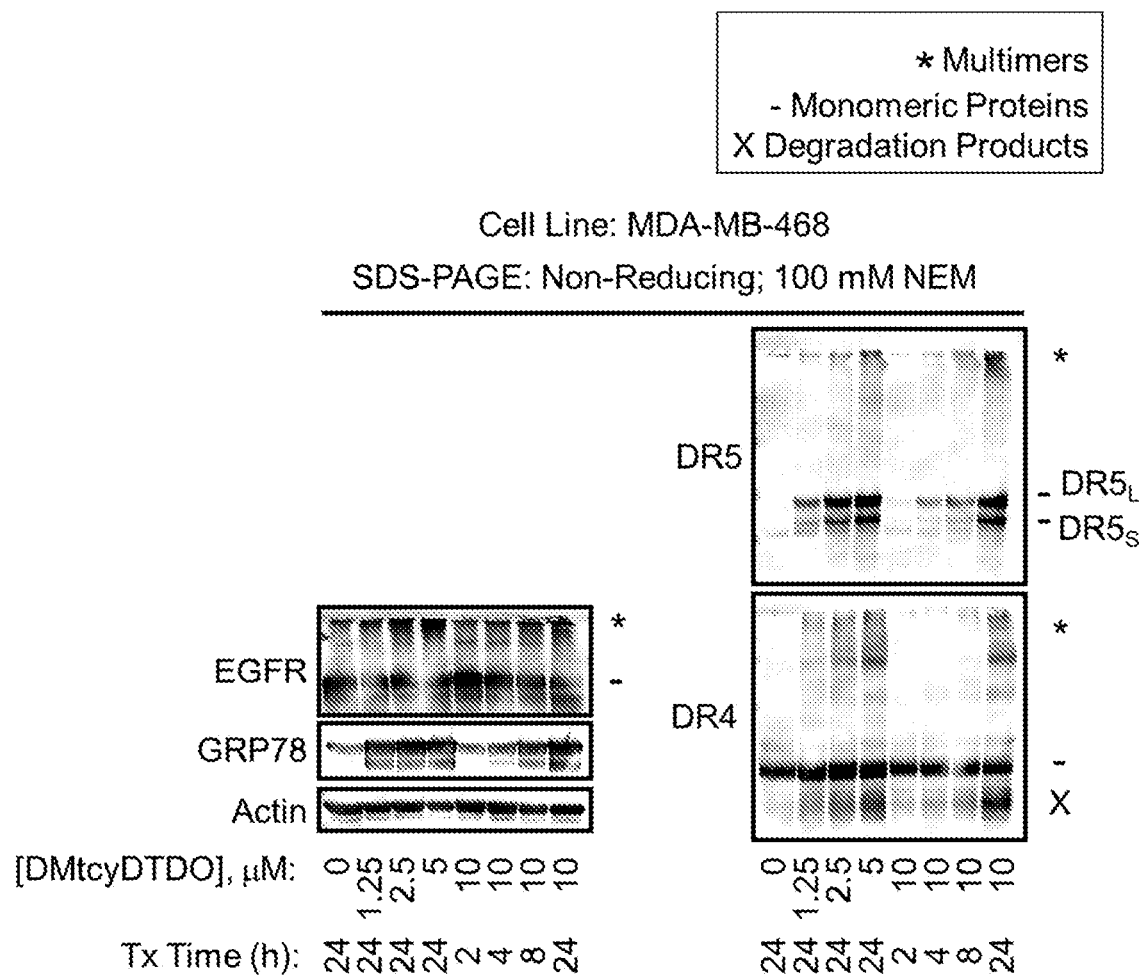
FIG. 16. depicts immunoblot analysis of MDA-MB-468 breast cancer cells after 24 treatment with DMtcyDTDO.

MDA-MB-468 breast cancer cells were treated for 24 h with the indicated concentrations of DMtcyDTDO and cells were analyzed by immunoblot. Cell extracts were prepared under non-reducing conditions in the presence of 100 mM N-ethylmaleimide to preserve disulfide bonding patterns (FIG. 16). DMtcyDTDO upregulates DR5 and induces oligomerization of EGFR, DR4, and DR5. The oligomerized forms of DR4 and DR5 represent the activated form of these receptors.

Figure 10:
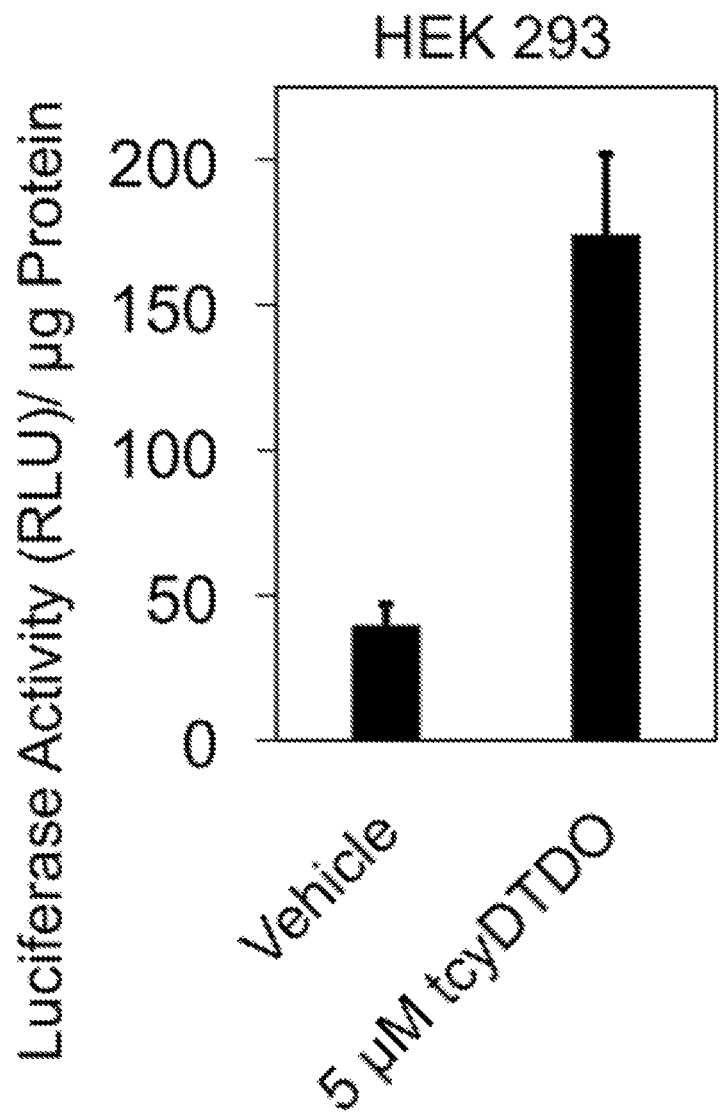
FIG. 10. depicts increases in DR5 transcription by tcyDTDO in HEK293 cells as measured using a transcriptional reporter construct.
Figure 11:
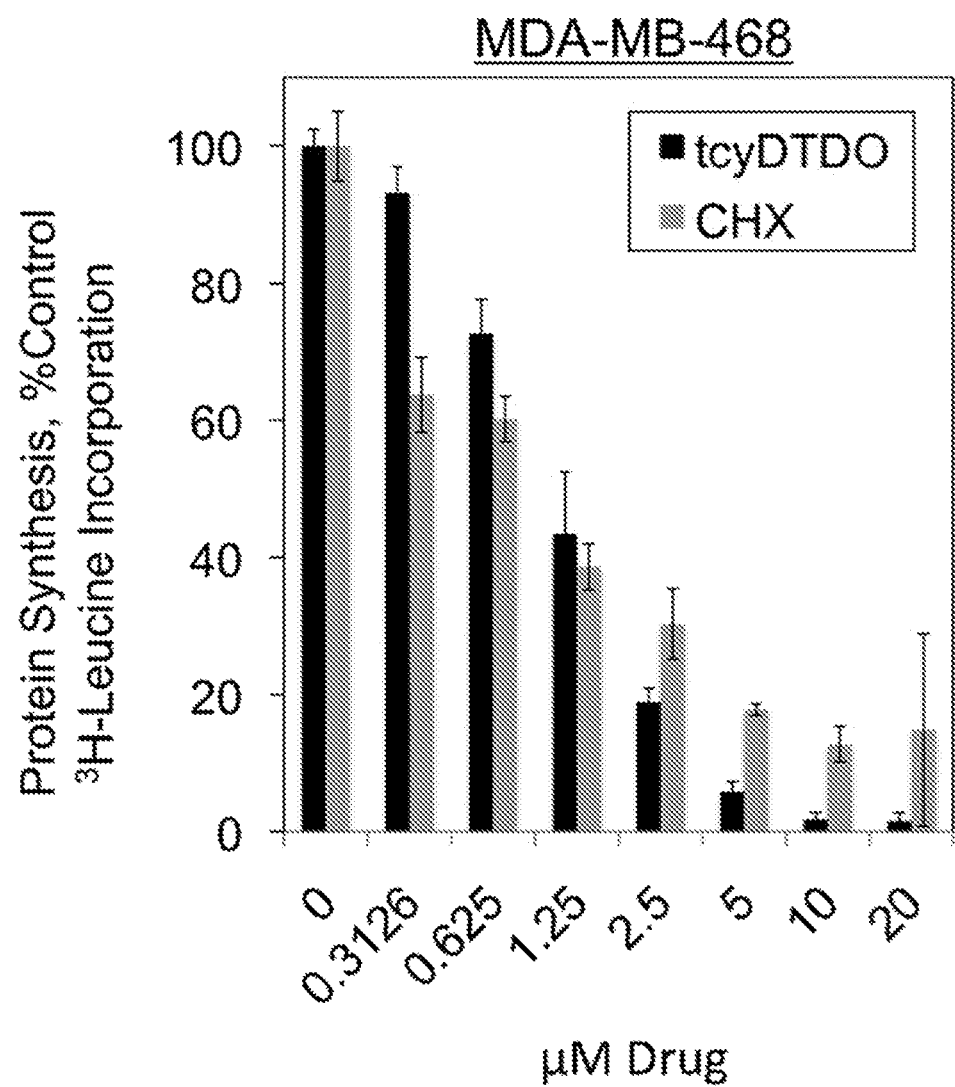
FIG. 11. depicts the inhibition of global protein synthesis upon treatment of MDA-MB-468 cells with tcyDTDO.

TcyDTDO (5 µM) increased DR5 transcription (FIG. 10) as measured using a transcriptional reporter construct, but under these conditions global protein synthesis was inhibited by more than 95% (FIG. 11). TcyDTDO inhibits protein synthesis in a similar concentration range as the protein synthesis inhibitor Cycloheximide. Thus, without being bound by any particular theory, it is speculated that compounds of Formula (I)-(VI) regulate DR5 steady-state protein levels in addition to the observed transcriptional induction.

What is claimed is:

1. A compound of Formula III, or salt thereof:

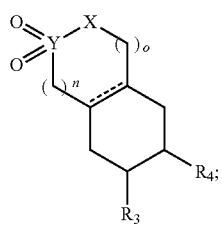

Formula III wherein, X is S or Se;
Y is S or Se;
$R_3$ is selected from H or $C_1$-$C_6$ alkoxy;
$R_4$ is selected from H or $C_1$-$C_6$ alkoxy;
n is 0, 1, 2, or 3;
o is 0, 1, 2, or 3; and
--- denotes a carbon-carbon single bond or double bond;
wherein if --- is a single bond, X and Y are both S, and n and o are each 1, then at least one of $R_3$ or $R_4$ is $C_1$-$C_6$ alkoxy.

2. A compound, wherein the compound is:
1,2-diselenane-1,1-dioxide;
3,6-dihydro-1,2-dithiine-1,1-dioxide;
trans-1,2-dithiane-4,5-diol-1,1-dioxide;
trans-1,2-dithiane-4,5-diamino-1,1-dioxide;
trans-1,2-dithiane-4,5-diazido-1,1-dioxide;
cis-1,2-dithiane-4,5-diol-1,1-dioxide;
cis-1,2-dithiane-4,5-diamino-1,1-dioxide;
cis-1,2-dithiane-4,5-diazido-1,1-dioxide;
1,2-dithiane-4,5-dione-1,1-dioxide;
1,2-dithiane-(4R,5S-diacetoxy)-1,1-dioxide;
1,2-dithiane-(4S,5R-diacetoxy)-1,1-dioxide;
1,2-dithiane-(4R,5R-diacetoxy)-1,1-dioxide;
1,2-dithiane-(4S,5S-diacetoxy)-1,1-dioxide;
1,2-dithiane-(4R,5S-dihydroxy)-1,1-dioxide;
1,2-dithiane-(4S,5R-dihydroxy)-1,1-dioxide;
1,2-dithiane-(4R,5R-dihydroxy)-1,1-dioxide;
1,2-dithiane-(4S,5S-dihydroxy)-1,1-dioxide;
1,2-dithiane-4-amino-1,1-dioxide;
1,2-dithiane-4-azido-1,1-dioxide;
1,2-dithiane-5-amino-1,1-dioxide;
1,2-dithiane-5-azido-1,1-dioxide;

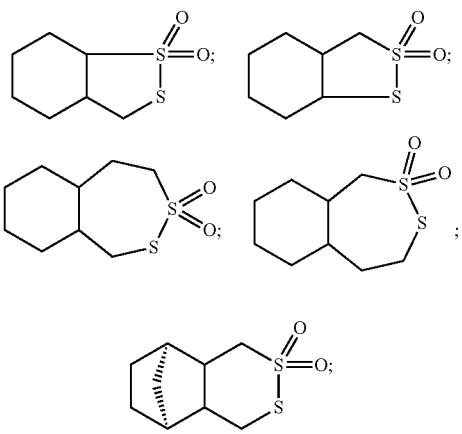

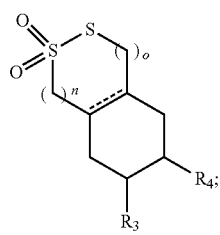

or a salt thereof.

3. The compound of claim 1, or salt thereof, according to Formula (IV):

Formula IV or salt thereof.

4. The compound of claim 1, or a salt thereof, according to Formula (V):

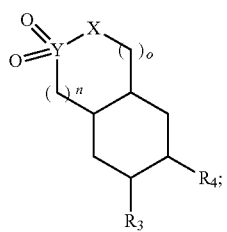

Formula V

Or salt thereof.

5. The compound of claim 1, or a salt thereof, according to Formula (VI):

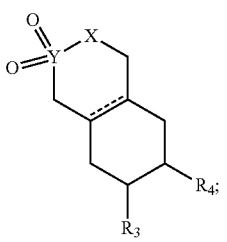

Formula VI or salt thereof.

6. The compound of claim 1, or a salt thereof, according to Formula (VII):

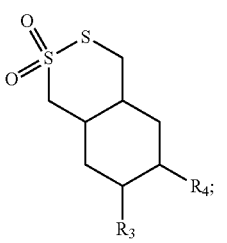

Formula VII

Or salt thereof.

7. The compound of claim 1, or a salt thereof, according to Formula (VIII):

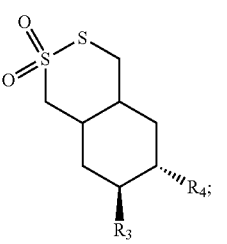

Formula VIII or salt thereof.

8. The compound of claim 1, or a salt thereof, according to Formula (XIII):

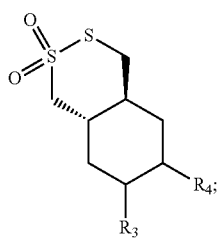

Formula XIII

Or salt thereof.

9. The compound of claim 1, or a salt thereof, according to Formula (XVI):

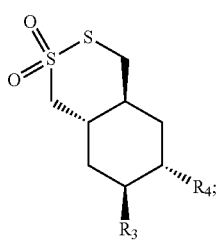

Formula XVI

Or salt thereof.

10. A pharmaceutical composition comprising a compound of claim 1, or salt thereof, and a pharmaceutically acceptable carrier.

11. The composition of claim 10, further comprising an additional therapeutic agent.

12. The composition of claim 11, wherein the additional therapeutic agent is an additional anti-cancer agent.

13. A compound that is

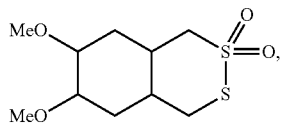 [SMILES: COC1CC2CSS(=O)(=O)CC2CC1OC]

or salt thereof.

14. The compound of claim 13, that is

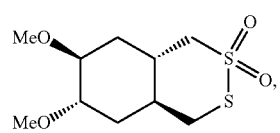

or a salt thereof.

* * * * *